US010369155B2

(12) United States Patent
Keilhack

(10) Patent No.: US 10,369,155 B2
(45) Date of Patent: Aug. 6, 2019

(54) METHOD FOR TREATING CANCER

(71) Applicant: Epizyme, Inc., Cambridge, MA (US)

(72) Inventor: Heike Keilhack, Belmont, MA (US)

(73) Assignee: Epizyme, Inc., Cambridge, MA (US)

( * ) Notice: Subject to any disclaimer, the term of this patent is extended or adjusted under 35 U.S.C. 154(b) by 0 days.

(21) Appl. No.: 15/851,978

(22) Filed: Dec. 22, 2017

(65) Prior Publication Data

US 2018/0133224 A1    May 17, 2018

Related U.S. Application Data

(60) Division of application No. 15/211,792, filed on Jul. 15, 2016, now Pat. No. 9,889,138, which is a continuation of application No. PCT/US2015/056022, filed on Oct. 16, 2015.

(60) Provisional application No. 62/064,948, filed on Oct. 16, 2014, provisional application No. 62/065,590, filed on Oct. 17, 2014.

(51) Int. Cl.
*A61K 31/45* (2006.01)
*A61K 45/06* (2006.01)
*A61P 35/00* (2006.01)
*A61P 37/00* (2006.01)
*A61K 31/453* (2006.01)
*A61K 31/5375* (2006.01)
*A61K 31/5377* (2006.01)

(52) U.S. Cl.
CPC .......... *A61K 31/5377* (2013.01); *A61K 31/45* (2013.01); *A61K 31/453* (2013.01); *A61K 45/06* (2013.01); *A61P 35/00* (2018.01); *A61P 37/00* (2018.01); *A61K 31/5375* (2013.01)

(58) Field of Classification Search
CPC .................................................. A61K 31/5377
USPC ........................................................ 514/235.5
See application file for complete search history.

(56) References Cited

U.S. PATENT DOCUMENTS

| 8,008,449 B2* | 8/2011 | Korman ............ A61K 47/6849 530/388.15 |
| 9,006,242 B2 | 4/2015 | Kuntz et al. |
| 9,089,575 B2 | 7/2015 | Kuntz et al. |
| 9,175,331 B2 | 11/2015 | Kuntz et al. |
| 9,334,527 B2 | 5/2016 | Kuntz et al. |
| 2014/0128393 A1 | 5/2014 | Knutson et al. |
| 2015/0051163 A1 | 2/2015 | Keilhack et al. |
| 2015/0344427 A1 | 3/2015 | Kuntz et al. |
| 2015/0284370 A1 | 10/2015 | Kuntz et al. |
| 2015/0352119 A1 | 12/2015 | Kuntz et al. |
| 2016/0228447 A1 | 8/2016 | Keilhack et al. |
| 2018/0071300 A1 | 3/2018 | Keilhack et al. |

FOREIGN PATENT DOCUMENTS

| WO | WO 2012/034132 A2 | 3/2012 |
| WO | WO 2012/118812 A2 | 9/2012 |
| WO | WO 2012/142504 A1 | 10/2012 |
| WO | WO 2012/142513 A1 | 10/2012 |
| WO | WO 2013/138361 A1 | 9/2013 |
| WO | WO 2013/155317 A1 | 10/2013 |
| WO | WO 2013/155464 A1 | 10/2013 |
| WO | WO 2014/062720 A2 | 4/2014 |
| WO | WO 2014/062732 A1 | 4/2014 |
| WO | WO 2014/062733 A2 | 4/2014 |
| WO | WO 2014/100080 A1 | 6/2014 |
| WO | WO 2014/100646 A1 | 6/2014 |
| WO | WO 2014/100665 A1 | 6/2014 |
| WO | WO 2014/144747 A1 | 9/2014 |
| WO | WO 2014/172044 A1 | 10/2014 |
| WO | WO 2015/010049 A1 | 1/2015 |
| WO | WO 2015/010078 A2 | 1/2015 |
| WO | WO 2015/057859 A1 | 4/2015 |
| WO | WO 2015/058125 A1 | 4/2015 |
| WO | WO 2015/085325 A1 | 6/2015 |
| WO | WO 2015/195848 A1 | 12/2015 |
| WO | WO 2015/195848 A8 | 12/2015 |
| WO | WO 2015/200650 A9 | 12/2015 |

OTHER PUBLICATIONS

Ciarapica, R. et al. (2011) "Enhancer of zeste homolog 2 (EZH2) in pediatric soft tissue sarcomas: first implications", *BMC Medicine*, vol. 9:63, pp. 1-9.
Hollmann, T.J. et al. (2011) "INI1-Deficient Tumors: Diagnostic Features and Molecular Genetics," *Am. J. Surg. Pathol.*, vol. 35, pp. e47-e63.
Kadoch, C. et al. (Mar. 28, 2013) "Reversible Disruption of mSWI/SNF (BAF) Complexes by the SS18-SSX Oncogenic Fusion in Synovial Sarcoma," *Cell*, vol. 153, pp. 71-85.
Knutson, S.K. et al. (May 7, 2013) "Durable tumor regression in genetically altered malignant rhabdoid tumors by inhibition of methyltransferase EZH2," *PNAS*, vol. 110, No. 19, pp. 7922-7927.
Knutson, S.K. et al. (Apr. 1, 2014) "Selective Inhibition of EZH2 by EPZ-6438 Leads to Potent Antitumor Activity in EZH2-Mutant Non-Hodgkin Lymphoma" *Mol. Cancer Ther.*, vol. 13, No. 4, pp. 842-854.
Truax, A. D. et al. (2012) "Dysregulated Recruitment of the Histone Methyltransferase EZH2 to the Class II Transactivator (CIITA) Promoter IV in Breast Cancer Cells", *PLOS ONE*, vol. 7, issue 4, p. e36013.
Vella, S. et al. (2013) "EZH2 Down-Regulation Exacerbates Lipid Accumulation and Inflammation in In Vitro and In Vivo NAFLD", *International Journal of Molecular Sciences*, vol. 14, issue 12, pp. 24154-24168.

(Continued)

*Primary Examiner* — Kevin E Weddington
(74) *Attorney, Agent, or Firm* — Cooley LLP; Heidi A. Erlacher; Christine Pemberton

(57) ABSTRACT

The present invention provides a method for treating or alleviating a symptom of a disorder, e.g., immune evasion, cancer-cell induced immune dysfunction, reduced immune response, lowered inflammation, decreased expression of a major histocompatibility complex (MHC), or cancer, characterized by aberrant, misregulated, or increased Enhancer of Zeste Homolog 2 (EZH2) activity in a cell or subject in need thereof by contacting the cell or administering to the subject a therapeutically effective amount of an EZH2 inhibitor.

20 Claims, 17 Drawing Sheets

(56) References Cited

OTHER PUBLICATIONS

Garapaty-Rao, S. et al. (Nov. 2013) "Identification of EZH2 and EZH1 Small Molecule Inhibitors with Selective Impact on Diffuse Large B Cell Lymphoma Cell Growth" *Chem Biol,* 20:1329-1339.
Knutson, S.K. et at (2012) "A Selective Inhibitor of EZH2 Blocks H3K27 Methylation and Kills Mutant Lymphoma Cells" *Nat Chem Biol,* 8:890-896.
Qi, W. et al. (2012) "Selective inhibition of Ezh2 by a small molecule inhibitor blocks tumor cells proliferation" *Proc Natl Acad Sci USA,* vol. 109, No. 52, p. 21360-21365.
Varambally, S. et at (2002) "The Polycomb Group Protein EZH2 Is Involved in Progression of Prostate Cancer" *Nature,* 419:624-629.

\* cited by examiner

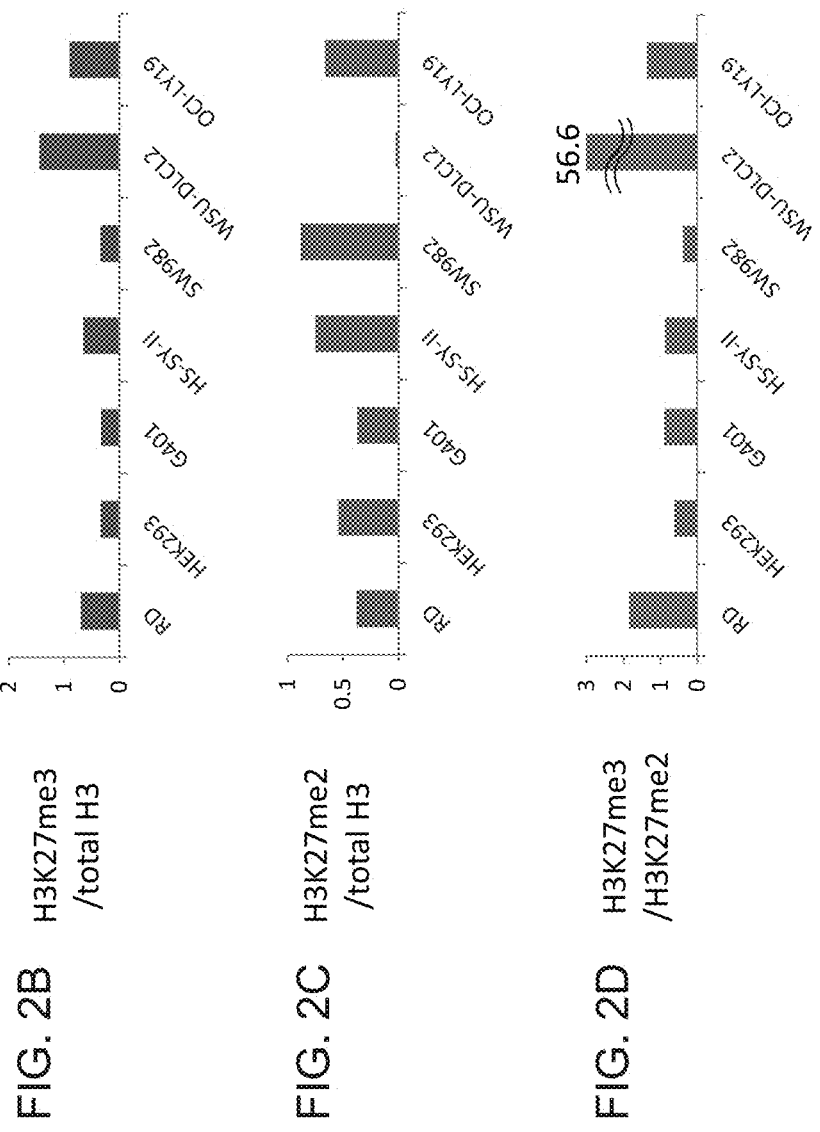

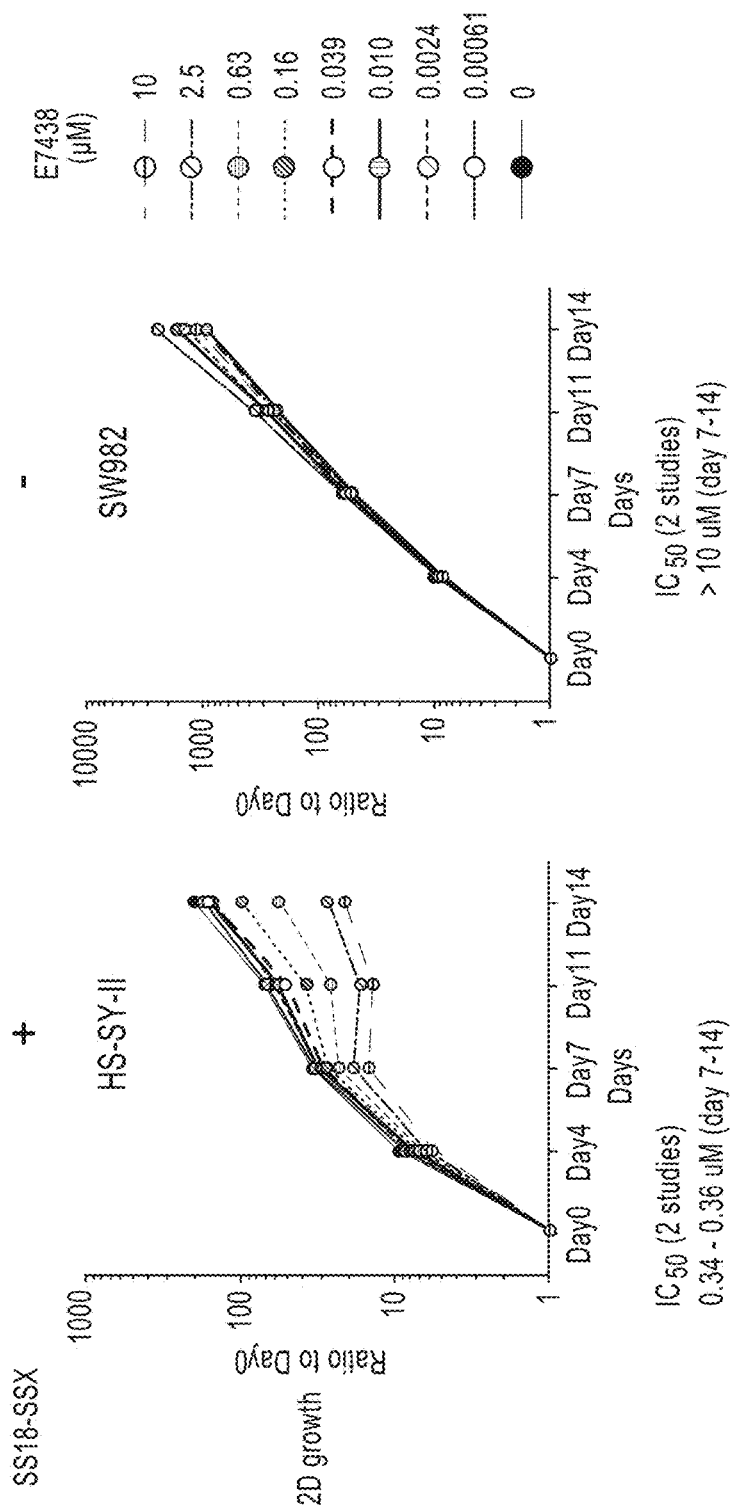

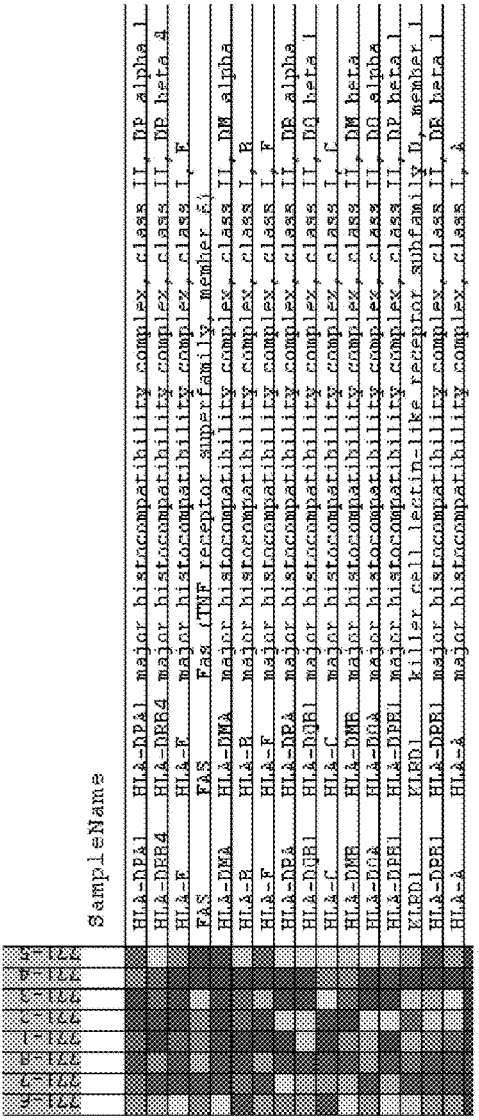
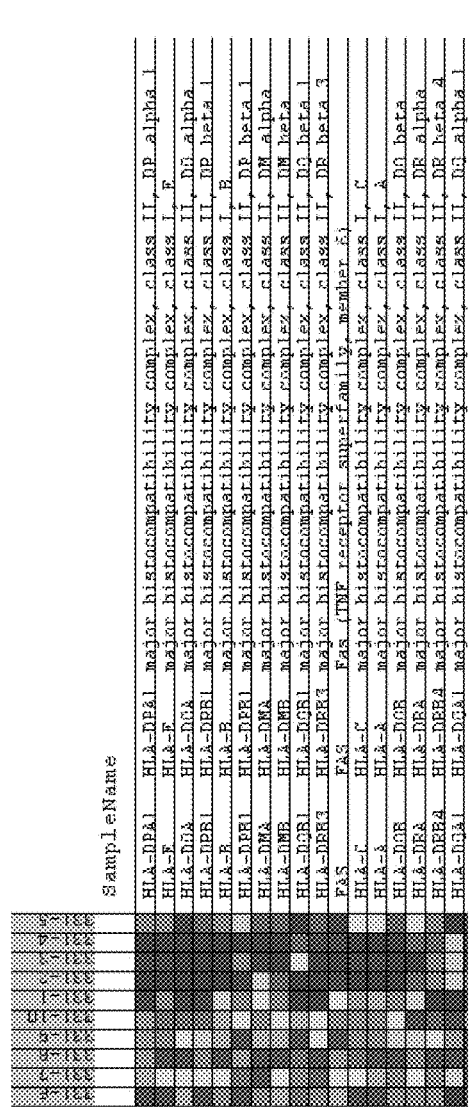
FIG. 12A
FIG. 12B

METHOD FOR TREATING CANCER

RELATED APPLICATIONS

This application is a divisional application of U.S. application Ser. No. 15/211,792, filed Jul. 15, 2016 (now issued as U.S. Pat. No. 9,889,138), which is a continuation application of International Application No. PCT/US2015/056022, filed Oct. 16, 2015, which claims the benefit of and priority to U.S. Provisional Patent Application Nos. 62/064,948, filed Oct. 16, 2014 and 62/065,590, filed on Oct. 17, 2014, the contents of each of which are incorporated herein by reference in their entireties.

BACKGROUND OF THE INVENTION

Disease-associated chromatin-modifying enzymes (e.g., EZH2) play a role in diseases such as proliferative disorders, metabolic disorders, and blood disorders. Thus, there is a need for the development of small molecules that are capable of modulating the activity of EZH2.

SUMMARY OF THE INVENTION

The present invention provides a method for treating or alleviating a symptom of a disorder, e.g., immune evasion, cancer-cell induced immune dysfunction, reduced immune response, lowered inflammation, decreased expression of a major histocompatibility complex (MHC), or cancer, characterized by aberrant, misregulated, or increased Enhancer of Zeste Homolog 2 (EZH2) activity and/or expression in a cell or subject in need thereof by contacting the cell or administering to the subject a therapeutically effective amount of an EZH2 inhibitor.

In a certain aspect, the method relates to inhibiting immune evasion in a cancer cell including a step of contacting the cell with a therapeutically effective amount of an EZH2 inhibitor.

In a certain aspect, the method relates to treating and/or correcting cancer-cell induced immune dysfunction in a subject in need thereof including a step of administering to the subject a therapeutically effective amount of an EZH2 inhibitor.

In a certain aspect, the method relates to boosting, increasing or inducing immune response in a subject in need thereof including a step of administering to the subject a therapeutically effective amount of an EZH2 inhibitor.

In a certain aspect, the method relates to increasing expression of a major histocompatibility complex (MHC) in a cancer cell including a step of contacting the cancer cell with a therapeutically effective amount of an EZH2 inhibitor.

In a certain aspect, the method relates to increasing inflammation in a subject in need thereof including a step of administering to the subject a therapeutically effective amount of an EZH2 inhibitor.

In a certain aspect, the method relates to treating a cancer or a cell proliferative disorder in a subject in need thereof including a step of administering to the subject a therapeutically effective amount of an EZH2 inhibitor.

In a certain aspect, the method relates to determining the likelihood of effectiveness of a treatment comprising an EZH2 inhibitor in a subject in need thereof including steps of (1) obtaining a biological sample from the subject; and (2) assaying the biological sample for a reduction in expression of a major histocompatibility complex (MHC) when compared to a control sample. A treatment including the EZH2 inhibitor is more likely to be effective in the subject when the biological sample has reduced expression of a MHC when compared to the control sample.

In a certain aspect, the method relates to determining the likelihood of effectiveness of a treatment comprising an EZH2 inhibitor in a subject in need thereof including assaying a biological sample obtained from the subject for a reduction in expression of a major histocompatibility complex (MHC) in a sample when compared to a control sample. A treatment including the EZH2 inhibitor is more likely to be effective in the subject if the biological sample has reduced expression of a MHC when compared to the control sample.

In a certain aspect, the method relates to screening the effectiveness of a treatment comprising an EZH2 inhibitor in a subject in need thereof including (1) obtaining a first and a second biological sample from the subject; (2) contacting the second biological sample with an EZH2 inhibitor; (3) assaying the first and the second biological sample for expression of a major histocompatibility complex (MHC); and (4) comparing expression of the MHC in the first biological sample to expression of the MHC in the second biological sample. A treatment including the EZH2 inhibitor is more likely to be effective in the subject if the second biological sample has increased expression of the MHC when compared to expression in the first biological sample.

In embodiments of the above aspects, the cell or the subject comprises aberrant, misregulated, or increased EZH2 activity.

In embodiments of the above aspects, the cell or the subject comprises a chromosomal translocation t(x;18)(p11.2;q11.2).

In embodiments of the above aspects, the translocation causes a SS18-SSX fusion gene.

In embodiments of the above aspects, the cell or the subject has reduced function or expression of INI1 (also referred herein as BAF47, SNF5, or SMARCB1).

In embodiments of the above aspects, the cell or the subject has reduced function and expression of INI1.

In embodiments of the above aspects, the EZH2 inhibitor is Compound A (also referred to herein as E7438 or EPZ-6438 or tazemetostat), having the following formula:

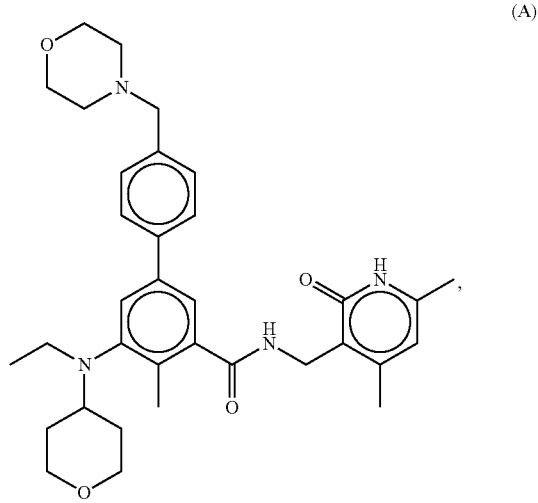

(A)

and pharmaceutically acceptable salts thereof or stereoisomer's thereof.

In embodiments of the above aspects, the EZH2 inhibitor is one or more of

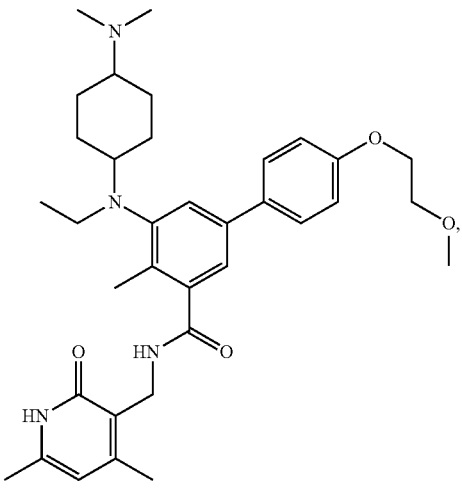
(B)

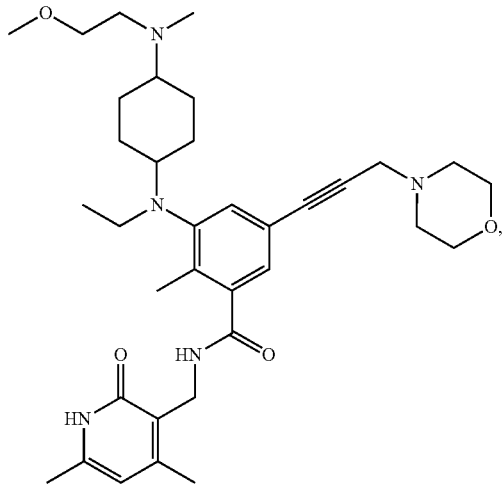
(C)

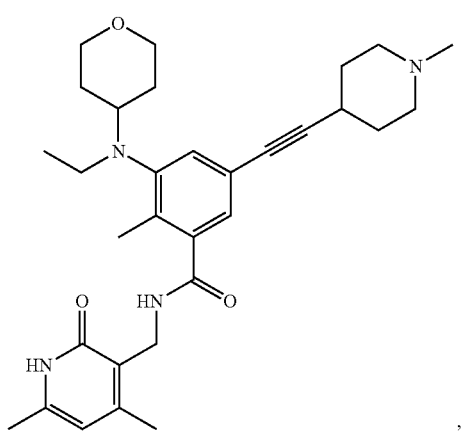
(D)

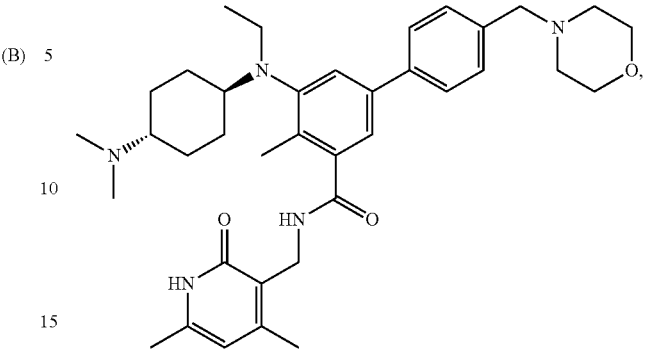
(E)

and pharmaceutically acceptable salts thereof or stereoisomer's thereof.

In embodiments of the above aspects, the method further includes administering a chemotherapeutic compound, e.g., a PD-1 inhibitor, a PD-L1 inhibitor, or a CTLA-4 inhibitor.

In embodiments of the above aspects, the cancer cell in in a subject, e.g., a human.

In embodiments of the above aspects, immune evasion, cancer-cell induced immune dysfunction, an immune response in need of boosting, inflammation, or cancer is characterized by reduced expression of one or more of MHC, β2 microglobulin, Tumor Necrosis Factor (TNF) receptor, Low Molecular Mass Polypeptide 2, (LMP2), Low Molecular Mass Polypeptide 7, (LMP7), Transporter Associated with Antigen Processing (TAP), and TAP-associated glycoprotein (tapasin) in a cancer cell when compared to a non-cancerous cell. The MHC can be human leukocyte antigen (HLA), e.g., HLA-A, HLA-B, HLA-C, HLA-DM alpha, HLA-DM beta, HLA-DO alpha, HLA-DO beta 1, HLA-DP alpha 1, HLA-DP beta 1, HLA-DR alpha, HLA-DR beta 1, HLA-DR beta 3, HLA-DR beta 4, HLA-E, HLA-F, HLA-G, HLA-K, or HLA-L.

Unless otherwise defined, all technical and scientific terms used herein have the same meaning as commonly understood by one of ordinary skill in the art to which this invention belongs. In the specification, the singular forms also include the plural unless the context clearly dictates otherwise. Unless specifically stated or obvious from context, as used herein, the terms "a," "an," and "the" are understood to be singular or plural. Unless specifically stated or obvious from context, as used herein, the term "or" is understood to be inclusive.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Although methods and materials similar or equivalent to those described herein can be used in the practice or testing of the present invention, suitable methods and materials are described below. All publications, patent applications, patents and other references mentioned herein are incorporated by reference. The references cited herein are not admitted to be prior art to the claimed invention. In the case of conflict, the present specification, including definitions, will control.

In addition, the materials, methods and examples are illustrative only and are not intended to be limiting.

Any of the above aspects and embodiments can be combined with any other aspect or embodiment.

Other features and advantages of the invention will be apparent from the following detailed description and claims.

DESCRIPTION OF THE FIGURES

FIGS. 2B to 2D are a series of plots showing quantitative H3K27me3/total H3 (B), H3K27me2/total H3 (C) or H3K27me3/H3K27me2 (D) ratio in various cell lines. These quantitative data were derived from the calculation of protein bands obtained by western blotting analysis.

FIGS. 5A and 5B are a series of plots showing that HS-SY-II cells are highly sensitive to Compound A (FIG. 5A) whereas SW982 cells are not (FIG. 5B). Each cell type was treated with Compound A with indicated concentrations. Cells were replated on Day 7 and treated for an additional 7 days. Cell viability was determined by CellTiter-Glo® Luminescent Cell Viability Assay.

FIG. 7A shows plasma concentrations of Compound A. Here, Compound A was given orally to mice twice daily for 7 days. Peripheral blood samples were collected at approximately 5 minutes before and 3 hours after the last dose from Compound A-treated mice. The analysis for plasma concentrations of Compound A was performed. The concentrations are plotted (n=5). Each bar represents a mean of plasma concentration in each group. FIG. 7B shows the inhibitory effects in mice of Compound A against H3K27me3 in HS-SY-II xenograft. Here, Compound A was given orally to mice twice daily for 7 days. H3K27me3 in the tumor are plotted (n=5). Each bar represents a mean±SEM of the trimethylation level in each group. Tables 2 and 3 below provide statistical analyses related to the data shown in FIG. 7B. The results of the statistical analyses confirm a dose-dependent change.

FIGS. 10A and 10B show results of the first study and FIG. 10C shows the results of the second study. Tumors from animals of the second study were harvested on Day 28 (3 h after the last dose) and subjected to H3K27me3 analysis by ELISA (FIG. 10D) or immunohistochemistry (IHC) for the proliferation marker Ki67 (FIG. 10E).

FIGS. 11A and 11B show data from mice bearing PDX from a 57 year old male with high-grade spindle cell sarcoma (CTG-0771). FIGS. 11C and 11D show data from mice bearing PDX from a 16 year old female (CTG-0331). Tumor volumes were measured twice a week. Dosing was stopped on Day 35 and animals were observed until day 60 with tumor measurements twice a week. When the tumor volume of a given animal exceeded 2000 mm$^3$, the mouse was euthanized (analyzed in the Kaplan-Meyer plot).

FIGS. 12A and 12B shows array data from synovial sarcoma PDX tumors from subsets of mice that were harvested on day 35 and analyzed by RNA-seq analysis. FIG. 12A is data from mice bearing PDX from the 57 year old male; FIG. 12B is data from mice bearing PDX from the 16 year old female. Expression of HLA genes in tumors from mice treated with either with vehicle or at 400 mg/kg Compound A BID are shown. In the figure, blue is low expression and red is high expression.

DETAILED DESCRIPTION OF THE INVENTION

Figure 1:
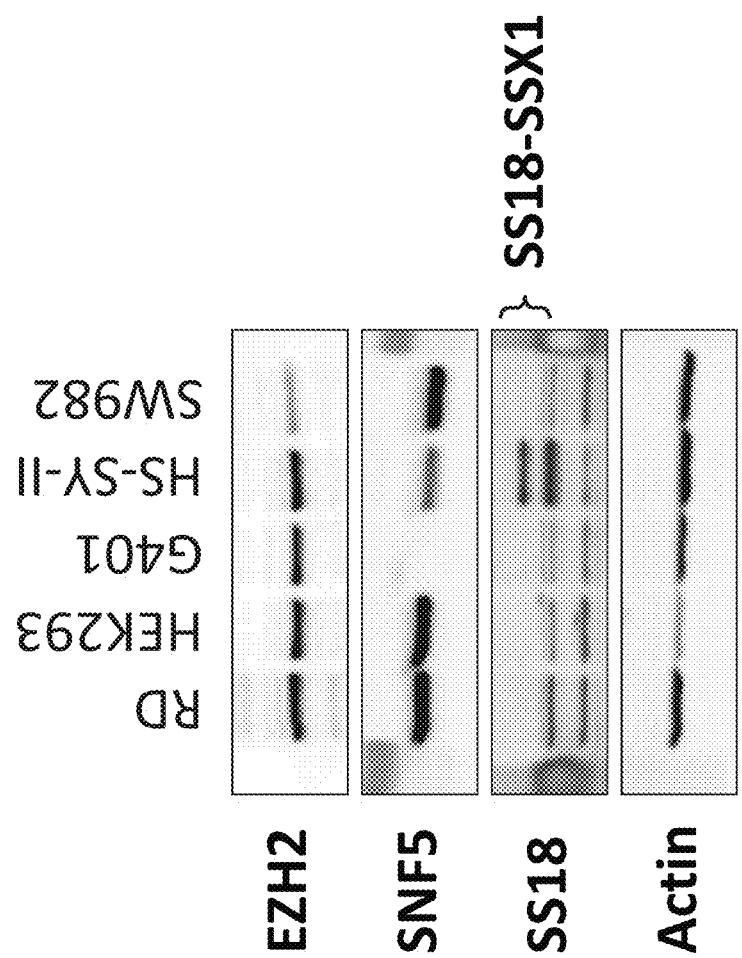
FIG. 1 is a western blot of cell lysates demonstrating SS18-SSX1 expression and INI1 (also referred herein as BAF47, SNF5, or SMARCB1) down-regulation in HS-SY-II cell line.

The present invention provides a method for treating or alleviating a symptom of disorder, e.g., immune evasion, cancer-cell induced immune dysfunction, reduced immune response, lowered inflammation, decreased expression of a major histocompatibility complex (MHC), or cancer, characterized by aberrant, misregulated, or increased Enhancer of Zeste Homolog 2 (EZH2) activity or expression in a cell or subject in need thereof by contacting the cell or administering to the subject a therapeutically effective amount of an EZH2 inhibitor. EZH2 is the enzymatic subunit of polycomb repressive complex 2 (PRC2), a complex that catalyzes the methylation of Histone 3 lysine 27 (H3K27). Histone 3 lysine 27 (H3K27) methylation is a transcriptionally repressive epigenetic mark that has been causally associated with a number of hematologic and solid human cancer(s). Several molecular mechanisms leading to a hypertrimethylated state of H3K27 have been reported among human cancers.

The present invention is based in part upon the discovery that EZH2 inhibitors may effectively treat immune evasion, or disorders characterized or induced by cancer-cell induced immune dysfunction, reduced immune response, lowered inflammation, decreased expression of a WIC.

In certain embodiments, cells, subjects, tumors or tumor cells having aberrant, misregulated, or increased EZH2 activity are sensitive to the EZH2 inhibitors of the present invention.

Human synovial sarcoma accounts for 8%-10% of all soft tissue malignancies and most commonly arises in the extremities of young adults. A recurrent chromosomal translocation, t(x;18)(p11.2;q11.2), fuses the SS18 gene on chromosome 18 to one of three closely related genes on the X chromosome, SSX1, SSX2, and rarely SSX4, resulting in an in-frame fusion protein in which the eight C-terminal amino acids of SS18 are replaced with 78 amino acids from the SSX C terminus. This results in the expression of an oncogenic SS18-SSX fusion protein that binds to the SWI/SNF complex evicting both the wild-type SS18 and the tumor suppressor INI1, which are subsequently degraded. This results in aberrant gene expression and ultimately the development of cancer.

The present invention provides methods for inhibiting immune evasion in a cancer cell including a step of contacting the cell with a therapeutically effective amount of an EZH2 inhibitor.

The present invention may also provide methods for treating or correcting cancer-cell induced immune dysfunction in a subject in need thereof including a step of administering to the subject a therapeutically effective amount of an EZH2 inhibitor.

The present invention may also provide methods for boosting, increasing or inducing immune response in a subject in need thereof including a step of administering to the subject a therapeutically effective amount of an EZH2 inhibitor The present invention may also provide methods for increasing expression or activity of a major histocompatibility complex (MHC) in a cancer cell including a step of contacting the cancer cell with a therapeutically effective amount of an EZH2 inhibitor.

The present invention may also provide methods for increasing inflammation in a subject in need thereof including a step of administering to the subject a therapeutically effective amount of an EZH2 inhibitor.

The present invention may also provide methods for treating a cancer or a cell proliferative disorder in a subject in need thereof including a step of administering to the subject a therapeutically effective amount of an EZH2 inhibitor.

The present invention may also provide methods for determining the likelihood of effectiveness of a treatment comprising an EZH2 inhibitor in a subject in need thereof including steps of (1) obtaining a biological sample from the subject; and (2) assaying the biological sample for a reduction in expression of a major histocompatibility complex (MHC) when compared to a control sample. A treatment including the EZH2 inhibitor is more likely to be effective in the subject when the biological sample has reduced expression of a MHC when compared to the control sample.

The present invention may also provide methods for determining the likelihood of effectiveness of a treatment comprising an EZH2 inhibitor in a subject in need thereof including assaying a biological sample obtained from the subject for a reduction in expression of a major histocompatibility complex (MHC) in a sample when compared to a control sample. A treatment including the EZH2 inhibitor is more likely to be effective in the subject if the biological sample has reduced expression of a MHC when compared to the control sample.

The present invention may also provide methods for screening the effectiveness of a treatment comprising an EZH2 inhibitor in a subject in need thereof including (1) obtaining a first and a second biological sample from the subject; (2) contacting the second biological sample with an EZH2 inhibitor; (3) assaying the first and the second biological sample for expression of a major histocompatibility complex (MHC); and (4) comparing expression of the MHC in the first biological sample to expression of the MHC in the second biological sample. A treatment including the EZH2 inhibitor is more likely to be effective in the subject if the second biological sample has increased expression of the MHC when compared to expression in the first biological sample.

In embodiments of the present invention, the cell or the subject comprises aberrant, misregulated, or increased EZH2 activity.

In embodiments of the present invention, the cell or the subject comprises a chromosomal translocation t(x;18) (p11.2;q11.2).

In embodiments of the present invention, the translocation causes a SS18-SSX fusion gene.

In embodiments of the present invention, the cell or the subject has reduced function or expression of INI1 (also referred herein as BAF47, SNF5, or SMARCB1). In embodiments of the present invention, the cell or the subject has reduced function and expression of INI1. In certain embodiments the cell or the subject is considered or determined to be INI1 negative or INI1 deficient.

In embodiments of the present invention, the EZH2 inhibitor is Compound A, having the following formula:

(A)

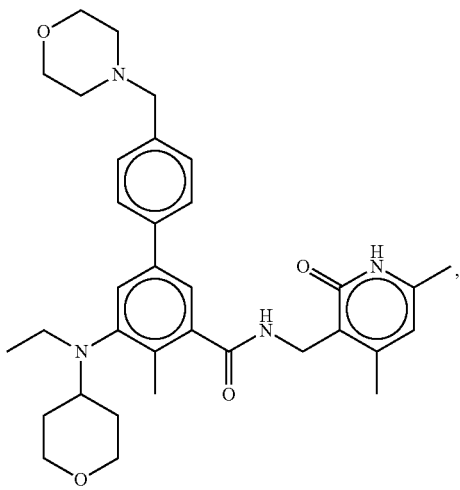

and pharmaceutically acceptable salts thereof.

In embodiments of the present invention, the EZH2 inhibitor is one or more of

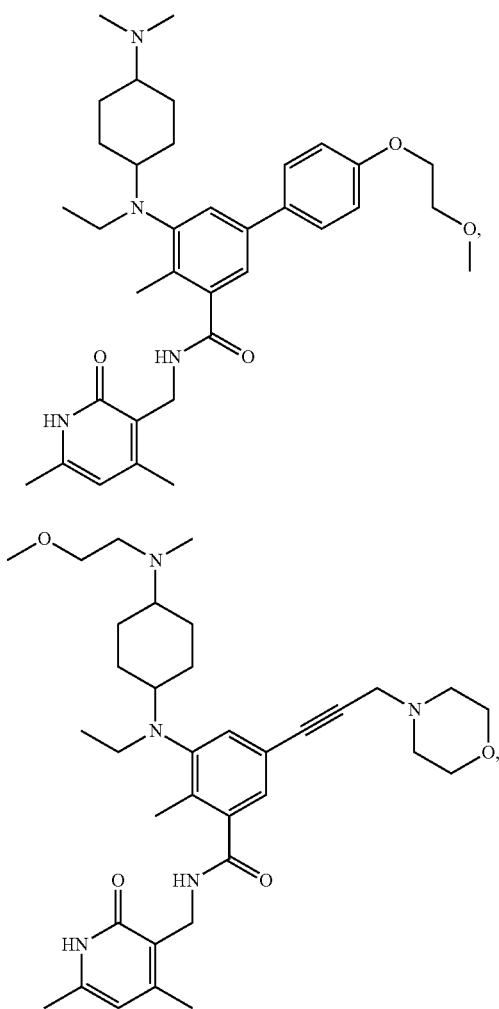

(B)

(C)

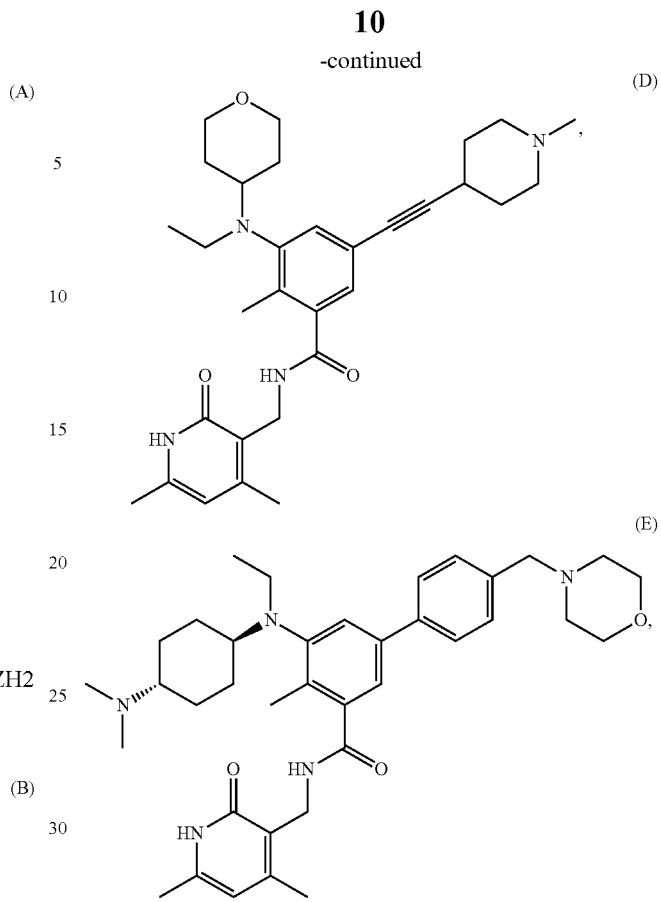

(D)

(E)

and pharmaceutically acceptable salts thereof.

In embodiments of the present invention, the method further includes administering a chemotherapeutic compound, e.g., a PD-1 inhibitor, a PD-L1 inhibitor, or a CTLA-4 inhibitor.

In embodiments of the present invention, the cancer cell is in a subject, e.g., a human.

In embodiments of the present invention, immune evasion, cancer-cell induced immune dysfunction, an immune response in need of boosting, inflammation, or cancer is characterized by reduced expression of one or more of MHC, β2 microglobulin, Tumor Necrosis Factor (TNF) receptor, Low Molecular Mass Polypeptide 2, (LMP2), Low Molecular Mass Polypeptide 7, (LMP7), Transporter Associated with Antigen Processing (TAP), and TAP-associated glycoprotein (tapasin) in a cancer cell when compared to a non-cancerous cell. The WIC can be human leukocyte antigen (HLA), e.g., HLA-A, HLA-B, HLA-C, HLA-DM alpha, HLA-DM beta, HLA-DO alpha, HLA-DO beta 1, HLA-DP alpha 1, HLA-DP beta 1, HLA-DR alpha, HLA-DR beta 1, HLA-DR beta 3, HLA-DR beta 4, HLA-E, HLA-F, HLA-G, HLA-K, or HLA-L.

Accordingly, the present invention may provide methods for the treatment of immune evasion, cancer-cell induced immune dysfunction, reduced immune response, lowered inflammation, decreased expression of a MHC in a cell or in a subject in need thereof by contacting the cell or administering to the subject a therapeutically effective amount of a compound of the present invention, or a pharmaceutically acceptable salt, solvate or polymorph thereof. The present invention may further provide the use of compound of the present invention, or a pharmaceutically acceptable salt, solvate or polymorph thereof, for the preparation of a medicament useful for the treatment of immune evasion, cancer-cell induced immune dysfunction, reduced immune response, lowered inflammation, decreased expression of a MHC.

In embodiments, the disorders are characterized by aberrant, misregulated, or increased EZH2 activity or expression. "Aberrant EZH2 activity" used herein refers to mis-location of EZH2 in a cell or mis-association of EZH2 with/within a protein complex. In embodiments, the aberrant EZH2 activity results from loss of regulatory function of INI1, which in turn may have occurred by a variety of genetic alterations, examples of some of which are discussed in greater detail herein. In certain embodiments, aberrant, misregulated, or increased EZH2 activity or expression is associated or results in increased trimethylation of H3K27.

In embodiments, disorder is characterized by a chromosomal translocation t(x;18)(p11.2;q11.2). Such translocation causes a SS18-SSX fusion gene.

In embodiments, the subject in need of treatment has aberrant, misregulated, or increased EZH2 activity.

In embodiments, the subject in need of treatment has reduced function or expression of INI1, or both. In embodiments, the subject has no detectable function or expression of INI1, or both.

In embodiments of the invention the synovial sarcoma is characterized by a SSX1 fusion. In another embodiment the synovial sarcoma is characterized by a SSX2 fusion. In embodiments, the synovial sarcoma is characterized by a SSX4 fusion. In embodiments, the subject in need of treatment, the treatment regimen, dose and frequency of administration is selected according to the type of SSX fusion that is detected. In embodiments the EZH2 inhibitor to be administered is also selected according to the SSX fusion associated with the cancer.

The present invention may also provide methods for the treatment of cancer in a subject in need thereof by administering to the subject a therapeutically effective amount of a compound described herein, or a pharmaceutically acceptable salt, solvate or polymorph thereof, where the subject in need of treatment has a chromosomal translocation t(x;18)(p11.2;q11.2) or a SS18-SSX fusion gene. The present invention further provides the use of a compound of the present invention, or a pharmaceutically acceptable salt, solvate or polymorph thereof for the preparation of a medicament useful for the treatment of cancer.

In embodiments, the method includes a step of determining the presence of a chromosomal translocation t(x;18)(p11.2;q11.2) or a SS18-SSX fusion gene in a sample from a subject before the administering step.

Determination of the presence of a chromosomal translocation t(x;18)(p11.2;q11.2) in a sample can be carried out with any method known in the art. For example, it can be determined by karyotyping and RT-PCR for SS18-SSX transcripts; or by FISH (fluorescent in situ hybridization). A SS18-SSX fusion gene can be detected by any method known in the art. For example, it can be detected by RT-PCT, immunohistostaining assay, or fluorescent in situ hybridization (FISH).

A cancer that is to be treated can be evaluated by DNA cytometry, flow cytometry, or image cytometry. A cancer that is to be typed as having 10%, 20%, 30%, 40%, 50%, 60%, 70%, 80%, or 90% of cells in the synthesis stage of cell division (e.g., in S phase of cell division). A cancer that is to be treated can be typed as having a low S-phase fraction or a high S-phase fraction.

In aspects of the invention the synovial sarcoma is monophasic synovial sarcoma. In other aspects of the invention the synovial sarcoma is biphasic synovial sarcoma.

The present invention also provides methods that include steps of detecting the presence of a chromosomal translocation t(x;18)(p11.2;q11.2) or a SS18-SSX fusion gene in a sample from a subject and treating the subject by administering a therapeutically effective amount of a compound or a pharmaceutically acceptable salt, solvate or polymorph thereof.

The present invention further provides methods that include selecting a treatment regimen including administering to the candidate subject a therapeutically effective amount of a compound or a pharmaceutically acceptable salt or solvate thereof. The treating regimen may also include surgery, chemotherapy, radiation therapy, immunotherapy, or any combination thereof.

In embodiments, the method of the invention includes administering a therapeutically effective amount of an EZH2 inhibitor to the subject, surgery, chemotherapy, radiation therapy, acupuncture, immunotherapy, or any combination thereof. Chemotherapy (typically Doxorubicin and/or Ifosfamide) might be recommended in the treatment of synovial sarcoma, especially in advanced or metastatic disease.

The present invention further provides a method for treating a cancer or a cell proliferative disorder associated with aberrant, misregulated, or increased EZH2 activity in a subject in need thereof by administering to the subject a therapeutically effective amount of a compound of the present invention, or a pharmaceutically acceptable salt, solvate or polymorph thereof. For example, the cancer is synovial sarcoma. For example, the cancer is epithelioid sarcoma, extraskeletal myxoid chondrosarcoma, malignant rhabdoid tumor, or atypical chordoma.

For example, the EZH2 inhibitor that can be used herein includes Compound A, B, C, D or E. Compound A is also referred to herein as E7438 or EPZ-6438.

As used herein, a "subject in need thereof" is a subject having a cancer associated with aberrant, misregulated, or increased EZH2 activity or a subject having a cancer mediated by a chromosomal translocation t(x;18)(p11.2;q11.2). For example, the subject in need thereof has synovial sarcoma.

In embodiments, the subject in need thereof had at least one prior therapy to treat a disorder associated with aberrant, misregulated, or increased EZH2 activity.

In embodiments, the subject has refractory cancer on most recent therapy. "Refractory cancer" means any cancer described herein, including synovial sarcoma that does not respond to treatment. The cancer may be resistant at the beginning of treatment or it may become resistant during treatment. Refractory cancer is also called resistant cancer. In embodiments, the subject in need thereof has cancer recurrence following remission on most recent therapy. In embodiments, the subject received and failed all known effective therapies for synovial sarcoma that the subject is suffering from.

In embodiments, the subject is simultaneously being treated with another therapy to treat cancer mediated by a chromosomal translocation t(x;18)(p11.2;q11.2), for example, synovial sarcoma.

A "subject" includes a mammal. The mammal can be e.g., any mammal, e.g., a human, primate, mouse, rat, dog, cat, cow, horse, goat, camel, sheep or a pig. Preferably, the mammal is a human.

In embodiments, the subject has increased trimethylation level of Lys27 of histone H3 (H3-K27me3). In embodiments, aberrant, misregulated, or increased EZH2 activity or a chromosomal translocation t(x;18)(p11.2;q11.2) is associated with increased trimethylation level of H3-K27me.

As used herein, a "sample from a subject" refers to any suitable sample containing cells or components of cells obtained or derived from a subject. For example, in embodiments the sample includes cancer cells. In embodiments the sample is a biopsy sample obtained from, for example, soft tissues (e.g., joints). In embodiments the sample is a biopsy sample obtained from a tissue other than or in addition to a soft tissue. For example, in embodiments the sample is a biopsy from a cancer, e.g., a tumor composed of cancer cells. Cells in the sample can be isolated from other components of the sample in accordance with methods familiar to those of skill in the art. For example, in embodiments, the sample is tissue, organ, or bodily fluid such as whole blood, plasma, serum, urine, saliva, genital secretion, cerebrospinal fluid, sweat or excreta.

As used herein, "monotherapy" refers to the administration of a single active or therapeutic compound to a subject in need thereof. Preferably, monotherapy will involve administration of a therapeutically effective amount of a single active compound. For example, cancer monotherapy with one of the compound of the present invention, or a pharmaceutically acceptable salt, or solvate thereof, to a subject in need of treatment of cancer associated with aberrant, misregulated, or increased EZH2 activity. In one aspect, the single active compound is a compound of the present invention, or a pharmaceutically acceptable salt, solvate or polymorph thereof. In a certain embodiment, the single active compound is tazemetostat.

As used herein, "treating" or "treat" describes the management and care of a patient for the purpose of combating a disease, condition, or disorder associated with aberrant, misregulated, or increased EZH2 activity and includes the administration of a compound of the present invention, or a pharmaceutically acceptable salt, solvate or polymorph thereof, to alleviate the symptoms or complications of the disease, condition or disorder, or to eliminate the disease, condition or disorder.

A compound of the present invention, or a pharmaceutically acceptable salt, solvate or polymorph thereof may also be used to prevent a disease, condition or disorder associated with aberrant, misregulated, or increased EZH2 activity. As used herein, "preventing" or "prevent" describes reducing or eliminating the onset of the symptoms or complications of the disease, condition or disorder.

As used herein, the term "alleviate" is meant to describe a process by which the severity of a sign or symptom of a disorder is decreased. Importantly, a sign or symptom can be alleviated without being eliminated. In a preferred embodiment, the administration of pharmaceutical compositions of the invention leads to the elimination of a sign or symptom, however, elimination is not required. Effective dosages are expected to decrease the severity of a sign or symptom. For instance, a sign or symptom of a disorder such as cancer, which can occur in multiple locations, is alleviated if the severity of the cancer is decreased within at least one of multiple locations.

As used herein the term "symptom" is defined as an indication of disease, illness, injury, or that something is not right in the body. Symptoms are felt or noticed by the individual experiencing the symptom, but may not easily be noticed by others. Others are defined as non-health-care professionals.

As used herein the term "sign" is also defined as an indication that something is not right in the body. But signs are defined as things that can be seen by a doctor, nurse, or other health care professional.

Treating cancer(s) or cell proliferative disorder(s) associated with aberrant, misregulated, or increased EZH2 activity with compounds described herein may result in a reduction in size or volume of a tumor or reduction of tumor growth or regrowth or any combination of the above. A reduction in size or volume of a tumor may also be referred to as "tumor regression". Preferably, after treatment, tumor size is reduced by 5% or greater relative to its size prior to treatment; more preferably, tumor size is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Size or volume of a tumor may be measured by any reproducible means of measurement. The size or volume of a tumor may be measured as a diameter of the tumor.

Treating cancer(s) or cell proliferative disorder(s) associated with aberrant, misregulated, or increased EZH2 activity or expression with compounds described herein may result in a decrease in number of tumors. Preferably, after treatment, tumor number is reduced by 5% or greater relative to number prior to treatment; more preferably, tumor number is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. Number of tumors may be measured by any reproducible means of measurement. The number of tumors may be measured by counting tumors visible to the naked eye or at a specified magnification.

Treating cancer(s) or cell proliferative disorder(s) associated with aberrant, misregulated, or increased EZH2 activity with compounds described herein may result in an increase in average survival time or a decrease in mortality rate or both of a population of treated subjects in comparison to a population of untreated subjects or subjects receiving carrier alone. In a certain embodiment the population of treated subjects is receiving therapy with a drug or a combination of drugs that are not a compound of the present invention. Preferably, the average survival time is increased by more than 10, 20, or 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer(s) or cell proliferative disorder(s) associated with aberrant, misregulated, or increased EZH2 activity with compounds described herein may result in a decrease in the mortality rate of a population of treated subjects in comparison to a population receiving carrier alone. Treating cancer(s) or cell proliferative disorder(s) associated with aberrant, misregulated, or increased EZH2 activity with compounds described herein may result in a decrease in the mortality rate of a population of treated subjects in comparison to an untreated population. Treating cancer(s) or cell proliferative disorder(s) associated with aberrant, misregulated, or increased EZH2 activity with compounds described herein may result in a decrease in the mortality rate of a population of treated subjects in comparison to a population receiving monotherapy with a drug that is not a compound of the present invention, or a pharmaceutically acceptable salt or solvate thereof. Preferably, the mortality rate is decreased by more than 2%; more preferably, by more than 5%; more preferably, by more than 10%; and most preferably, by more than 25%. A decrease in the mortality rate of a population of treated subjects may be measured by any reproducible means. A decrease in the mortality rate of a population may be measured, for example, by calculating for a population the average number of disease-related deaths per unit time following initiation of treatment with an active compound. A decrease in the mortality rate of a population may also be measured, for example, by calculating for a population the average number of disease-related deaths per unit time following completion of a first round of treatment with an active compound.

Treating cancer(s) or cell proliferative disorder(s) associated with aberrant, misregulated, or increased EZH2 activity with compounds described herein may result in a decrease in tumor growth rate. Preferably, after treatment, tumor growth rate is reduced by at least 5% relative to number prior to treatment; more preferably, tumor growth rate is reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Tumor growth rate may be measured by any reproducible means of measurement. Tumor growth rate can be measured according to a change in tumor diameter per unit time.

Treating cancer(s) or cell proliferative disorder(s) associated with aberrant, misregulated, or increased EZH2 activity with compounds described herein may result in a decrease in tumor regrowth. Preferably, after treatment, tumor regrowth is less than 5%; more preferably, tumor regrowth is less than 10%; more preferably, less than 20%; more preferably, less than 30%; more preferably, less than 40%; more preferably, less than 50%; even more preferably, less than 50%; and most preferably, less than 75%. Tumor regrowth may be measured by any reproducible means of measurement. Tumor regrowth is measured, for example, by measuring an increase in the diameter of a tumor after a prior tumor shrinkage that followed treatment. A decrease in tumor regrowth is indicated by failure of tumors to reoccur after treatment has stopped.

Treating or preventing cancer(s) associated with aberrant, misregulated, or increased EZH2 activity with compounds described herein may result in a decrease in the number or proportion of cells having an abnormal appearance or morphology. Preferably, after treatment, the number of cells having an abnormal morphology is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. An abnormal cellular appearance or morphology may be measured by any reproducible means of measurement. An abnormal cellular morphology can be measured by microscopy, e.g., using an inverted tissue culture microscope. An abnormal cellular morphology can take the form of nuclear pleiomorphism.

Treating cancer(s) or cell proliferative disorder(s) associated with aberrant, misregulated, or increased EZH2 activity with compounds described herein may result in cell death, and preferably, cell death results in a decrease of at least 10% in number of cells in a population. More preferably, cell death means a decrease of at least 20%; more preferably, a decrease of at least 30%; more preferably, a decrease of at least 40%; more preferably, a decrease of at least 50%; most preferably, a decrease of at least 75%. Number of cells in a population may be measured by any reproducible means. A number of cells in a population can be measured by fluorescence activated cell sorting (FACS), immunofluorescence microscopy and light microscopy. Methods of measuring cell death are as shown in Li et al., *Proc Natl Acad Sci USA*. 100(5): 2674-8, 2003. In a certain aspect, cell death occurs by apoptosis.

As used herein, the term "selectively" means tending to occur at a higher frequency in one population than in another population. The compared populations can be cell populations. Preferably, a compound of the present invention, or a pharmaceutically acceptable salt, solvate or polymorph thereof, acts selectively on a cancer or precancerous cell but not on a normal cell. Preferably, a compound of the present invention, or a pharmaceutically acceptable salt, solvate or polymorph thereof, acts selectively to modulate one molecular target (e.g., a target protein methyltransferase) but does not significantly modulate another molecular target (e.g., a non-target protein methyltransferase). The invention also provides a method for selectively inhibiting the activity of an enzyme, such as EZH2. Preferably, an event occurs selectively in population A relative to population B if it occurs greater than two times more frequently in population A as compared to population B. An event occurs selectively if it occurs greater than five times more frequently in population A. An event occurs selectively if it occurs greater than ten times more frequently in population A; more preferably, greater than fifty times; even more preferably, greater than 100 times; and most preferably, greater than 1000 times more frequently in population A as compared to population B. For example, cell death would be said to occur selectively in cancer cells if it occurred greater than twice as frequently in cancer cells as compared to normal cells.

Administering a compound of the present invention, or a pharmaceutically acceptable salt, solvate or polymorph thereof, to a cell or a subject in need thereof may result in modulation (i.e., inhibition) of an activity of EZH2.

Administering a compound of the present invention, or a pharmaceutically acceptable salt, solvate or polymorph thereof, to a cell or a subject in need thereof results in modulation (i.e., inhibition) of EZH2.

Activating refers to placing a composition of matter (e.g., protein or nucleic acid) in a state suitable for carrying out a desired biological function. A composition of matter capable of being activated also has an inactivated state. An activated composition of matter may have an inhibitory or stimulatory biological function, or both.

Elevation refers to an increase in a desired biological activity of a composition of matter (e.g., a protein or a nucleic acid). Elevation may occur through an increase in concentration of a composition of matter.

A compound (i.e., an EZH2 inhibitor) that can be used in any methods described herein may have the following Formula I:

(I)

or a pharmaceutically acceptable salt, solvate or polymorph thereof;
wherein $R^{701}$ is H, F, $OR^{707}$, $NHR^{707}$, —(C≡C)—$(CH_2)_{n7}$—$R^{708}$, phenyl, 5- or 6-membered heteroaryl, $C_{3-8}$ cycloalkyl, or 4-7 membered heterocycloalkyl containing 1-3 heteroatoms, wherein the phenyl, 5- or 6-membered heteroaryl, $C_{3-8}$ cycloalkyl or 4-7 membered heterocycloalkyl each independently is optionally substituted with one or more groups selected from halo, $C_{1-3}$ alkyl, OH, O—$C_{1-6}$ alkyl, NH—$C_{1-6}$ alkyl, and, $C_{1-3}$ alkyl substituted with $C_{3-8}$ cycloalkyl or 4-7 membered heterocycloalkyl containing 1-3 heteroatoms, wherein each of the O—$C_{1-6}$ alkyl and NH—$C_{1-6}$ alkyl is optionally substituted with hydroxyl, O—$C_{1-3}$ alkyl or NH—$C_{1-3}$ alkyl, each of the O—$C_{1-3}$ alkyl and NH—$C_{1-3}$ alkyl being optionally further substituted with O—$C_{1-3}$ alkyl or NH—$C_{1-3}$ alkyl;

each of $R^{702}$ and $R^{703}$, independently is H, halo, $C_{1-4}$ alkyl, $C_{1-6}$ alkoxyl or $C_6$-$C_{10}$ aryloxy, each optionally substituted with one or more halo;

each of $R^{704}$ and $R^{705}$, independently is $C_{1-4}$ alkyl;

$R^{706}$ is cyclohexyl substituted by $N(C_{1-4}$ alkyl$)_2$ wherein one or both of the $C_{1-4}$ alkyl is substituted with $C_{1-6}$ alkoxy; or $R^{706}$ is tetrahydropyranyl;

$R^{707}$ is $C_{1-4}$ alkyl optionally substituted with one or more groups selected from hydroxyl, $C_{1-4}$ alkoxy, amino, mono- or di-$C_{1-4}$ alkylamino, $C_{3-8}$ cycloalkyl, and 4-7 membered heterocycloalkyl containing 1-3 heteroatoms, wherein the $C_{3-8}$ cycloalkyl or 4-7 membered heterocycloalkyl each independently is further optionally substituted with $C_{1-3}$ alkyl;

$R^{708}$ is $C_{1-4}$ alkyl optionally substituted with one or more groups selected from OH, halo, and $C_{1-4}$ alkoxy, 4-7 membered heterocycloalkyl containing 1-3 heteroatoms, or O—$C_{1-6}$ alkyl, wherein the 4-7 membered heterocycloalkyl can be optionally further substituted with OH or $C_{1-6}$ alkyl; and $n_7$ is 0, 1 or 2.

For example, $R^{706}$ is cyclohexyl substituted by $N(C_{1-4}$ alkyl$)_2$ wherein one of the $C_{1-4}$ alkyl is unsubstituted and the other is substituted with methoxy.

For example, $R^{706}$ is

For example, the compound is of Formula II:

(II)

For example, $R^{702}$ is methyl or isopropyl and $R^{703}$ is methyl or methoxyl.

For example, $R^{704}$ is methyl.

For example, $R^{701}$ is $OR^{707}$ and $R^{707}$ is $C_{1-3}$ alkyl optionally substituted with $OCH_3$ or morpholine.

For example, $R^{701}$ is H or F.

For example, $R^{701}$ is tetrahydropyranyl, phenyl, pyridyl, pyrimidyl, pyrazinyl, imidazolyl, or pyrazolyl, each of which is optionally substituted with methyl, methoxy, ethyl substituted with morpholine, or —$OCH_2CH_2OCH_3$.

For example, $R^{708}$ is morpholine, piperidine, piperazine, pyrrolidine, diazepane, or azetidine, each of which is optionally substituted with OH or $C_{1-6}$ alkyl.

For example, $R^{708}$ is morpholine

For example, $R^{708}$ is piperazine substituted with $C_{1-6}$ alkyl.

For example, $R^{708}$ is methyl, t-butyl or $C(CH_3)_2OH$.

A compound (i.e., an EZH2 inhibitor) that can be used in any methods described herein may have the following Formula III:

or a pharmaceutically acceptable salt thereof.

In this formula:

$R^{801}$ is $C_{1-6}$ alkyl, $C_{2-6}$ alkenyl, $C_{2-6}$ alkynyl, $C_{3-8}$ cycloalkyl, 4-7 membered heterocycloalkyl containing 1-3 heteroatoms, phenyl or 5- or 6-membered heteroaryl, each of which is substituted with O—$C_{1-6}$ alkyl-$R_x$ or NH—$C_{1-6}$ alkyl-$R_x$, wherein $R_x$ is hydroxyl, O—$C_{1-3}$ alkyl or NH—$C_{1-3}$ alkyl, and $R_x$ is optionally further substituted with O—$C_{1-3}$ alkyl or NH—$C_{1-3}$ alkyl except when $R_x$ is hydroxyl; or $R^{801}$ is phenyl substituted with -$Q_2$-$T_2$, wherein $Q_2$ is a bond or $C_1$-$C_3$ alkyl linker optionally substituted with halo, cyano, hydroxyl or $C_1$-$C_6$ alkoxy, and $T_2$ is optionally substituted 4- to 12-membered heterocycloalkyl; and $R^{801}$ is optionally further substituted;

each of $R^{802}$ and $R^{803}$, independently is H, halo, $C_{1-4}$ alkyl, $C_{1-6}$ alkoxyl or $C_6$-$C_{10}$ aryloxy, each optionally substituted with one or more halo;

each of $R^{804}$ and $R^{805}$, independently is $C_{1-4}$ alkyl; and $R^{806}$ is -$Q_x$-$T_x$, wherein $Q_x$ is a bond or $C_{1-4}$ alkyl linker, $T_x$ is H, optionally substituted $C_{1-4}$ alkyl, optionally substituted $C_3$-$C_8$ cycloalkyl or optionally substituted 4- to 14-membered heterocycloalkyl.

For example, each of $Q_x$ and $Q_2$ independently is a bond or methyl linker, and each of $T_x$ and $T_2$ independently is tetrahydropyranyl, piperidinyl substituted by 1, 2, or 3 $C_{1-4}$ alkyl groups, or cyclohexyl substituted by N($C_{1-4}$ alkyl)$_2$ wherein one or both of the $C_{1-4}$ alkyl is optionally substituted with $C_{1-6}$ alkoxy;

For example, $R^{806}$ is cyclohexyl substituted by N($C_{1-4}$ alkyl)$_2$ or $R^{806}$ is tetrahydropyranyl.

For example, $R^{806}$ is

For example, $R^{801}$ is phenyl or 5- or 6-membered heteroaryl substituted with O—$C_{1-6}$ alkyl-$R_x$, or $R^{801}$ is phenyl substituted with CH$_2$-tetrahydropyranyl.

For example, a compound of the present invention is of Formula IVa or IVb:

wherein Z' is CH or N, and $R^{807}$ is $C_{2-3}$ alkyl-$R_x$.

For example, $R^{807}$ is —CH$_2$CH$_2$OH, —CH$_2$CH$_2$OCH$_3$, or —CH$_2$CH$_2$OCH$_2$CH$_2$OCH$_3$.

For example, $R^{802}$ is methyl or isopropyl and $R^{803}$ is methyl or methoxyl.

For example, $R^{804}$ is methyl.

A compound of the present invention may have the following Formula (V):

or a pharmaceutically acceptable salt or ester thereof.

In this formula:

$R_2$, $R_4$ and $R_{12}$ are each, independently $C_{1-6}$ alkyl;

$R_6$ is $C_6$-$C_{10}$ aryl or 5- or 6-membered heteroaryl, each of which is optionally substituted with one or more -$Q_2$-$T_2$, wherein $Q_2$ is a bond or $C_1$-$C_3$ alkyl linker optionally substituted with halo, cyano, hydroxyl or $C_1$-$C_6$ alkoxy, and $T_2$ is H, halo, cyano, —$OR_a$, —$NR_aR_b$, —$(NR_aR_bR_c)^+A^-$, —$C(O)R_a$, —$C(O)OR_a$, —$C(O)NR_aR_b$, —$NR_bC(O)R_a$, —$NR_bC(O)OR_a$, —$S(O)_2R_a$, —$S(O)_2NR_aR_b$, or $R_{S2}$, in which each of $R_a$, $R_b$, and $R_c$, independently is H or $R_{S3}$, $A^-$ is a pharmaceutically acceptable anion, each of $R_{S2}$ and $R_{S3}$, independently, is $C_1$-$C_6$ alkyl, $C_3$-$C_8$ cycloalkyl, $C_6$-$C_{10}$ aryl, 4 to 12-membered heterocycloalkyl, or 5- or 6-membered heteroaryl, or $R_a$ and $R_b$, together with the N atom to which they are attached, form a 4 to 12-membered heterocycloalkyl ring having 0 or 1 additional heteroatom, and each of $R_{S2}$, $R_{S3}$, and the 4 to 12-membered heterocycloalkyl ring formed by $R_a$ and $R_b$, is optionally substituted with one or more -$Q_3$-$T_3$, wherein $Q_3$ is a bond or $C_1$-$C_3$ alkyl linker each optionally substituted with halo, cyano, hydroxyl or $C_1$-$C_6$ alkoxy, and $T_3$ is selected from the group consisting of halo, cyano, $C_1$-$C_6$ alkyl, $C_3$-$C_8$ cycloalkyl, $C_6$-$C_{10}$ aryl, 4 to 12-membered heterocycloalkyl, 5- or 6-membered heteroaryl, $OR_d$, $COOR_d$, —$S(O)_2R_d$, —$NR_dR_e$, and —$C(O)NR_dR_e$, each of $R_d$ and $R_e$ independently being H or $C_1$-$C_6$ alkyl, or -$Q_3$-$T_3$ is oxo; or any two neighboring -$Q_2$-$T_2$, together with the atoms to which they are attached form a 5- or 6-membered ring optionally containing 1-4 heteroatoms selected from N, O and S and optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl;

$R^7$ is -$Q_4$-$T_4$, in which $Q_4$ is a bond, $C_1$-$C_4$ alkyl linker, or $C_2$-$C_4$ alkenyl linker, each linker optionally substituted with halo, cyano, hydroxyl or $C_1$-$C_6$ alkoxy, and $T_4$ is H, halo, cyano, $NR_fR_g$, —$OR_f$, —$C(O)R_f$, —$C(O)OR_f$, —$C(O)NR_fR_g$, —$C(O)NR_fOR_g$, —$NR_fC(O)R_g$, —$S(O)_2R_f$, or $R_{S4}$, in which each of $R_f$ and $R_g$, independently is H or $R_{S5}$, each of $R_{S4}$ and $R_{S5}$, independently is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl, and each of $R_{S4}$ and $R_{S5}$ is optionally substituted with one or more -$Q_5$-$T_5$, wherein $Q_5$ is a bond, C(O), C(O)$NR_k$, $NR_k$C(O), $S(O)_2$, or $C_1$-$C_3$ alkyl linker, $R_k$ being H or $C_1$-$C_6$ alkyl, and $T_5$ is H, halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, 5- or 6-membered heteroaryl, or $S(O)_qR_q$ in which q is 0, 1, or 2 and $R_q$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl, and $T_5$ is optionally substituted with one or more substituents selected from the group consisting of halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl except when $T_5$ is H, halo, hydroxyl, or cyano; or -$Q_5$-$T_5$ is oxo; and $R_8$ is H, halo, hydroxyl, COOH, cyano, $R_{S6}$, $OR_{S6}$, or $COOR_{S6}$, in which $R_{S6}$ is $C_1$-$C_6$ alkyl, $C_2$-$C_6$ alkenyl, $C_2$-$C_6$ alkynyl, $C_3$-$C_8$ cycloalkyl, 4 to 12-membered heterocycloalkyl, amino, mono-$C_1$-$C_6$ alkylamino, or di-$C_1$-$C_6$ alkylamino, and $R_{S6}$ is optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, and di-$C_1$-$C_6$ alkylamino; or $R^7$ and $R_8$, together with the N atom to which they are attached, form a 4 to 11-membered heterocycloalkyl ring having 0 to 2 additional heteroatoms, and the 4 to 11-membered heterocycloalkyl ring formed by $R^7$ and $R_8$ is optionally substituted with one or more -$Q_6$-$T_6$, wherein $Q_6$ is a bond, C(O), C(O)$NR_m$, $NR_m$C(O), $S(O)_2$, or $C_1$-$C_3$ alkyl linker, $R_m$ being H or $C_1$-$C_6$ alkyl, and $T_6$ is H, halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, 5- or 6-membered heteroaryl, or $S(O)_pR_p$ in which p is 0, 1, or 2 and $R_p$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl, and $T_6$ is optionally substituted with one or more substituents selected from the group consisting of halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl except when $T_6$ is H, halo, hydroxyl, or cyano; or -$Q_6$-$T_6$ is oxo.

For example, $R^6$ is $C_6$-$C_{10}$ aryl or 5- or 6-membered heteroaryl, each of which is optionally, independently substituted with one or more -$Q_2$-$T_2$, wherein $Q_2$ is a bond or $C_1$-$C_3$ alkyl linker, and $T_2$ is H, halo, cyano, —$OR_a$, —$NR_aR_b$, —$(NR_aR_bR_c)^+A^-$, —$C(O)NR_aR_b$, —$NR_bC(O)R_a$, —$S(O)_2R_a$, or $R_{S2}$, in which each of $R_a$ and $R_b$, independently is H or $R_{S3}$, each of $R_{S2}$ and $R_{S3}$, independently, is $C_1$-$C_6$ alkyl, or $R_a$ and $R_b$, together with the N atom to which they are attached, form a 4 to 7-membered heterocycloalkyl ring having 0 or 1 additional heteroatom, and each of $R_{S2}$, $R_{S3}$, and the 4 to 7-membered heterocycloalkyl ring formed by $R_a$ and $R_b$, is optionally, independently substituted with one or more -$Q_3$-$T_3$, wherein $Q_3$ is a bond or $C_1$-$C_3$ alkyl linker and $T_3$ is selected from the group consisting of halo, $C_1$-$C_6$ alkyl, 4 to 7-membered heterocycloalkyl, $OR_d$, —$S(O)_2R_d$, and —$NR_dR_e$, each of $R_d$ and $R_e$ independently being H or $C_1$-$C_6$ alkyl, or -$Q_3$-$T_3$ is oxo; or any two neighboring -$Q_2$-$T_2$, together with the atoms to which they are attached form a 5- or 6-membered ring optionally containing 1-4 heteroatoms selected from N, O and S.

For example, the compound of the present invention is of Formula (VI):

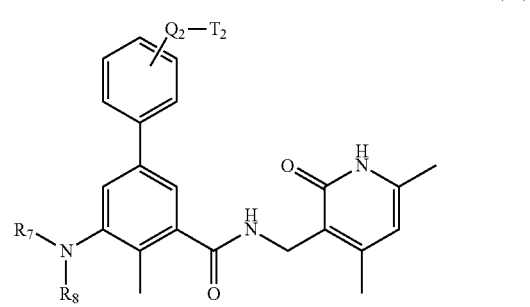

(VI)

or a pharmaceutically acceptable salt thereof, wherein $Q_2$ is a bond or methyl linker, $T_2$ is H, halo, —$OR_a$, —$NR_aR_b$, —$(NR_aR_bR_c)^+A^-$, or —$S(O)_2NR_aR_b$, $R^7$ is piperidinyl, tetrahydropyran, cyclopentyl, or cyclohexyl, each optionally substituted with one -$Q_5$-$T_5$ and $R_8$ is ethyl.

A compound of the present invention may have the following Formula (VIa):

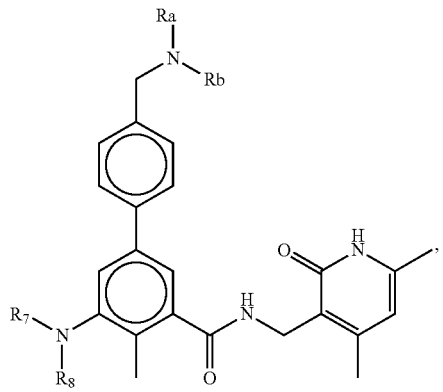

wherein each of $R_a$ and $R_b$, independently is H or $R_{S3}$, $R_{S3}$ being $C_1$-$C_6$ alkyl, $C_3$-$C_8$ cycloalkyl, $C_6$-$C_{10}$ aryl, 4 to 12-membered heterocycloalkyl, or 5- or 6-membered heteroaryl, or $R_a$ and $R_b$, together with the N atom to which they are attached, form a 4 to 12-membered heterocycloalkyl ring having 0 or 1 additional heteroatom, and each of $R_{S3}$ and the 4 to 12-membered heterocycloalkyl ring formed by $R_a$ and $R_b$, is optionally substituted with one or more -$Q_3$-$T_3$, wherein $Q_3$ is a bond or $C_1$-$C_3$ alkyl linker each optionally substituted with halo, cyano, hydroxyl or $C_1$-$C_6$ alkoxy, and $T_3$ is selected from the group consisting of halo, cyano, $C_1$-$C_6$ alkyl, $C_3$-$C_8$ cycloalkyl, $C_6$-$C_{10}$ aryl, 4 to 12-membered heterocycloalkyl, 5- or 6-membered heteroaryl, $OR_d$, $COOR_d$, —$S(O)_2R_d$, —$NR_dR_e$, and —$C(O)NR_dR_e$, each of $R_d$ and $R_e$ independently being H or $C_1$-$C_6$ alkyl, or -$Q_3$-$T_3$ is oxo;

$R^7$ is -$Q_4$-$T_4$, in which $Q_4$ is a bond, $C_1$-$C_4$ alkyl linker, or $C_2$-$C_4$ alkenyl linker, each linker optionally substituted with halo, cyano, hydroxyl or $C_1$-$C_6$ alkoxy, and $T_4$ is H, halo, cyano, $NR_fR_g$, —$OR_f$, —$C(O)R_f$, —$C(O)OR_f$, —$C(O)NR_fR_g$, —$C(O)NR_fOR_g$, —$NR_fC(O)R_g$, —$S(O)_2R_f$, or $R_{S4}$, in which each of $R_f$ and $R_g$, independently is H or $R_{S5}$, each of $R_{S4}$ and $R_{S5}$, independently is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 7-membered heterocycloalkyl, or 5- or 6-membered heteroaryl, and each of $R_{S4}$ and $R_{S5}$ is optionally substituted with one or more -$Q_5$-$T_5$, wherein $Q_5$ is a bond, C(O), C(O)$NR_k$, $NR_k$C(O), S(O)$_2$, or $C_1$-$C_3$ alkyl linker, $R_k$ being H or $C_1$-$C_6$ alkyl, and $T_5$ is H, halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 7-membered heterocycloalkyl, 5- or 6-membered heteroaryl, or $S(O)_qR_q$ in which q is 0, 1, or 2 and $R_q$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 7-membered heterocycloalkyl, or 5- or 6-membered heteroaryl, and $T_5$ is optionally substituted with one or more substituents selected from the group consisting of halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 7-membered heterocycloalkyl, and 5- or 6-membered heteroaryl except when $T_5$ is H, halo, hydroxyl, or cyano; or -$Q_5$-$T_5$ is oxo; provided that $R^7$ is not H; and $R_8$ is H, halo, hydroxyl, COOH, cyano, $R_{S6}$, $OR_{S6}$, or $COOR_{S6}$, in which $R_{S6}$ is $C_1$-$C_6$ alkyl, $C_2$-$C_6$ alkenyl, $C_2$-$C_6$ alkynyl, amino, mono-$C_1$-$C_6$ alkylamino, or di-$C_1$-$C_6$ alkylamino, and $R_{S6}$ is optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, and di-$C_1$-$C_6$ alkylamino; or $R_7$ and $R_8$, together with the N atom to which they are attached, form a 4 to 11-membered heterocycloalkyl ring which has 0 to 2 additional heteroatoms and is optionally substituted with one or more -$Q_6$-$T_6$, wherein $Q_6$ is a bond, C(O), C(O)$NR_m$, $NR_m$C(O), $S(O)_2$, or $C_1$-$C_3$ alkyl linker, $R_m$ being H or $C_1$-$C_6$ alkyl, and $T_6$ is H, halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 7-membered heterocycloalkyl, 5- or 6-membered heteroaryl, or $S(O)_pR_p$ in which p is 0, 1, or 2 and $R_p$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 7-membered heterocycloalkyl, or 5- or 6-membered heteroaryl, and $T_6$ is optionally substituted with one or more substituents selected from the group consisting of halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 7-membered heterocycloalkyl, and 5- or 6-membered heteroaryl except when $T_6$ is H, halo, hydroxyl, or cyano; or -$Q_6$-$T_6$ is oxo.

For example, $R_a$ and $R_b$, together with the N atom to which they are attached, form a 4 to 7-membered heterocycloalkyl ring having 0 or 1 additional heteroatoms to the N atom and the ring is optionally substituted with one or more -$Q_3$-$T_3$, wherein the heterocycloalkyl is azetidinyl, pyrrolidinyl, imidazolidinyl, pyrazolidinyl, oxazolidinyl, isoxazolidinyl, triazolidinyl, piperidinyl, 1,2,3,6-tetrahydropyridinyl, piperazinyl, or morpholinyl.

For example, $R_7$ is $C_3$-$C_8$ cycloalkyl or 4 to 7-membered heterocycloalkyl, each optionally substituted with one or more -$Q_5$-$T_5$.

For example, $R_7$ is piperidinyl, tetrahydropyran, tetrahydro-2H-thiopyranyl, cyclopentyl, cyclohexyl, pyrrolidinyl, or cycloheptyl, each optionally substituted with one or more -$Q_5$-$T_5$.

For example, $R_8$ is H or $C_1$-$C_6$ alkyl which is optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, and di-$C_1$-$C_6$ alkylamino.

In embodiments, a compound that can be used in any methods presented here is:

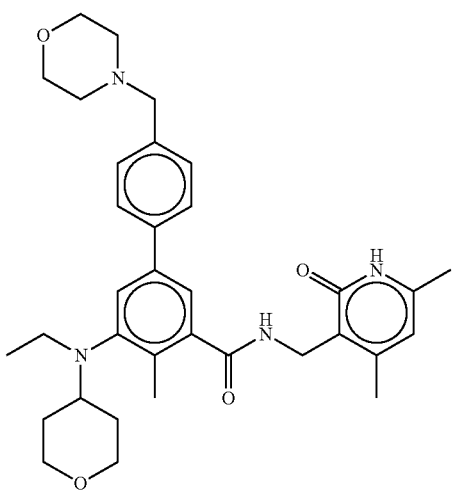

(Compound A, also referred to herein as E7438 or EPZ-6438)

(Compound A, also referred to herein as E7438 or EPZ-6438) or pharmaceutically acceptable salt thereof.

In embodiments, a compound that can be used in any methods presented here is:

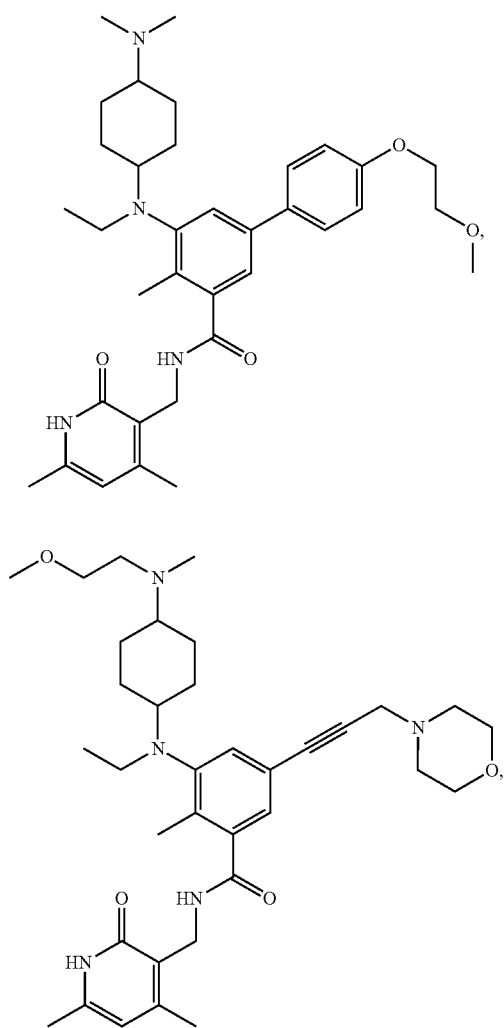

(B)

(C)

(D)

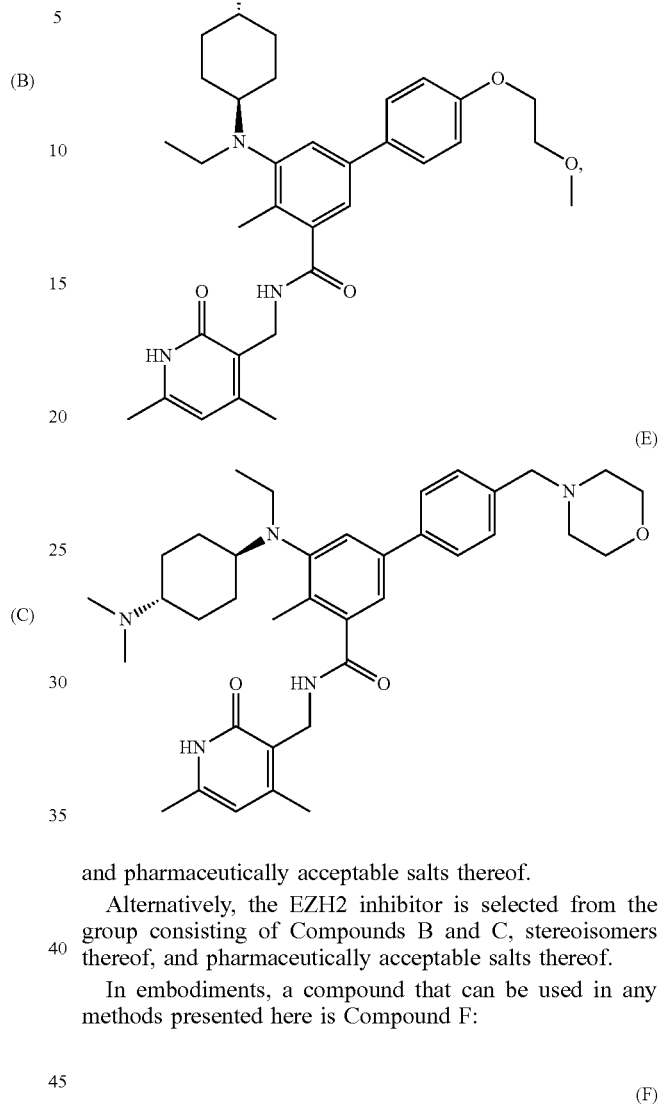

(B')

(E)

and pharmaceutically acceptable salts thereof.

Alternatively, the EZH2 inhibitor is selected from the group consisting of Compounds B and C, stereoisomers thereof, and pharmaceutically acceptable salts thereof.

In embodiments, a compound that can be used in any methods presented here is Compound F:

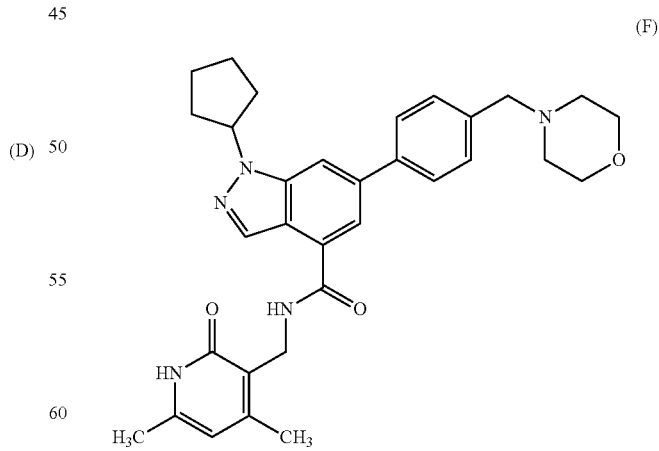

(F)

or pharmaceutically acceptable salts thereof.

In embodiments, the compounds suitable for use in the method of this invention include compounds of Formula (VII):

(VII)

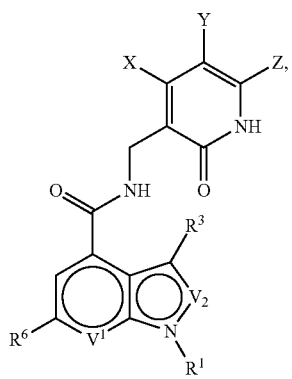

wherein,

V¹ is N or CR⁷,

V² is N or CR², provided when V¹ is N, V² is N,

X and Z are selected independently from the group consisting of hydrogen, (C₁-C₈)alkyl, (C₂-C₈)alkenyl, (C₂-C₈)alkynyl, unsubstituted or substituted (C₃-C₈)cycloalkyl, unsubstituted or substituted (C₃-C₈)cycloalkyl-(C₁-C₈)alkyl or —(C₂-C₈)alkenyl, unsubstituted or substituted (C₅-C₈) cycloalkenyl, unsubstituted or substituted (C₅-C₈)cycloalkenyl-(C₁-C₈)alkyl or —(C₂-C₈)alkenyl, (C₆-C₁₀)bicycloalkyl, unsubstituted or substituted heterocycloalkyl, unsubstituted or substituted heterocycloalkyl-(C₁-C₈)alkyl or —(C₂-C₈)alkenyl, unsubstituted or substituted aryl, unsubstituted or substituted aryl-(C₁-C₈)alkyl or —(C₂-C₈) alkenyl, unsubstituted or substituted heteroaryl, unsubstituted or substituted heteroaryl-(C₁-C₈)alkyl or —(C₂-C₈) alkenyl, halo, cyano, —COR$^a$, —CO₂R$^a$, —CONR$^a$R$^b$, —CONR$^a$NR$^a$R$^b$, —SR$^a$, —SOR$^a$, —SO₂R$^a$, —SO₂NR$^a$R$^b$, nitro, —NR$^a$R$^b$, —NR$^a$C(O)R$^b$, —NR$^a$C(O) NR$^a$R$^b$, —NR$^a$C(O)OR$^a$, —NR$^a$SO₂R$^b$, —NR$^a$SO₂NR$^a$R$^b$, —NR$^a$NR$^a$R$^b$, —NR$^a$NR$^a$C(O)R$^b$, —NR$^a$NR$^a$C(O)NR$^a$R$^b$, —NR$^a$NR$^a$C(O)ORa, —OR$^a$, —OC(O)R$^a$, and —OC(O) NR$^a$R$^b$;

Y is H or halo;

R¹ is (C₁-C₈)alkyl, (C₂-C₈)alkenyl, (C₂-C₈)alkynyl, unsubstituted or substituted (C₃-C₈)cycloalkyl, unsubstituted or substituted (C₃-C₈)cycloalkyl-(C₁-C₈)alkyl or —(C₂-C₈)alkenyl, unsubstituted or substituted (C₅-C₈)cycloalkenyl, unsubstituted or substituted (C₅-C₈)cycloalkenyl-(C₁-C₈)alkyl or —(C₂-C₈)alkenyl, unsubstituted or substituted (C₆-C₁₀)bicycloalkyl, unsubstituted or substituted heterocycloalkyl or —(C₂-C₈)alkenyl, unsubstituted or substituted heterocycloalkyl-(C₁-C₈)alkyl, unsubstituted or substituted aryl, unsubstituted or substituted aryl-(C₁-C₈) alkyl or —(C₂-C₈)alkenyl, unsubstituted or substituted heteroaryl, unsubstituted or substituted heteroaryl-(C₁-C₈)alkyl or —(C₂-C₈)alkenyl, —COR$^a$, —CO₂R$^a$, —CONR$^a$R$^b$, —CONR$^a$NR$^a$R$^b$;

R² is hydrogen, (C₁-C₈)alkyl, trifluoromethyl, alkoxy, or halo, in which said (C₁-C₈)alkyl is optionally substituted with one to two groups selected from amino and (C₁-C₃) alkylamino;

R⁷ is hydrogen, (C₁-C₃)alkyl, or alkoxy;

R³ is hydrogen, (C₁-C₈)alkyl, cyano, trifluoromethyl, —NR$^a$R$^b$, or halo;

R⁶ is selected from the group consisting of hydrogen, halo, (C₁-C₈)alkyl, (C₂-C₈)alkenyl, (C₂-C₈)alkynyl, unsubstituted or substituted (C₃-C₈)cycloalkyl, unsubstituted or substituted (C₃-C₈)cycloalkyl-(C₁-C₈)alkyl, unsubstituted or substituted (C₅-C₈)cycloalkenyl, unsubstituted or substituted (C₅-C₈)cycloalkenyl-(C₁-C₈)alkyl, (C₆-C₁₀)bicycloalkyl, unsubstituted or substituted heterocycloalkyl, unsubstituted or substituted heterocycloalkyl-(C₁-C₈)alkyl, unsubstituted or substituted aryl, unsubstituted or substituted aryl-(C₁-C₈)alkyl, unsubstituted or substituted heteroaryl, unsubstituted or substituted heteroaryl-(C₁-C₈)alkyl, cyano, —COR$^a$, —CO₂R$^a$, CONR$^a$R$^b$, —CONR$^a$NR$^a$R$^b$, —SR$^a$, —SOR$^a$, —SO₂R$^a$, —SO₂NR$^a$R$^b$, nitro, —NR$^a$R$^b$, —NR$^a$C (O)R$^b$, —NR$^a$C(O)NR$^a$R$^b$, —NR$^a$C(O)OR$^a$, —NR$^a$SO₂R$^b$, —NR$^a$SO₂NR$^a$R$^b$, —NR$^a$NR$^a$R$^b$, —NR$^a$NR$^a$C(O)R$^b$, —NR$^a$NR$^a$C(O)NR$^a$R$^b$, —NR$^a$NR$^a$C(O)OR$^a$, —OR$^a$, —OC(O)R$^a$, —OC(O)NR$^a$R$^b$;

wherein any (C₁-C₈)alkyl, (C₂-C₈)alkenyl, (C₂-C₈)alkynyl, cycloalkyl, cycloalkenyl, bicycloalkyl, heterocycloalkyl, aryl, or heteroaryl group is optionally substituted by 1, 2 or 3 groups independently selected from the group consisting of —O(C₁-C₆)alkyl(R$^c$)₁₋₂, —S(C₁-C₆)alkyl (R$^c$)₁₋₂, —(C₁-C₆)alkyl(R$^c$)₁₋₂, —(C₁-C₈)alkyl-heterocycloalkyl, (C₃-C₈)cycloalkyl-heterocycloalkyl, halo, (C₁-C₆) alkyl, (C₃-C₈)cycloalkyl, (C₅-C₈)cycloalkenyl, (C₁-C₆)haloalkyl, cyano, —COR$^a$, —CO₂R$^a$, —CONR$^a$R$^b$, —SR$^a$, —SOR$^a$, —SO₂R$^a$, —SO₂NR$^a$R$^b$, nitro, —NR$^a$R$^b$, —NR$^a$C (O)R$^b$, —NR$^a$C(O)NR$^a$R$^b$, —NR$^a$C(O)OR$^a$, —NR$^a$SO₂R$^b$, —NR$^a$SO₂NR$^a$R$^b$, —OR$^a$, —OC(O)R$^a$, OC(O)NR$^a$R$^b$, heterocycloalkyl, aryl, heteroaryl, aryl(C₁-C₄)alkyl, and heteroaryl(C₁-C₄)alkyl;

wherein any aryl or heteroaryl moiety of said aryl, heteroaryl, aryl(C₁-C₄)alkyl, or heteroaryl(C₁-C₄)alkyl is optionally substituted by 1, 2 or 3 groups independently selected from the group consisting of halo, (C₁-C₆) alkyl, (C₃-C₈)cycloalkyl, (C₅-C₈)cycloalkenyl, (C₁-C₆) haloalkyl, cyano, —COR$^a$, —CO₂R$^a$, —CONR$^a$R$^b$, —SR$^a$, —SOR$^a$, —SO₂R$^a$, —SO₂NR$^a$R$^b$, nitro, —NR$^a$R$^b$, —NR$^a$C(O)R$^b$, —NR$^a$C(O)NR$^a$R$^b$, —NR$^a$C(O)OR$^a$, —NR$^a$SO₂R$^b$, —NR$^a$SO₂NR$^a$R$^b$, —OR$^a$, —OC(O)R$^a$, and —OC(O)NR$^a$R$^b$;

R$^a$ and R$^b$ are each independently hydrogen, (C₁-C₈)alkyl, (C₂-C₈)alkenyl, (C₂-C₈)alkynyl, (C₃-C₈)cycloalkyl, (C₅-C₈) cycloalkenyl, (C₆-C₁₀)bicycloalkyl, heterocycloalkyl, aryl, or heteroaryl, wherein said (C₁-C₈)alkyl, (C₂-C₈)alkenyl, (C₂-C₈)alkynyl, cycloalkyl, cycloalkenyl, bicycloalkyl, heterocycloalkyl, aryl or heteroaryl group is optionally substituted by 1, 2 or 3 groups independently selected from halo, hydroxyl, (C₁-C₄)alkoxy, amino, (C₁-C₄)alkylamino, ((C₁-C₄)alkyl)((C₁-C₄)alkyl)amino, —CO₂H, —CO₂(C₁-C₄) alkyl, —CONH₂, —CONH(C₁-C₄)alkyl, —CON((C₁-C₄) alkyl)((C₁-C₄)alkyl), —SO₂(C₁-C₄)alkyl, —SO₂NH₂, —SO₂NH(C₁-C₄)alkyl, and SO₂N((C₁-C₄)alkyl)((C₁-C₄) alkyl);

or R$^a$ and R$^b$ taken together with the nitrogen to which they are attached represent a 5-8 membered saturated or unsaturated ring, optionally containing an additional heteroatom selected from oxygen, nitrogen, and sulfur, wherein said ring is optionally substituted by 1, 2 or 3 groups independently selected from (C₁-C₄)alkyl, (C₁-C₄)haloalkyl, amino, (C₁-C₄)alkylamino, ((C₁-C₄)alkyl)((C₁-C₄) alkyl)amino, hydroxyl, oxo, (C₁-C₄)alkoxy, and (C₁-C₄) alkoxy(C₁-C₄)alkyl, wherein said ring is optionally fused to a (C₃-C₈)cycloalkyl, heterocycloalkyl, aryl, or heteroaryl ring;

or R$^a$ and R$^b$ taken together with the nitrogen to which they are attached represent a 6- to 10-membered bridged bicyclic ring system optionally fused to a (C₃-C₈)cycloalkyl, heterocycloalkyl, aryl, or heteroaryl ring;

each $R_c$ is independently $(C_1-C_4)$alkylamino, —$NR^aSO_2R^b$, —$SOR^a$, —$SO_2R^a$, —$NR^aC(O)OR^a$, —$NR^aR^b$, or —$CO_2R^a$;

or a salt thereof.

Subgroups of the compounds encompassed by the general structure of Formula (I) are represented as follows:

Subgroup A of Formula (VII)

X and Z are selected from the group consisting of $(C_1-C_8)$alkyl, $(C_3-C_8)$cycloalkyl, heterocycloalkyl, aryl, heteroaryl, —$NR^aR^b$, and —$OR^a$;

Y is H or F;

$R^1$ is selected from the group consisting of $(C_1-C_8)$alkyl, $(C_3-C_8)$cycloalkyl, heterocycloalkyl, aryl, and heteroaryl;

$R^2$ is hydrogen, $(C_1-C_8)$alkyl, trifluoromethyl, alkoxy, or halo, in which said $(C_1-C_8)$alkyl is optionally substituted with one to two groups selected from amino and $(C_1-C_3)$alkylamino;

$R^7$ is hydrogen, $(C_1-C_3)$alkyl, or alkoxy;

$R^3$ is selected from the group consisting of hydrogen, $(C_1-C_8)$alkyl, cyano, trifluoromethyl, —$NR^aR^b$, and halo;

$R^6$ is selected from the group consisting of hydrogen, halo, cyano, trifluoromethyl, amino, $(C_1-C_8)$alkyl, $(C_3-C_8)$cycloalkyl, aryl, heteroaryl, acylamino, $(C_2-C_8)$alkynyl, arylalkynyl, heteroarylalkynyl, —$SO_2R^a$, —$SO_2NR^aR^b$ and —$NR^aSO_2R^b$;

wherein any $(C_1-C_8)$alkyl, $(C_3-C_8)$cycloalkyl, $(C_2-C_8)$alkynyl, arylalkynyl, heteroarylalkynyl group is optionally substituted by 1, 2 or 3 groups independently selected from —$O(C_1-C_6)$alkyl$(R^c)_{1-2}$, —$S(C_1-C_6)$alkyl$(R^c)_{1-2}$, —$(C_1-C_6)$alkyl$(R^c)_{1-2}$, —$(C_1-C_8)$alkyl-heterocycloalkyl, $(C_3-C_8)$cycloalkyl-heterocycloalkyl, halo, $(C_1-C_6)$alkyl, $(C_3-C_8)$cycloalkyl, $(C_5-C_8)$cycloalkenyl, $(C_1-C_6)$haloalkyl, cyano, —$COR^a$, —$CO_2R^a$, —$CONR^aR^b$, —$SR^a$, —$SOR^a$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, —$NR^aSO_2R^b$, —$NR^aSO_2NR^aR^b$, —$OR^a$, —$OC(O)R^a$, —$OC(O)NR^aR^b$, heterocycloalkyl, aryl, heteroaryl, aryl$(C_1-C_4)$alkyl, and heteroaryl$(C_1-C_4)$alkyl;

$R^a$ and $R^b$ are each independently hydrogen, $(C_1-C_8)$alkyl, $(C_2-C_8)$alkenyl, $(C_2-C_8)$alkynyl, $(C_3-C_8)$cycloalkyl, $(C_5-C_8)$cycloalkenyl, $(C_6-C_{10})$bicycloalkyl, heterocycloalkyl, aryl, or heteroaryl, wherein said $(C_1-C_8)$alkyl, $(C_2-C_8)$alkenyl, $(C_2-C_8)$alkynyl, cycloalkyl, cycloalkenyl, bicycloalkyl, heterocycloalkyl, aryl or heteroaryl group is optionally substituted by 1, 2 or 3 groups independently selected from halo, hydroxyl, $(C_1-C_4)$alkoxy, amino, $(C_1-C_4)$alkylamino, $((C_1-C_4)$alkyl$)((C_1-C_4)$alkyl$)$amino, —$CO_2H$, —$CO_2(C_1-C_4)$alkyl, —$CONH_2$, —$CONH(C_1-C_4)$alkyl, —$CON((C_1-C_4)$alkyl$)((C_1-C_4)$alkyl$)$, —$SO_2(C_1-C_4)$alkyl, —$SO_2NH_2$, —$SO_2NH(C_1-C_4)$alkyl, and —$SO_2N((C_1-C_4)$alkyl$)((C_1-C_4)$alkyl$)$;

or $R^a$ and $R^b$ taken together with the nitrogen to which they are attached represent a 5-8 membered saturated or unsaturated ring, optionally containing an additional heteroatom selected from oxygen, nitrogen, and sulfur, wherein said ring is optionally substituted by 1, 2 or 3 groups independently selected from $(C_1-C_4)$alkyl, $(C_1-C_4)$haloalkyl, amino, $(C_1-C_4)$alkylamino, $((C_1-C_4)$alkyl$)((C_1-C_4)$alkyl$)$amino, hydroxyl, oxo, $(C_1-C_4)$alkoxy, and $(C_1-C_4)$alkoxy$(C_1-C_4)$alkyl, wherein said ring is optionally fused to a $(C_3-C_8)$cycloalkyl, heterocycloalkyl, aryl, or heteroaryl ring;

or $R^a$ and $R^b$ taken together with the nitrogen to which they are attached represent a 6- to 10-membered bridged bicyclic ring system optionally fused to a $(C_3-C_8)$cycloalkyl, heterocycloalkyl, aryl, or heteroaryl ring. An aryl or heteroaryl group in this particular subgroup A is selected independently from the group consisting of furan, thiophene, pyrrole, oxazole, thiazole, imidazole, pyrazole, oxadiazole, thiadiazole, triazole, tetrazole, benzofuran, benzothiophene, benzoxazole, benzothiazole, phenyl, pyridine, pyridazine, pyrimidine, pyrazine, triazine, tetrazine, quinoline, cinnoline, quinazoline, quinoxaline, and naphthyridine or another aryl or heteroaryl group as follows:

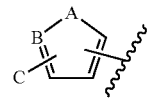
(1)

wherein in (1),
A is O, NH, or S; B is CH or N, and C is hydrogen or $C_1-C_8$ alkyl; or

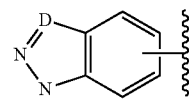
(2)

wherein in (2),
D is N or C optionally substituted by hydrogen or $C_1-C_8$ alkyl; or

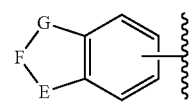
(3)

wherein in (3),
E is NH or $CH_2$; F is O or CO; and G is NH or $CH_2$; or

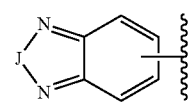
(4)

wherein in (4),
J is O, S or CO; or

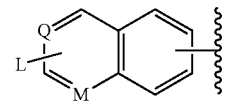
(5)

wherein in (5),
Q is CH or N;
M is CH or N; and
L/(5) is hydrogen, halo, amino, cyano, $(C_1-C_8)$alkyl, $(C_3-C_8)$cycloalkyl, —$COR^a$, —$CO_2R^a$, —$CONR^aR^b$, —$CONR^aNR^aR^b$, —$SO_2R^a$, —$SO_2NR^aR^b$, —$NR^aR^b$, —$NR^aC(O)R^b$, —$NR^aSO_2R^b$, —$NR^aSO_2NR^aR^b$, —$NR^aNR^aR^b$, —$NR^aNR^aC(O)R^b$, —$NR^aNR^aC(O)NR^aR^b$, or —$OR^a$, wherein any $(C_1-C_8)$alkyl or $(C_3-C_8)$cycloalkyl group is optionally substituted by 1, 2 or 3 groups independently selected from $(C_1-C_6)$alkyl, $(C_3-C_8)$cycloalkyl, $(C_5-C_8)$cycloalkenyl, $(C_1-C_6)$haloalkyl, cyano, —$COR^a$, —$CO_2R^a$, —$CONR^aR^b$, —$SR^a$, —$SOR^a$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, —$NR^aSO_2R^b$, —$NR^aSO_2NR^aR^b$, —$OR^a$, —$OC(O)R^a$, and —$OC(O)NR^aR^b$; wherein $R^a$ and $R^b$ are defined as above; or (6)

wherein in (6),
L/(6) is NH or $CH_2$; or (7)

wherein in 7,
M/(7) is hydrogen, halo, amino, cyano, $(C_1-C_8)$alkyl, $(C_3-C_8)$cycloalkyl, heterocycloalkyl, —$COR^a$, —$CO_2R^a$, —$CONR^aR^b$, —$CONR^aNR^aR^b$, —$SO_2R^a$, —$SO_2NR^aR^b$, —$NR^aR^b$, —$NR^aC(O)R^b$, —$NR^aSO_2R^b$, —$NR^aSO_2NR^aR^b$, —$NR^aNR^aR^b$, —$NR^aNR^aC(O)R^b$, —$NR^aNR^aC(O)NR^aR^b$, or —$OR^a$
wherein any $(C_1-C_8)$alkyl, $(C_3-C_8)$cycloalkyl, or heterocycloalkyl group is optionally substituted by 1, 2 or 3 groups independently selected from $(C_1-C_6)$alkyl, $(C_3-C_8)$cycloalkyl, $(C_5-C_8)$cycloalkenyl, $(C_1-C_6)$haloalkyl, cyano, —$COR^a$, —$CO_2R^a$, —$CONR^aR^b$, —$SR^a$, —$SOR^a$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, —$NR^aSO_2R^b$, —$NR^aSO_2NR^aR^b$, —$OR^a$, —$OC(O)R^a$, and —$OC(O)NR^aR^b$; wherein $R^a$ and $R^b$ are defined as above; or (8)

wherein in (8),
P is $CH_2$, NH, O, or S; Q/(8) is CH or N; and n is 0-2; or (9)

wherein in (9),
S/(9) and T/(9) is C, or S/(9) is C and T/(9) is N, or S/(9) is N and T/(9) is C;
R is hydrogen, amino, methyl, trifluoromethyl, or halo;
U is hydrogen, halo, amino, cyano, nitro, trifluoromethyl, $(C_1-C_8)$alkyl, $(C_3-C_8)$cycloalkyl, —$COR^a$, —$CO_2R^a$, —$CONR^aR^b$, —$SO_2R^a$, —$SO_2NR^aR^b$, —$NR^aR^b$, —$NR^aC(O)R^b$, —$NR^aSO_2R^b$, —$NR^aSO_2NR^aR^b$, —$NR^aNR^aR^b$, —$NR^aNR^aC(O)R^b$, —$OR^a$, or 4-(1H-pyrazol-4-yl),
wherein any $(C_1-C_8)$alkyl or $(C_3-C_8)$cycloalkyl group is optionally substituted by 1, 2 or 3 groups independently selected from $(C_1-C_6)$alkyl, $(C_3-C_8)$cycloalkyl, $(C_5-C_8)$cycloalkenyl, $(C_1-C_6)$haloalkyl, cyano, —$COR^a$, —$CO_2R_a$, —$CONR^aR^b$, —$SR^a$, $SOR^a$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, —$NR^aSO_2R^b$, —$NR^aSO_2NR^aR^b$, —$OR^a$, —$OC(O)R^a$, and —$OC(O)NR^aR^b$; wherein $R^a$ and $R^b$ are defined as above.

Subgroup B of Formula (VII)
X and Z are selected independently from the group consisting of $(C_1-C_8)$alkyl, $(C_3-C_8)$cycloalkyl, heterocycloalkyl, aryl, heteroaryl, —$NR^aR^b$, and —$OR^a$;
Y is H;
$R^1$ is $(C_1-C_8)$alkyl, $(C_3-C_8)$cycloalkyl, or heterocycloalkyl;
$R^2$ is hydrogen, $(C_1-C_3)$alkyl, or halo, in which said $(C_1-C_3)$alkyl is optionally substituted with one to two groups selected from amino and $(C_1-C_3)$alkylamino;
$R^7$ is hydrogen, $(C_1-C_3)$alkyl, or alkoxy;
$R^3$ is hydrogen, $(C_1-C_8)$alkyl or halo;
$R^6$ is hydrogen, halo, cyano, trifluoromethyl, amino, $(C_1-C_8)$alkyl, $(C_3-C_8)$cycloalkyl, aryl, heteroaryl, acylamino; $(C_2-C_8)$alkynyl, arylalkynyl, heteroarylalkynyl, —$SO_2R^a$, —$SO_2NR^aR^b$, or —$NR^aSO_2R^b$;
wherein any $(C_1-C_8)$alkyl, $(C_3-C_8)$cycloalkyl, $(C_2-C_8)$alkynyl, arylalkynyl, or heteroarylalkynyl group is optionally substituted by 1, 2 or 3 groups independently selected from halo, $(C_1-C_6)$alkyl, $(C_3-C_8)$cycloalkyl, $(C_5-C_8)$cycloalkenyl, $(C_1-C_6)$haloalkyl, cyano, —$COR^a$, —$CO_2R^a$, —$CONR^aR^b$, —$SR^a$, —$SOR^a$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, —$NR^aSO_2R^b$, —$NR^aSO_2NR^aR^b$, —$OR^a$, —$OC(O)R^a$, —$OC(O)NR^aR^b$, heterocycloalkyl, aryl, heteroaryl, aryl$(C_1-C_4)$alkyl, and heteroaryl$(C_1-C_4)$alkyl;
$R^a$ and $R^b$ are each independently hydrogen, $(C_1-C_8)$alkyl, $(C_2-C_8)$alkenyl, $(C_2-C_8)$alkynyl, $(C_3-C_8)$cycloalkyl, $(C_5-C_8)$cycloalkenyl, $(C_6-C_{10})$bicycloalkyl, heterocycloalkyl, aryl, or heteroaryl, wherein said $(C_1-C_8)$alkyl, $(C_2-C_8)$alkenyl, $(C_2-C_8)$alkynyl, cycloalkyl, cycloalkenyl, bicycloalkyl, heterocycloalkyl, aryl or heteroaryl group is optionally substituted by 1, 2 or 3 groups independently selected from halo, hydroxyl, $(C_1-C_4)$alkoxy, amino, $(C_1-C_4)$alkylamino, (($C_1-C_4$)alkyl)(($C_1-C_4$)alkyl)amino, —$CO_2H$, —$CO_2(C_1-C_4)$alkyl, —$CONH_2$, —$CONH(C_1-C_4)$alkyl, —$CON((C_1-C_4)$alkyl)(($C_1-C_4$)alkyl), —$SO_2(C_1-C_4)$alkyl, —$SO_2NH_2$, —$SO_2NH(C_1-C_4)$alkyl, and —$SO_2N((C_1-C_4)$alkyl)(($C_1-C_4$)alkyl);
or $R^a$ and $R^b$ taken together with the nitrogen to which they are attached represent a 5-8 membered saturated or unsaturated ring, optionally containing an additional heteroatom selected from oxygen, nitrogen, and sulfur, wherein said ring is optionally substituted by 1, 2 or 3 groups independently selected from $(C_1-C_4)$alkyl, $(C_1-C_4)$haloalkyl, amino, $(C_1-C_4)$alkylamino, (($C_1-C_4$)alkyl)(($C_1-C_4$)alkyl)amino, hydroxyl, oxo, $(C_1-C_4)$alkoxy, and $(C_1-C_4)$ alkoxy($C_1$-$C_4$)alkyl, wherein said ring is optionally fused to a ($C_3$-$C_8$)cycloalkyl, heterocycloalkyl, aryl, or heteroaryl ring;

or $R^a$ and $R^b$ taken together with the nitrogen to which they are attached represent a 6- to 10-membered bridged bicyclic ring system optionally fused to a ($C_3$-$C_8$)cycloalkyl, heterocycloalkyl, aryl, or heteroaryl ring. Aryl and heteroaryl in this definition are selected from the group consisting of furan, thiophene, pyrrole, oxazole, thiazole, imidazole, pyrazole, oxadiazole, thiadiazole, triazole, tetrazole, benzofuran, benzothiophene, benzoxazole, benzothiazole, phenyl, pyridine, pyridazine, pyrimidine, pyrazine, triazine, tetrazine, quinoline, cinnoline, quinazoline, quinoxaline, and naphthyridine or a compound of another aryl or heteroaryl group as follows:

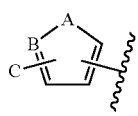

(1)

wherein in (1),
A is O, NH, or S; B is CH or N, and C is hydrogen or $C_1$-$C_8$ alkyl; or

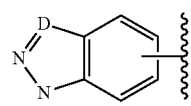

(2)

wherein in (2),
D is N or C optionally substituted by hydrogen or $C_1$-$C_8$ alkyl; or

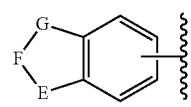

(3)

wherein in (3),
E is NH or $CH_2$; F is O or CO; and G is NH or $CH_2$; or

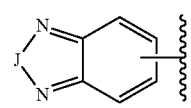

(4)

wherein in (4),
J is O, S or CO; or

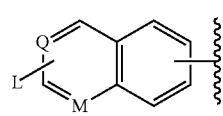

(5)

wherein in (5),

Q is CH or N;
M is CH or N; and
L/(5) is hydrogen, halo, amino, cyano, ($C_1$-$C_8$)alkyl, ($C_3$-$C_8$)cycloalkyl, —$COR^a$, —$CO_2R^a$, —$CONR^aR^b$, —$CONR^aNR^aR^b$, —$SO_2R^a$, —$SO_2NR^aR^b$, —$NR^aR^b$, —$NR^aC(O)R^b$, —$NR^aSO_2R^b$, —$NR^aSO_2NR^aR^b$, —$NR^aNR^aR^b$, —$NR^aNR^aC(O)R^b$, —$NR^aNR^aC(O)NR^aR^b$, or —$OR^a$, wherein any ($C_1$-$C_8$)alkyl, ($C_3$-$C_8$)cycloalkyl, group is optionally substituted by 1, 2 or 3 groups independently selected from ($C_1$-$C_6$)alkyl, ($C_3$-$C_8$)cycloalkyl, ($C_5$-$C_8$)cycloalkenyl, ($C_1$-$C_6$)haloalkyl, cyano, —$COR^a$, —$CO_2R^a$, —$CONR^aR^b$, —$SR^a$, —$SOR^a$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, $NR^aSO_2R^b$, —$NR^aSO_2NR^aR^b$, —$OR^a$, —$OC(O)R^a$, and —$OC(O)NR^aR^b$, wherein $R_a$ and $R^b$ are defined as above; or

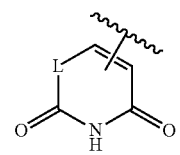

(6)

wherein in (6),
L/(6) is NH or $CH_2$; or

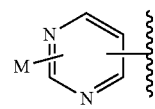

(7)

wherein in (7),
M/(7) is hydrogen, halo, amino, cyano, ($C_1$-$C_8$)alkyl, ($C_3$-$C_8$)cycloalkyl, heterocycloalkyl, —$COR^a$, —$CO_2R^a$, —$CONR^aR^b$, —$CONR^aNR^aR^b$, —$SO_2R^a$, —$SO_2NR^aR^b$, —$NR^aR^b$, —$NR^aC(O)R^b$, —$NR^aSO_2R^b$, —$NR^aSO_2NR^aR^b$, —$NR^aNR^aR^b$, —$NR^aNR^aC(O)R^b$, —$NR^aNR^aC(O)NR^aR^b$, or —$OR^a$ wherein any ($C_1$-$C_8$)alkyl, ($C_3$-$C_8$)cycloalkyl, heterocycloalkyl group is optionally substituted by 1, 2 or 3 groups independently selected from ($C_1$-$C_6$)alkyl, ($C_3$-$C_8$)cycloalkyl, ($C_5$-$C_8$)cycloalkenyl, ($C_1$-$C_6$)haloalkyl, cyano, —$COR^a$, —$CO_2R^a$, —$CONR^aR^b$, —$SR^a$, —$SOR^a$, —$SO_2R^a$, —$SO_2NR^aR^b$, nitro, —$NR^aR^b$, —$NR^aC(O)R^b$, $NR^aC(O)NR^aR^b$, —$NR^aC(O)OR^a$, —$NR^aSO_2R^b$, —$NR^aSO_2NR^aR^b$, —$OR^a$, —$OC(O)R^a$, —$OC(O)NR^aR^b$; wherein $R^a$ and $R^b$ are defined as above; or

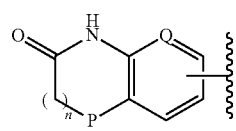

(8)

wherein in (8),

P is $CH_2$, NH, O, or S; Q/(8) is CH or N; and n is 0-2; or

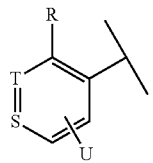
(9)

wherein in (9),

S/(9) and T/(9) is C, or S/(9) is C and T/(9) is N, or S/(9) is N and T/(9) is C;

R is hydrogen, amino, methyl, trifluoromethyl, halo;

U is hydrogen, halo, amino, cyano, nitro, trifluoromethyl, $(C_1-C_8)$alkyl, $(C_3-C_8)$cycloalkyl, —$COR^a$, —$CO_2R^a$, —$CONR^aR^b$, —$SO_2R^a$, —$SO_2NR^aR^b$, —$NR^aR^b$, —$NR^aC(O)R^b$, —$NR^aSO_2R^b$, $NR^aSO_2NR^aR^b$, —$NR^aNR^aR^b$, —$NR^aNR^aC(O)R^b$, —$OR^a$, or 4-(1H-pyrazol-4-yl), wherein any $(C_1-C_8)$alkyl, or $(C_3-C_8)$cycloalkyl group is optionally substituted by 1, 2 or 3 groups independently selected from $(C_1-C_6)$alkyl, $(C_3-C_8)$cycloalkyl, $(C_5-C_8)$cycloalkenyl, $(C_1-C_6)$haloalkyl, cyano, —$COR^a$, —$CO_2R^a$, —$CONR^aR^b$, —$SOR^a$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, —$NR^aSO_2R^b$, —$NR^aSO_2NR^aR^b$, —$OR^a$, —$OC(O)R^a$, and —$OC(O)NR^aR^b$, wherein Ra and Rb are defined as above.

In embodiments, the EZH2 inhibitor is Compound G or GSK-126:

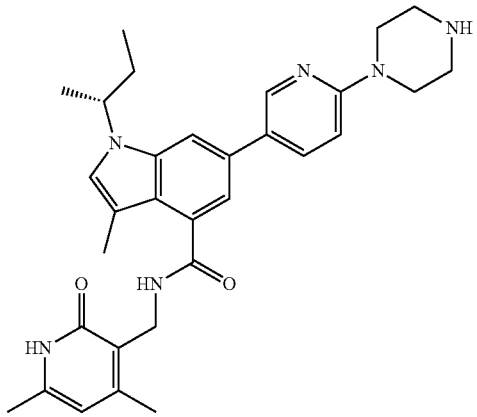
(G)

or stereoisomers thereof or pharmaceutically acceptable salt or solvate thereof.

In certain embodiments, an EZH2 inhibitor that can be used in any methods presented here is Compound H:

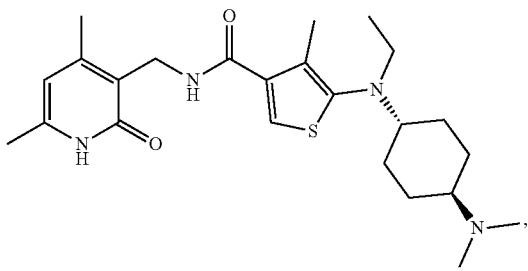
(H)

or stereoisomers thereof or pharmaceutically acceptable salts and solvates thereof.

In certain embodiments, an EZH2 inhibitor that can be used in any methods presented here is any of Compounds Ga-Gc:

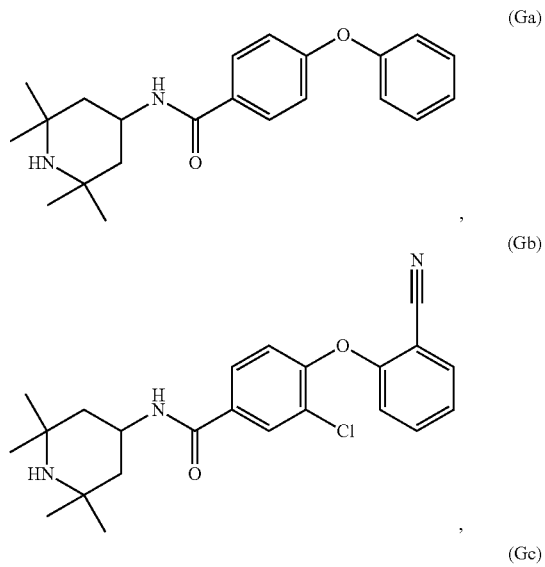
(Ga)

(Gb)

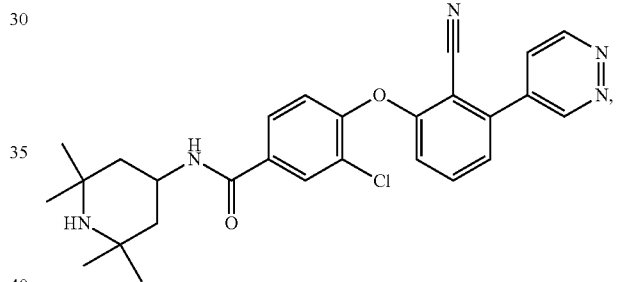
(Gc)

or a stereoisomer, pharmaceutically acceptable salt or solvate thereof.

In certain embodiments, an EZH2 inhibitor that can be used in any methods presented here is CPI-1205 or GSK343.

In one embodiment, the compound (e.g., an EZH2 inhibitor) disclosed herein is the compound itself, i.e., the free base or "naked" molecule. In another embodiment, the compound is a salt thereof, e.g., a mono-HCl or tri-HCl salt, mono-HBr or tri-HBr salt of the naked molecule.

The compounds described herein can be synthesized according to any method known in the art. For example, the compounds having the Formula (VII) can be synthesized according to the method described in WO 2011/140325; WO 2011/140324; and WO 2012/005805, each of which is incorporated by reference in its entirety.

As used herein, "alkyl", "$C_1$, $C_2$, $C_3$, $C_4$, $C_5$ or $C_6$ alkyl" or "$C_1$-$C_6$ alkyl" is intended to include $C_1$, $C_2$, $C_3$, $C_4$, $C_5$ or $C_6$ straight chain (linear) saturated aliphatic hydrocarbon groups and $C_3$, $C_4$, $C_5$ or $C_6$ branched saturated aliphatic hydrocarbon groups. For example, $C_1$-$C_6$ alkyl is intended to include $C_1$, $C_2$, $C_3$, $C_4$, $C_5$ and $C_6$ alkyl groups. Examples of alkyl include, moieties having from one to six carbon atoms, such as, but not limited to, methyl, ethyl, n-propyl, i-propyl, n-butyl, s-butyl, t-butyl, n-pentyl, s-pentyl or n-hexyl.

In embodiments, a straight chain or branched alkyl has six or fewer carbon atoms (e.g., $C_1$-$C_6$ for straight chain, $C_3$-$C_6$ for branched chain), and in another embodiment, a straight chain or branched alkyl has four or fewer carbon atoms.

As used herein, the term "cycloalkyl" refers to a saturated or unsaturated nonaromatic hydrocarbon mono- or multi-ring (e.g., fused, bridged, or spiro rings) system having 3 to 30 carbon atoms (e.g., $C_3$-$C_{10}$). Examples of cycloalkyl include, but are not limited to, cyclopropyl, cyclobutyl, cyclopentyl, cyclohexyl, cycloheptyl, cyclooctyl, cyclopentenyl, cyclohexenyl, cycloheptenyl, and adamantyl. The term "heterocycloalkyl" refers to a saturated or unsaturated nonaromatic 3-8 membered monocyclic, 7-12 membered bicyclic (fused, bridged, or spiro rings), or 11-14 membered tricyclic ring system (fused, bridged, or spiro rings) having one or more heteroatoms (such as O, N, S, or Se), unless specified otherwise. Examples of heterocycloalkyl groups include, but are not limited to, piperidinyl, piperazinyl, pyrrolidinyl, dioxanyl, tetrahydrofuranyl, isoindolinyl, indolinyl, imidazolidinyl, pyrazolidinyl, oxazolidinyl, isoxazolidinyl, triazolidinyl, tetrahyrofuranyl, oxiranyl, azetidinyl, oxetanyl, thietanyl, 1,2,3,6-tetrahydropyridinyl, tetrahydropyranyl, dihydropyranyl, pyranyl, morpholinyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, 1,4-dioxa-8-azaspiro[4.5]decanyl and the like.

The term "optionally substituted alkyl" refers to unsubstituted alkyl or alkyl having designated substituents replacing one or more hydrogen atoms on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

An "arylalkyl" or an "aralkyl" moiety is an alkyl substituted with an aryl (e.g., phenylmethyl (benzyl)). An "alkylaryl" moiety is an aryl substituted with an alkyl (e.g., methylphenyl).

As used herein, "alkyl linker" is intended to include $C_1$, $C_2$, $C_3$, $C_4$, $C_5$ or $C_6$ straight chain (linear) saturated divalent aliphatic hydrocarbon groups and $C_3$, $C_4$, $C_5$ or $C_6$ branched saturated aliphatic hydrocarbon groups. For example, $C_1$-$C_6$ alkyl linker is intended to include $C_1$, $C_2$, $C_3$, $C_4$, $C_5$ and $C_6$ alkyl linker groups. Examples of alkyl linker include, moieties having from one to six carbon atoms, such as, but not limited to, methyl (—$CH_2$—), ethyl (—$CH_2CH_2$—), n-propyl (—$CH_2CH_2CH_2$—), i-propyl (—$CHCH_3CH_2$—), n-butyl (—$CH_2CH_2CH_2CH_2$—), s-butyl (—$CHCH_3$ $CH_2CH_2$—), i-butyl (—$C(CH_3)_2CH_2$—), n-pentyl (—$CH_2CH_2CH_2CH_2CH_2$—), s-pentyl (—$CHCH_3CH_2CH_2CH_2$—) or n-hexyl (—$CH_2CH_2CH_2CH_2CH_2CH_2$—).

"Alkenyl" includes unsaturated aliphatic groups analogous in length and possible substitution to the alkyls described above, but that contain at least one double bond. For example, the term "alkenyl" includes straight chain alkenyl groups (e.g., ethenyl, propenyl, butenyl, pentenyl, hexenyl, heptenyl, octenyl, nonenyl, decenyl), and branched alkenyl groups. In embodiments, a straight chain or branched alkenyl group has six or fewer carbon atoms in its backbone (e.g., $C_2$-$C_6$ for straight chain, $C_3$-$C_6$ for branched chain). The term "$C_2$-$C_6$" includes alkenyl groups containing two to six carbon atoms. The term "$C_3$-$C_6$" includes alkenyl groups containing three to six carbon atoms.

The term "optionally substituted alkenyl" refers to unsubstituted alkenyl or alkenyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, heterocyclyl, alkylaryl, or an aromatic or heteroaromatic moiety.

"Alkynyl" includes unsaturated aliphatic groups analogous in length and possible substitution to the alkyls described above, but which contain at least one triple bond. For example, "alkynyl" includes straight chain alkynyl groups (e.g., ethynyl, propynyl, butynyl, pentynyl, hexynyl, heptynyl, octynyl, nonynyl, decynyl), and branched alkynyl groups. In embodiments, a straight chain or branched alkynyl group has six or fewer carbon atoms in its backbone (e.g., $C_2$-$C_6$ for straight chain, $C_3$-$C_6$ for branched chain). The term "$C_2$-$C_6$" includes alkynyl groups containing two to six carbon atoms. The term "$C_3$-$C_6$" includes alkynyl groups containing three to six carbon atoms.

The term "optionally substituted alkynyl" refers to unsubstituted alkynyl or alkynyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Other optionally substituted moieties (such as optionally substituted cycloalkyl, heterocycloalkyl, aryl, or heteroaryl) include both the unsubstituted moieties and the moieties having one or more of the designated substituents. For example, substituted heterocycloalkyl includes those substituted with one or more alkyl groups, such as 2,2,6,6-tetramethyl-piperidinyl and 2,2,6,6-tetramethyl-1,2,3,6-tetrahydropyridinyl.

"Aryl" includes groups with aromaticity, including "conjugated," or multicyclic systems with at least one aromatic ring and do not contain any heteroatom in the ring structure. Examples include phenyl, benzyl, 1,2,3,4-tetrahydronaphthalenyl, etc.

"Heteroaryl" groups are aryl groups, as defined above, except having from one to four heteroatoms in the ring structure, and may also be referred to as "aryl heterocycles"

or "heteroaromatics." As used herein, the term "heteroaryl" is intended to include a stable 5-, 6-, or 7-membered monocyclic or 7-, 8-, 9-, 10-, 11- or 12-membered bicyclic aromatic heterocyclic ring which consists of carbon atoms and one or more heteroatoms, e.g., 1 or 1-2 or 1-3 or 1-4 or 1-5 or 1-6 heteroatoms, or e.g. 1, 2, 3, 4, 5, or 6 heteroatoms, independently selected from the group consisting of nitrogen, oxygen and sulfur. The nitrogen atom may be substituted or unsubstituted (i.e., N or NR wherein R is H or other substituents, as defined). The nitrogen and sulfur heteroatoms may optionally be oxidized (i.e., N→O and $S(O)_p$, where p=1 or 2). It is to be noted that total number of S and O atoms in the aromatic heterocycle is not more than 1.

Examples of heteroaryl groups include pyrrole, furan, thiophene, thiazole, isothiazole, imidazole, triazole, tetrazole, pyrazole, oxazole, isoxazole, pyridine, pyrazine, pyridazine, pyrimidine, and the like.

Furthermore, the terms "aryl" and "heteroaryl" include multicyclic aryl and heteroaryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, naphthrydine, indole, benzofuran, purine, benzofuran, deazapurine, indolizine.

In the case of multicyclic aromatic rings, only one of the rings needs to be aromatic (e.g., 2,3-dihydroindole), although all of the rings may be aromatic (e.g., quinoline). The second ring can also be fused or bridged.

The cycloalkyl, heterocycloalkyl, aryl, or heteroaryl ring can be substituted at one or more ring positions (e.g., the ring-forming carbon or heteroatom such as N) with such substituents as described above, for example, alkyl, alkenyl, alkynyl, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl and heteroaryl groups can also be fused or bridged with alicyclic or heterocyclic rings, which are not aromatic so as to form a multicyclic system (e.g., tetralin, methylenedioxyphenyl).

As used herein, "carbocycle" or "carbocyclic ring" is intended to include any stable monocyclic, bicyclic or tricyclic ring having the specified number of carbons, any of which may be saturated, unsaturated, or aromatic. Carbocycle includes cycloalkyl and aryl. For example, a $C_3$-$C_{14}$ carbocycle is intended to include a monocyclic, bicyclic or tricyclic ring having 3, 4, 5, 6, 7, 8, 9, 10, 11, 12, 13 or 14 carbon atoms. Examples of carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, fluorenyl, phenyl, naphthyl, indanyl, adamantyl and tetrahydronaphthyl. Bridged rings are also included in the definition of carbocycle, including, for example, [3.3.0]bicyclooctane, [4.3.0]bicyclononane, [4.4.0]bicyclodecane and [2.2.2]bicyclooctane. A bridged ring occurs when one or more carbon atoms link two non-adjacent carbon atoms. In one embodiment, bridge rings are one or two carbon atoms. It is noted that a bridge always converts a monocyclic ring into a tricyclic ring. When a ring is bridged, the substituents recited for the ring may also be present on the bridge. Fused (e.g., naphthyl, tetrahydronaphthyl) and spiro rings are also included.

As used herein, "heterocycle" or "heterocyclic group" includes any ring structure (saturated, unsaturated, or aromatic) which contains at least one ring heteroatom (e.g., N, O or S). Heterocycle includes heterocycloalkyl and heteroaryl. Examples of heterocycles include, but are not limited to, morpholine, pyrrolidine, tetrahydrothiophene, piperidine, piperazine, oxetane, pyran, tetrahydropyran, azetidine, and tetrahydrofuran.

Examples of heterocyclic groups include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2,4-oxadiazol5(4H)-one, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl and xanthenyl.

The term "substituted," as used herein, means that any one or more hydrogen atoms on the designated atom is replaced with a selection from the indicated groups, provided that the designated atom's normal valency is not exceeded, and that the substitution results in a stable compound. When a substituent is oxo or keto (i.e., =O), then 2 hydrogen atoms on the atom are replaced. Keto substituents are not present on aromatic moieties. Ring double bonds, as used herein, are double bonds that are formed between two adjacent ring atoms (e.g., C=C, C=N or N=N). "Stable compound" and "stable structure" are meant to indicate a compound that is sufficiently robust to survive isolation to a useful degree of purity from a reaction mixture, and formulation into an efficacious therapeutic agent.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such formula. Combinations of substituents or variables are permissible (or both), but only if such combinations result in stable compounds.

When any variable (e.g., $R_1$) occurs more than one time in any constituent or formula for a compound, its definition at each occurrence is independent of its definition at every other occurrence. Thus, for example, if a group is shown to be substituted with 0-2 $R_1$ moieties, then the group may optionally be substituted with up to two $R_1$ moieties and $R_1$ at each occurrence is selected independently from the definition of $R_1$. Also, combinations of substituents or variables are permissible (or both), but only if such combinations result in stable compounds.

The term "hydroxy" or "hydroxyl" includes groups with an —OH or —O⁻.

As used herein, "halo" or "halogen" refers to fluoro, chloro, bromo and iodo. The term "perhalogenated" generally refers to a moiety wherein all hydrogen atoms are replaced by halogen atoms. The term "haloalkyl" or "haloalkoxyl" refers to an alkyl or alkoxyl substituted with one or more halogen atoms.

The term "carbonyl" includes compounds and moieties which contain a carbon connected with a double bond to an oxygen atom. Examples of moieties containing a carbonyl include, but are not limited to, aldehydes, ketones, carboxylic acids, amides, esters, anhydrides, etc.

The term "carboxyl" refers to —COOH or its $C_1$-$C_6$ alkyl ester.

"Acyl" includes moieties that contain the acyl radical (R—C(O)—) or a carbonyl group. "Substituted acyl" includes acyl groups where one or more of the hydrogen atoms are replaced by, for example, alkyl groups, alkynyl groups, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Aroyl" includes moieties with an aryl or heteroaromatic moiety bound to a carbonyl group. Examples of aroyl groups include phenylcarboxy, naphthyl carboxy, etc.

"Alkoxyalkyl," "alkylaminoalkyl," and "thioalkoxyalkyl" include alkyl groups, as described above, wherein oxygen, nitrogen, or sulfur atoms replace one or more hydrocarbon backbone carbon atoms.

The term "alkoxy" or "alkoxyl" includes substituted and unsubstituted alkyl, alkenyl and alkynyl groups covalently linked to an oxygen atom. Examples of alkoxy groups or alkoxyl radicals include, but are not limited to, methoxy, ethoxy, isopropyloxy, propoxy, butoxy and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy and trichloromethoxy.

The term "ether" or "alkoxy" includes compounds or moieties which contain an oxygen bonded to two carbon atoms or heteroatoms. For example, the term includes "alkoxyalkyl," which refers to an alkyl, alkenyl, or alkynyl group covalently bonded to an oxygen atom which is covalently bonded to an alkyl group.

The term "ester" includes compounds or moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc.

The term "thioalkyl" includes compounds or moieties which contain an alkyl group connected with a sulfur atom. The thioalkyl groups can be substituted with groups such as alkyl, alkenyl, alkynyl, halogen, hydroxyl, alkylcarbonyloxy, arylcarbonyloxy, alkoxycarbonyloxy, aryloxycarbonyloxy, carboxylate, carboxyacid, alkylcarbonyl, arylcarbonyl, alkoxycarbonyl, aminocarbonyl, alkylaminocarbonyl, dialkylaminocarbonyl, alkylthiocarbonyl, alkoxyl, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties.

The term "thiocarbonyl" or "thiocarboxy" includes compounds and moieties which contain a carbon connected with a double bond to a sulfur atom.

The term "thioether" includes moieties which contain a sulfur atom bonded to two carbon atoms or heteroatoms. Examples of thioethers include, but are not limited to alkthioalkyls, alkthioalkenyls, and alkthioalkynyls. The term "alkthioalkyls" include moieties with an alkyl, alkenyl, or alkynyl group bonded to a sulfur atom which is bonded to an alkyl group. Similarly, the term "alkthioalkenyls" refers to moieties wherein an alkyl, alkenyl or alkynyl group is bonded to a sulfur atom which is covalently bonded to an alkenyl group; and alkthioalkynyls" refers to moieties wherein an alkyl, alkenyl or alkynyl group is bonded to a sulfur atom which is covalently bonded to an alkynyl group.

As used herein, "amine" or "amino" refers to unsubstituted or substituted —$NH_2$. "Alkylamino" includes groups of compounds wherein nitrogen of —$NH_2$ is bound to at least one alkyl group. Examples of alkylamino groups include benzylamino, methylamino, ethylamino, phenethylamino, etc. "Dialkylamino" includes groups wherein the nitrogen of —$NH_2$ is bound to at least two additional alkyl groups. Examples of dialkylamino groups include, but are not limited to, dimethylamino and diethylamino. "Arylamino" and "diarylamino" include groups wherein the nitrogen is bound to at least one or two aryl groups, respectively. "Aminoaryl" and "aminoaryloxy" refer to aryl and aryloxy substituted with amino. "Alkylarylamino," "alkylaminoaryl" or "arylaminoalkyl" refers to an amino group which is bound to at least one alkyl group and at least one aryl group. "Alkaminoalkyl" refers to an alkyl, alkenyl, or alkynyl group bound to a nitrogen atom which is also bound to an alkyl group. "Acylamino" includes groups wherein nitrogen is bound to an acyl group. Examples of acylamino include, but are not limited to, alkylcarbonylamino, arylcarbonylamino, carbamoyl and ureido groups.

The term "amide" or "aminocarboxy" includes compounds or moieties that contain a nitrogen atom that is bound to the carbon of a carbonyl or a thiocarbonyl group. The term includes "alkaminocarboxy" groups that include alkyl, alkenyl or alkynyl groups bound to an amino group which is bound to the carbon of a carbonyl or thiocarbonyl group. It also includes "arylaminocarboxy" groups that include aryl or heteroaryl moieties bound to an amino group that is bound to the carbon of a carbonyl or thiocarbonyl group. The terms "alkylaminocarboxy", "alkenylaminocarboxy", "alkynylaminocarboxy" and "arylaminocarboxy" include moieties wherein alkyl, alkenyl, alkynyl and aryl moieties, respectively, are bound to a nitrogen atom which is in turn bound to the carbon of a carbonyl group. Amides can be substituted with substituents such as straight chain alkyl, branched alkyl, cycloalkyl, aryl, heteroaryl or heterocycle. Substituents on amide groups may be further substituted.

In the present specification, the structural formula of the compound represents a certain isomer for convenience in some cases, but the present invention includes all isomers, such as geometrical isomers, optical isomers based on an asymmetrical carbon, stereoisomers, tautomers, and the like, it being understood that not all isomers may have the same level of activity. In addition, a crystal polymorphism may be present for the compounds represented by the formula. It is noted that any crystal form, crystal form mixture, or anhydride or hydrate thereof is included in the scope of the present invention.

"Isomerism" means compounds that have identical molecular formulae but differ in the sequence of bonding of their atoms or in the arrangement of their atoms in space. Isomers that differ in the arrangement of their atoms in space are termed "stereoisomers." Stereoisomers that are not mirror images of one another are termed "diastereoisomers," and stereoisomers that are non-superimposable mirror images of each other are termed "enantiomers" or sometimes optical isomers. A mixture containing equal amounts of individual enantiomeric forms of opposite chirality is termed a "racemic mixture."

A carbon atom bonded to four nonidentical substituents is termed a "chiral center."

"Chiral isomer" means a compound with at least one chiral center. Compounds with more than one chiral center may exist either as an individual diastereomer or as a mixture of diastereomers, termed "diastereomeric mixture." When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the *Sequence Rule* of Cahn, Ingold and Prelog. (Cahn et al., *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, *J. Chem. Educ.* 1964, 41, 116).

"Geometric isomer" means the diastereomers that owe their existence to hindered rotation about double bonds or a cycloalkyl linker (e.g., 1,3-cylcobutyl). These configurations are differentiated in their names by the prefixes cis and trans, or Z and E, which indicate that the groups are on the same or opposite side of the double bond in the molecule according to the Cahn-Ingold-Prelog rules.

It is to be understood that the compounds of the present invention may be depicted as different chiral isomers or geometric isomers. It should also be understood that when compounds have chiral isomeric or geometric isomeric forms, all isomeric forms are intended to be included in the scope of the present invention, and the naming of the compounds does not exclude any isomeric forms, it being understood that not all isomers may have the same level of activity.

Furthermore, the structures and other compounds discussed in this invention include all atropic isomers thereof, it being understood that not all atropic isomers may have the same level of activity. "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

"Tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solutions where tautomerization is possible, a chemical equilibrium of the tautomers will be reached. The exact ratio of the tautomers depends on several factors, including temperature, solvent and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose.

Common tautomeric pairs are: ketone-enol, amide-nitrile, lactam-lactim, amide-imidic acid tautomerism in heterocyclic rings (e.g., in nucleobases such as guanine, thymine and cytosine), imine-enamine and enamine-enamine. An example of keto-enol equilibria is between pyridin-2(1H)-ones and the corresponding pyridin-2-ols, as shown below.

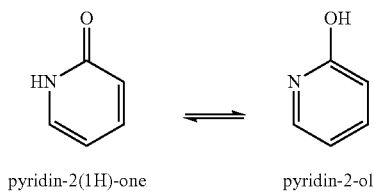 [SMILES: O=c1cccc[nH]1 ; Oc1ccccn1]

pyridin-2(1H)-one      pyridin-2-ol

In the compounds described herein, each occurrence of

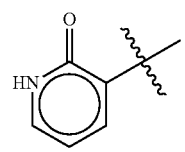

should be construed as

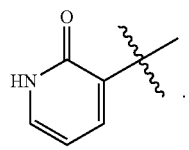

It is to be understood that the compounds of the present invention may be depicted as different tautomers. It should also be understood that when compounds have tautomeric forms, all tautomeric forms are intended to be included in the scope of the present invention, and the naming of the compounds does not exclude any tautomer form. It will be understood that certain tautomers may have a higher level of activity than others.

The term "crystal polymorphs", "polymorphs" or "crystal forms" means crystal structures in which a compound (or a salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

The compounds of any of Formulae disclosed herein include the compounds themselves, as well as their salts or their solvates, if applicable. A salt, for example, can be formed between an anion and a positively charged group (e.g., amino) on an aryl- or heteroaryl-substituted benzene compound. Suitable anions include chloride, bromide, iodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate, and acetate (e.g., trifluoroacetate). The term "pharmaceutically acceptable anion" refers to an anion suitable for forming a pharmaceutically acceptable salt. Likewise, a salt can also be formed between a cation and a negatively charged group (e.g., carboxylate) on an aryl- or heteroaryl-substituted benzene compound. Suitable cations include sodium ion, potassium ion, magnesium ion, calcium ion, and an ammonium cation such as tetramethylammonium ion. The aryl- or heteroaryl-substituted benzene compounds also include those salts containing quaternary nitrogen atoms.

Additionally, the compounds of the present invention, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

"Solvate" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$.

The term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physicochemically or topologically based. Examples of carboxylic acid bioisosteres include, but are not limited to, acyl sulfonimides, tetrazoles, sulfonates and phosphonates. See, e.g., Patani and LaVoie, Chem. Rev. 96, 3147-3176, 1996.

The present invention is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

The present invention provides methods for the synthesis of the compounds of any Formula disclosed herein. The present invention also provides detailed methods for the synthesis of various disclosed compounds of the present invention according to the following schemes as shown in the Examples.

Throughout the description, where compositions are described as having, including, or comprising specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously.

The synthetic processes of the invention can tolerate a wide variety of functional groups, therefore various substituted starting materials can be used. The processes generally provide the desired final compound at or near the end of the overall process, although it may be desirable in certain instances to further convert the compound to a pharmaceutically acceptable salt, solvate or polymorph thereof.

Compounds of the present invention can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., *March's Advanced Organic Chemistry. Reactions, Mechanisms, and Structure*, 5$^{th}$ edition, John Wiley & Sons: New York, 2001; Greene, T. W., Wuts, P. G. M., *Protective Groups in Organic Synthesis*, 3$^{rd}$ edition, John Wiley & Sons: New York, 1999; R. Larock, *Comprehensive Organic Transformations*, VCH Publishers (1989); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), incorporated by reference herein, are useful and recognized reference textbooks of organic synthesis known to those in the art. The following descriptions of synthetic methods are designed to illustrate, but not to limit, general procedures for the preparation of compounds of the present invention.

Compounds of the present invention can be conveniently prepared by a variety of methods familiar to those skilled in the art. The compounds of this invention with any Formula disclosed herein may be prepared according to the procedures illustrated in Schemes 1-10 below, from commercially available starting materials or starting materials which can be prepared using literature procedures. The Z and R groups (such as $R_2$, $R_3$, $R_4$, $R_6$, $R_7$, $R_8$, and $R_{12}$) in Schemes 1-10 are as defined in any of Formulae disclosed herein, unless otherwise specified.

One of ordinary skill in the art will note that, during the reaction sequences and synthetic schemes described herein, the order of certain steps may be changed, such as the introduction and removal of protecting groups.

One of ordinary skill in the art will recognize that certain groups may require protection from the reaction conditions via the use of protecting groups. Protecting groups may also be used to differentiate similar functional groups in molecules. A list of protecting groups and how to introduce and remove these groups can be found in Greene, T. W., Wuts, P. G. M., *Protective Groups in Organic Synthesis*, 3$^{rd}$ edition, John Wiley & Sons: New York, 1999.

Preferred protecting groups include, but are not limited to:
For a hydroxyl moiety: TBS, benzyl, THP, Ac
For carboxylic acids: benzyl ester, methyl ester, ethyl ester, allyl ester
For amines: Cbz, BOC, DMB
For diols: Ac (×2) TBS (×2), or when taken together acetonides
For thiols: Ac
For benzimidazoles: SEM, benzyl, PMB, DMB
For aldehydes: di-alkyl acetals such as dimethoxy acetal or diethyl acetyl.

In the reaction schemes described herein, multiple stereoisomers may be produced. When no particular stereoisomer is indicated, it is understood to mean all possible stereoisomers that could be produced from the reaction. A person of ordinary skill in the art will recognize that the reactions can be optimized to give one isomer preferentially, or new schemes may be devised to produce a single isomer. If mixtures are produced, techniques such as preparative thin layer chromatography, preparative HPLC, preparative chiral HPLC, or preparative SFC may be used to separate the isomers.

The following abbreviations are used throughout the specification and are defined below:
Ac acetyl
AcOH acetic acid
aq. aqueous
BID or b.i.d. bis in die (twice a day)
BOC tert-butoxy carbonyl
Cbz benzyloxy carbonyl
CDCl$_3$ deuterated chloroform
CH$_2$Cl$_2$ dichloromethane
DCM dichloromethane
DMB 2,4 dimethoxy benzyl
DMF N,N-Dimethylformamide
DMSO Dimethyl sulfoxide
EA or EtOAc Ethyl acetate
EDC or EDCI N-(3-Dimethylaminopropyl)-N'-ethylcarbodiimide
ESI− Electrospray negative mode
ESI+ Electrospray positive mode
EtOH ethanol
h hours
H$_2$O water
HOBt 1-Hydroxybenzotriazole
HCl hydrogen chloride or hydrochloric acid
HPLC High performance liquid chromatography
K$_2$CO$_3$ potassium carbonate
LC/MS or LC-MS Liquid chromatography mass spectrum
M Molar
MeCN Acetonitrile
min minutes
Na$_2$CO$_3$ sodium carbonate
Na$_2$SO$_4$ sodium sulfate
NaHCO$_3$ sodium bicarbonate
NaHMDs Sodium hexamethyldisilazide
NaOH sodium hydroxide
NaHCO$_3$ sodium bicarbonate
Na$_2$SO$_4$ sodium sulfate
NMR Nuclear Magnetic Resonance
Pd(OH)$_2$ Palladium dihydroxide
PMB para methoxybenzyl
p.o. per os (oral administration)
ppm parts per million
prep HPLC preparative High Performance Liquid Chromatography
PYBOP (Benzotriazol-1-yloxy)tripyrrolidinophosphonium hexafluorophosphate
Rt or RT Room temperature
TBME tert-Butyl methyl ether
TFA trifluoroacetic acid
THF tetrahydrofuran
THP tetrahydropyran An effective amount of a compound of the present invention, or a pharmaceutically acceptable salt, solvate or polymorph thereof, is not significantly cytotoxic to normal cells. A therapeutically effective amount of a compound is not significantly cytotoxic to normal cells if administration of the compound in a therapeutically effective amount does not induce cell death in greater than 10% of normal cells. A therapeutically effective amount of a compound does not significantly affect the viability of normal cells if administration of the compound in a therapeutically effective amount does not induce cell death in greater than 10% of normal cells. In a certain aspect, cell death occurs by apoptosis.

Contacting a cell with a compound of the present invention, or a pharmaceutically acceptable salt, solvate or polymorph thereof, may induce or activate cell death selectively in cancer cells. Administering to a subject in need thereof a compound of the present invention, or a pharmaceutically acceptable salt, solvate or polymorph thereof, can induce or activate cell death selectively in cancer cells. Contacting a cell with a compound of the present invention, or a pharmaceutically acceptable salt, solvate or polymorph thereof, may induce cell death selectively in one or more cells affected by a cell proliferative disorder. Preferably, administering to a subject in need thereof a compound of the present invention, or a pharmaceutically acceptable salt, solvate or polymorph thereof, induces cell death selectively in one or more cells affected by a cell proliferative disorder.

One skilled in the art may refer to general reference texts for detailed descriptions of known techniques discussed herein or equivalent techniques. These texts include Ausubel et al., *Current Protocols in Molecular Biology*, John Wiley and Sons, Inc. (2005); Sambrook et al., *Molecular Cloning, A Laboratory Manual* (3$^{rd}$ edition), Cold Spring Harbor Press, Cold Spring Harbor, N.Y. (2000); Coligan et al., *Current Protocols in Immunology*, John Wiley & Sons, N.Y.;

Enna et al., *Current Protocols in Pharmacology*, John Wiley & Sons, N.Y.; Fingl et al., *The Pharmacological Basis of Therapeutics* (1975), *Remington's Pharmaceutical Sciences*, Mack Publishing Co., Easton, Pa., 18th edition (1990). These texts can, of course, also be referred to in making or using an aspect of the invention.

The present invention may also provide pharmaceutical compositions comprising a compound of the present invention, for example Compound A, B, C or D, in combination with at least one pharmaceutically acceptable excipient or carrier.

A "pharmaceutical composition" is a formulation containing the compounds of the present invention in a form suitable for administration to a subject. In one embodiment, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this invention include powders, sprays, ointments, pastes, creams, lotions, gels, solutions, patches and inhalants. In one embodiment, the active compound is mixed under sterile conditions with a pharmaceutically acceptable carrier, and with any preservatives, buffers, or propellants that are required.

As used herein, the phrase "pharmaceutically acceptable" refers to those compounds, materials, compositions, carriers, or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

A compound or pharmaceutical composition of the invention can be administered to a subject in many of the well-known methods currently used for chemotherapeutic treatment. For example, for treatment of cancer(s), a compound of the invention may be injected directly into tumors, injected into the blood stream or body cavities or taken orally or applied through the skin with patches. The dose chosen should be sufficient to constitute effective treatment but not as high as to cause unacceptable side effects. The state of the disease condition (e.g., cancer, precancer, and the like) and the health of the patient should preferably be closely monitored during and for a reasonable period after treatment.

The term "therapeutically effective amount", as used herein, refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic selected for administration. Therapeutically effective amounts for a given situation can be determined by routine experimentation that is within the skill and judgment of the clinician. In a preferred aspect, the disease or condition to be treated is cancer. In another aspect, the disease or condition to be treated is a cell proliferative disorder.

For any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans.

In embodiments of the invention the EZH2 inhibitors are administered at dose of 100-1600 mg/kg. In embodiments the dose is 100 mg/kg, or 200 mg/kg, or 400 mg/kg, or 800 mg/kg or 1600 mg/kg. In certain embodiments the dose is administered once a day, or twice a day. In embodiments the EZH2 inhibitor is Compound A and the dose is twice a day 100 mg/kg, or 200 mg/kg, or 400 mg/kg, or 800 mg/kg or 1600 mg/kg. In a preferred embodiment the EZH2 inhibitor is Compound A and the dose is 800 mg/kg twice a day.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug interaction(s), reaction sensitivities, and tolerance/response to therapy. Long-acting pharmaceutical compositions may be administered every 3 to 4 days, every week, or once every two weeks depending on half-life and clearance rate of the particular formulation.

The pharmaceutical compositions containing active compounds of the present invention may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients or auxiliaries (or both) that facilitate processing of the active compounds into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol and sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents or adjuvant materials, or both, can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The active compounds can be prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved.

In therapeutic applications, the dosages of the pharmaceutical compositions used in accordance with the invention vary depending on the agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the growth of the tumors and also preferably causing complete regression of the cancer. Dosages can range from about 0.01 mg/kg per day to about 5000 mg/kg per day. In preferred aspects, dosages can range from about 1 mg/kg per day to about 1000 mg/kg per day. In a certain aspect, the dose will be in the range of about 0.1 mg/day to about 50 g/day; about 0.1 mg/day to about 25 g/day; about 0.1 mg/day to about 10 g/day; about 0.1 mg to about 3 g/day; or about 0.1 mg to about 1 g/day, in single, divided, or continuous doses (which dose may be adjusted for the patient's weight in kg, body surface area in $m^2$, and age in years). An effective amount of a pharmaceutical agent is that which provides an objectively identifiable improvement as noted by the clinician or other qualified observer. For example, regression of a tumor in a patient may be measured with reference to the diameter of a tumor. Decrease in the diameter of a tumor indicates regression. Regression is also indicated by failure of tumors to reoccur after treatment has stopped. As used herein, the term "dosage effective manner" refers to amount of an active compound to produce the desired biological effect in a subject or cell.

The pharmaceutical compositions can be included in a container, pack, or dispenser together with instructions for administration.

The compounds of the present invention are capable of further forming salts.

As used herein, "pharmaceutically acceptable salts" refer to salts of the compounds of the present invention wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

Other examples of pharmaceutically acceptable salts include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The present invention also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

The compounds, or pharmaceutically acceptable salts, solvates or polymorphs thereof, are administered orally, nasally, transdermally, pulmonary, inhalationally, buccally, sublingually, intraperintoneally, subcutaneously, intramuscularly, intravenously, rectally, intrapleurally, intrathecally and parenterally. In one embodiment, the compound is administered orally. One skilled in the art will recognize the advantages of certain routes of administration.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Techniques for formulation and administration of the disclosed compounds of the invention can be found in *Remington: the Science and Practice of Pharmacy*, $19^{th}$ edition, Mack Publishing Co., Easton, Pa. (1995). In an embodiment, the compounds described herein, and the pharmaceutically acceptable salts thereof, are used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein.

All percentages and ratios used herein, unless otherwise indicated, are by weight. Other features and advantages of the present invention are apparent from the different examples. The provided examples illustrate different components and methodology useful in practicing the present invention. The examples do not limit the claimed invention. Based on the present disclosure the skilled artisan can identify and employ other components and methodology useful for practicing the present invention.

In the synthetic schemes described herein, compounds may be drawn with one particular configuration for simplicity. Such particular configurations are not to be construed as limiting the invention to one or another isomer, tautomer, regioisomer or stereoisomer, nor does it exclude mixtures of isomers, tautomers, regioisomers or stereoisomers.

Additional compounds suitable for the methods of the invention, as well as pharmaceutical compositions and uses thereof, are described in WO12/142504 and WO12/142513, the contents of each of which are hereby incorporated by reference in their entireties.

Posttranslational modification of histone proteins and ATP-dependent chromatin remodeling are crucial processes for the regulation of the fidelity of normal gene expression. Proteins involved in these processes, such as the PRC2 and SWI/SNF complexes are often genetically altered in cancer. Importantly, these two complexes normally compete with each other in binding to and affecting chromatin; genetic alterations can create an imbalance in this antagonism. For instance, INI1 is a subunit of the SWI/SNF complex that is lost in nearly all rhabdoid tumors, which creates an oncogenic dependency on the PRC2-EZH2 methyltransferase, and rhabdoid tumor models are sensitive to EZH2 small molecule inhibitors. In synovial sarcoma, another INI1-deficient tumor type, a recurrent chromosomal translocation fuses the SS18 gene (a subunit of the SWI/SNF chromatin remodeling complex) on chromosome 18 to one of three related genes on the X chromosome, SSX1, SSX2 and rarely SSX4. This results in the expression of an oncogenic SS18-SSX fusion protein that binds to the SWI/SNF complex evicting both the wild-type SS18 and the tumor suppressor INI1, which are subsequently degraded. This results in aberrant gene expression and ultimately the development of cancer.

Described herein is data showing that Compound A (also referred to herein as E7438 or EPZ-6438), an early clinical-stage, selective and orally bioavailable small-molecule inhibitor of EZH2 enzymatic activity induces anti-proliferative activity in preclinical models of synovial sarcoma both as a single agent and in combination with chemotherapy. The compound induces dose-dependent cell growth inhibition and cell death specifically in a synovial sarcoma cell line (which is SS18-SSX1 fusion-positive) in vitro. Treatment of mice bearing either a cell line xenograft or two patient-derived xenograft (PDX) models leads to dose-dependent tumor growth inhibition with correlative inhibition of trimethylation levels of the EZH2-specific substrate, lysine 27 on histone H3. These data demonstrate a dependency of SS18-SSX1-positive synovial sarcomas on EZH2 enzymatic activity in xenograft models and suggests the potential utility of EZH2-targeted drugs in these genetically defined cancer(s) with the appropriate biomarker.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

EXAMPLES

Example 1: The Protein Levels of EZH2, INI1, SS18-SSX1 and Loading Control β-Actin in Various Cell Lines HS-SY-II and SW982 human synovial sarcoma cells, RD human rhabdomyosarcoma cells, G401 human rhabdoid tumor cells, and HEK293 human embryonic kidney cells were lysed with 1× Cell Lysis Buffer (#9803, Cell Signaling Technology, Danvers, Mass.) containing 1× protease inhibitor cocktail (Thermo Scientific, Rockford, Ill.). The samples were sonicated and clarified by centrifugation at 10,000×g for 10 minutes at 4° C. The protein content of the lysates was determined by using a BCA Protein Assay Kit (Thermo Scientific). A sample solution was prepared by mixing 2× loading buffer (β-ME Sample Treatment for Tris SDS, Cosmo bio, Tokyo, Japan) and water with cell lysate and incubated for 5 minutes at 95° C. Western blot analysis was performed as follows. The sample solutions were separated on 2-15% gradient polyacrylamide gel for SS18 and EZH2 or 4-20% gradient polyacrylamide gel for INI1 and β-actin under reducing conditions and transferred to nitrocellulose membranes (GE Healthcare, Waukesha, Wis.). The blots were blocked with the following blocking solutions for 1 hour at room temperature: 1× Block Ace solution (Yukijirushi, Sapporo, Japan) for EZH2, INI1 and SS18, and TBS containing 0.5% Tween 20 and 5% Skim milk for β-actin. The blots were incubated with the primary antibodies overnight at 4° C. with the following dilution conditions: EZH2 antibody (07-689, Millipore, Billerica, Mass.) at 1:1000 dilution in TBS containing 0.5% Tween 20 and 0.1× Block Ace solution, INI1 antibody (#8745, Cell Signaling Technology) at 1:1000 dilution in TBS containing 0.5% Tween 20 and 0.1× Block Ace solution, SS18 antibody (sc-365170, Santa Cruz, Santa Cruz, Calif.) at 1:500 dilution in TBS containing 0.5% Tween 20 and 0.1× Block Ace solution, and β-actin antibody (A5441, Sigma-Aldrich, St. Louis, Mo.) at 1:2000 dilution in TBS containing 0.5% Tween 20 and 5% Skim milk. After washing with TBS containing 0.5% Tween 20, the blots were further incubated with horseradish peroxidase conjugated anti-rabbit IgG (Cell Signaling Technology) or anti-mouse IgG (Cell Signaling Technology) at room temperature for 60 minutes with the following dilution conditions: 1:1000 dilution of anti-rabbit IgG in TBS containing 0.5% Tween 20 and 0.1× Block Ace solution for EZH2, INI1 and SS18, and 1:2000 dilution of anti-mouse IgG in TBS containing 0.5% Tween 20 and 5% Skim milk for β-actin. After extensive washing by TBS containing 0.5% Tween 20, blots were developed with Immobilon Western chemiluminescent HRP substrate (Millipore). Immunoreactive bands were visualized by chemiluminescence with Luminescent Image Analyzer LAS-3000 (Fuji Film, Tokyo, Japan). The representative images of the western blot are shown in FIG. 1. SS18-SSX1 expression was confirmed in HS-SY-II cells. INI1 down-regulation was also observed in the cell line. On the other hand, another synovial sarcoma line SW982 did not express the fusion protein and had equivalent expression of INI1 to those of RD and HEK293 cells.

Figure 2A:
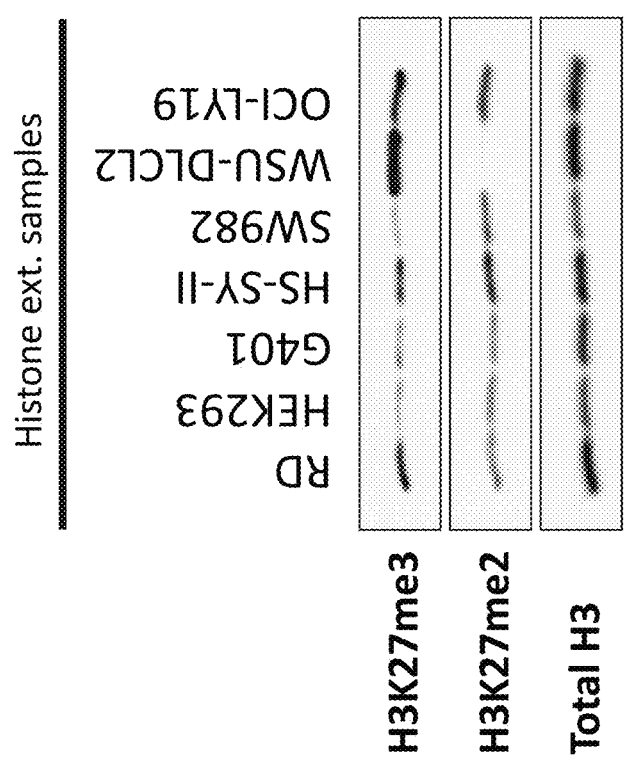
FIG. 2A is a western blot of isolated histones showing H3K27 trimethylation (H3K27me3) and H3K27 dimethylation (H3K27me2) levels in various cell lines.
Figures 3A, 3B:
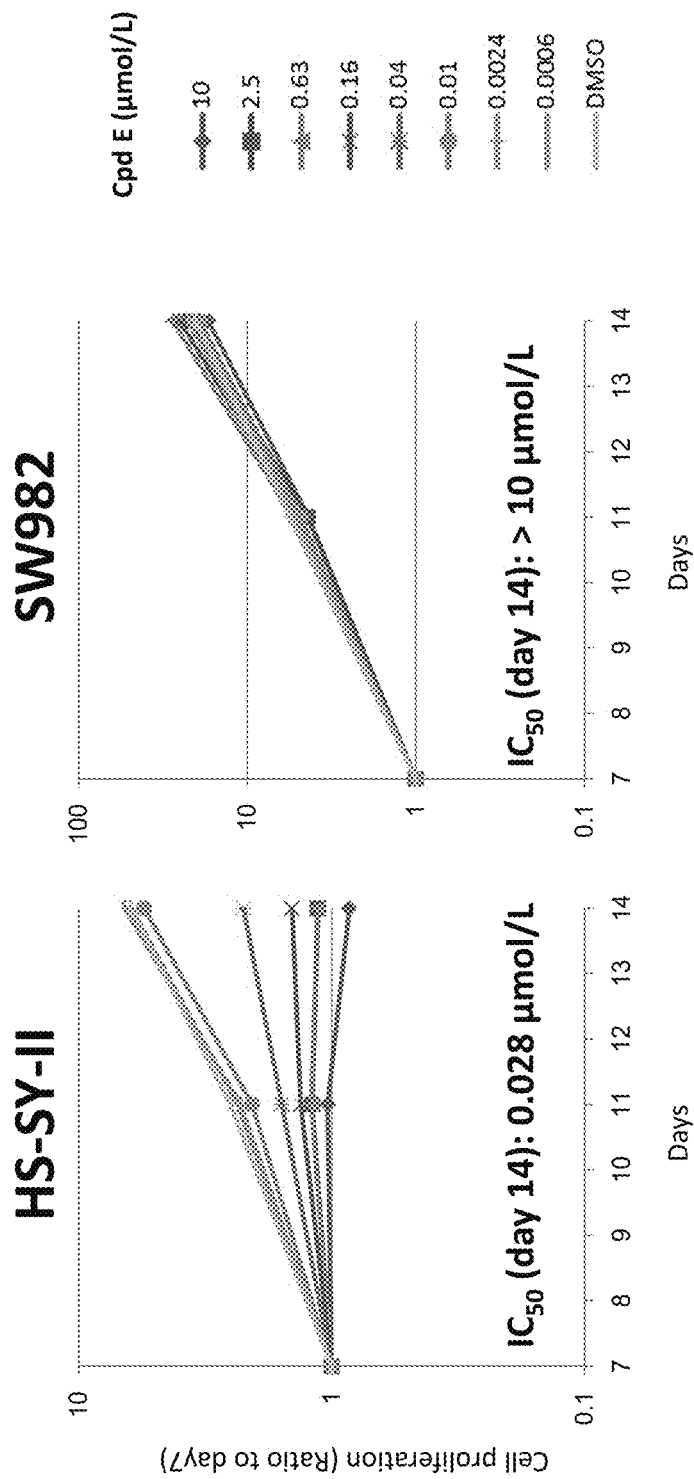
FIGS. 3A to 3D are series of plots showing that HS-SY-II cells are highly sensitive to the EZH2 inhibitors, while SW982 cells are not. Cell line HS-SY-II shown in FIG. 3A and cell line SW982 shown in FIG. 3B were treated with Compound E. Cell line HS-SY-II shown in FIG. 3C and cell line SW982 shown in FIG. 3D were treated with Compound A (also referred to herein as E7438 or EPZ-6438). Each type of cells was pre-treated with a compound (Compound E or Compound A) for 7 days with indicated concentrations and re-plated and treated for an additional 7 days. Cell viability was determined by CellTiter-Glo® Luminescent Cell Viability Assay.
Figures 3C, 3D:
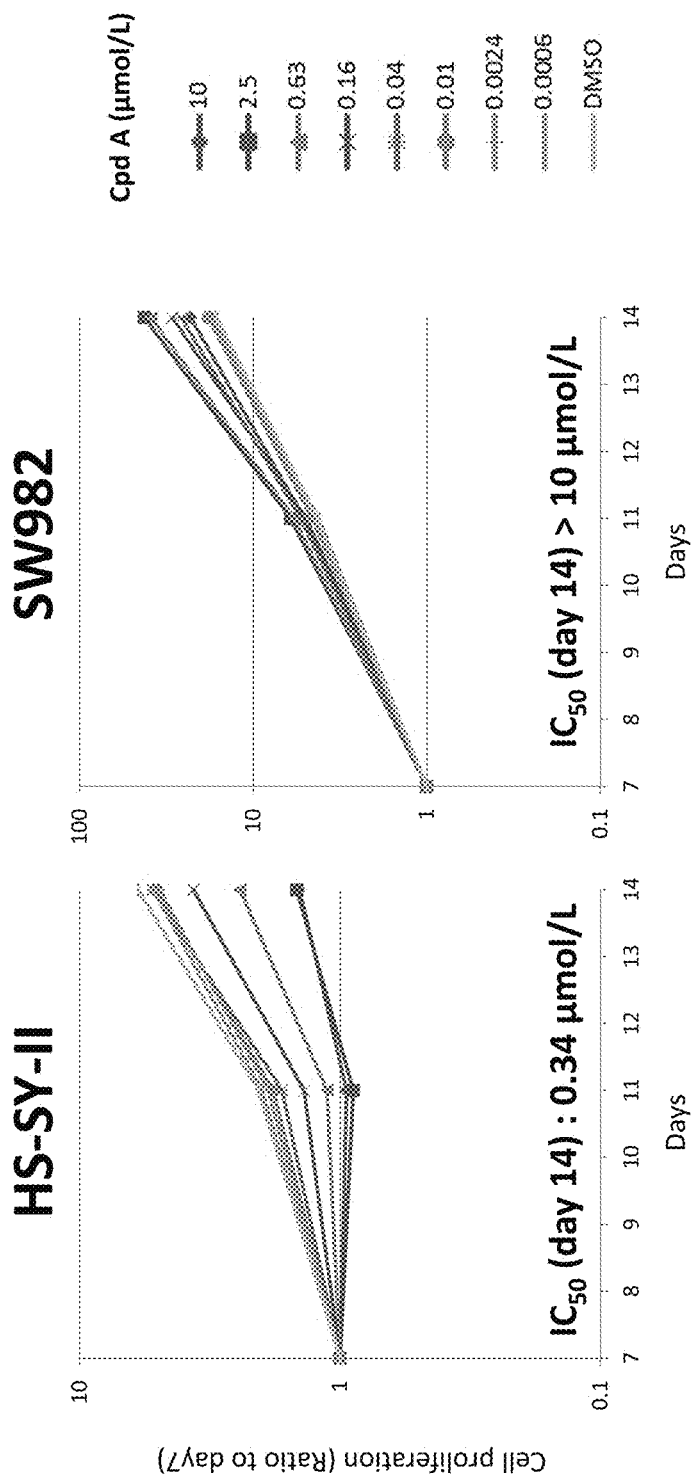
Figure 4A:
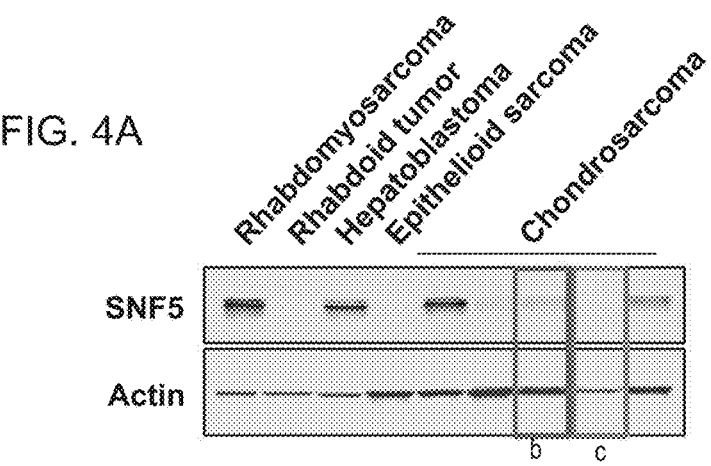
FIGS. 4A to 4F demonstrate that reduction of INI1 levels confers sensitivity to EZH2 inhibitor (EZH2i) in soft tissue sarcoma cell lines. (A) is a Western blot of cell lysates showing INI1 expression in different tumor cell lines. Tumor cell lines of chondrosarcoma showed down-regulation of INI1 (for example in cell lines b and c). (B) and (C) are graphs demonstrating that cell line b (graph B) and cell line c (graph C) are sensitive to EZH2 inhibitors. (D) is a Western blot of cell lysates showing INI1 and SS18 expression in different cell lines. (E) is a graph showing that the SSX-SS18 positive cells are sensitive to EZH2 inhibitors. (F) is a graph showing that the SSX-SS18 negative cells are not sensitive to EZH2 inhibitors.
Figure 4B:
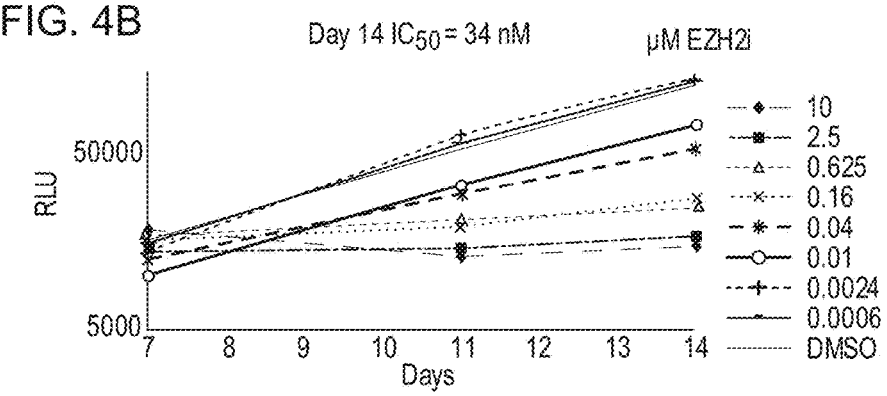
Figure 4C:
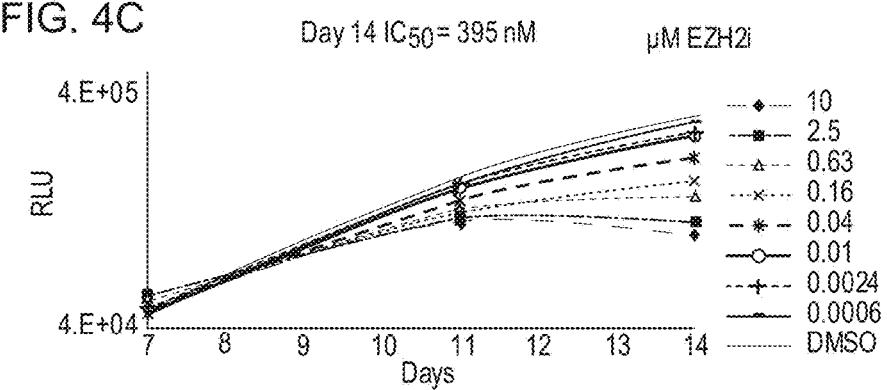
Figure 4D:
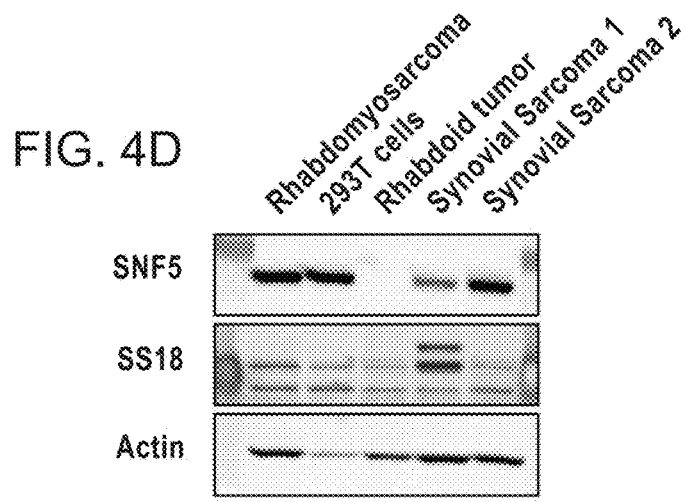
Figure 4E:
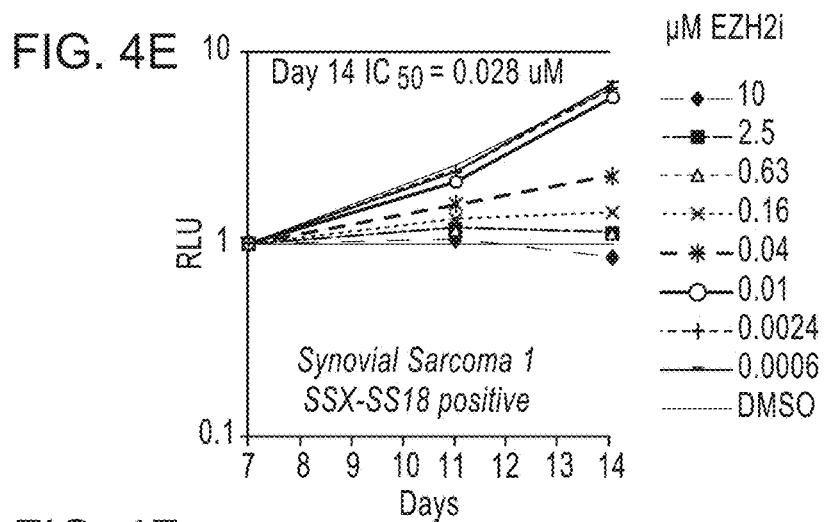
Figure 4F:
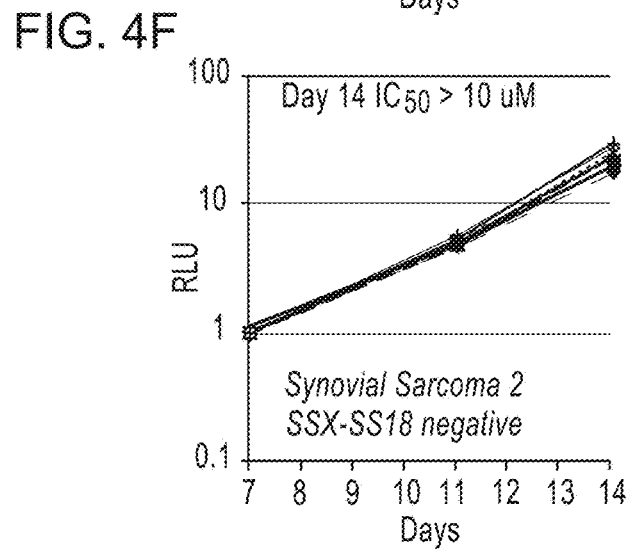

Example 2: Trimethylation and Dimethylation Levels of H3K27 in Various Cell Lines HS-SY-II and SW982 human synovial sarcoma cells, RD human rhabdomyosarcoma cells, G401 human rhabdoid tumor cells, WSU-DLCL2 and OCI-LY19 human diffuse large B-cell lymphoma cells and HEK293 human embryonic kidney cells were suspended in 500 μL of lysis buffer (10 mmol/L $MgCl_2$, 10 mmol/L Tris-HCl, 25 mmol/L KCl, 1% Triton X-100, 8.6% sucrose, and 1× protease inhibitor cocktail). After 5 minute incubation on ice, nuclei were collected by centrifugation at 600×g for 5 minutes at 4° C. and washed once with ice-cold PBS. After centrifugation at 600×g for 5 minutes at 4° C., the pellet was resuspended in 100 μL of 0.2 mol/L ice-cold sulfuric acid for 1 hour with vortex for several times during the incubation. Supernatant was clarified by centrifugation at 10,000×g for 10 minutes at 4° C. and 1 mL of ice-cold acetone was added to the collected supernatant. Histones were precipitated at −20° C. for 1 hour, pelleted by centrifugation at 10,000×g for 10 minutes at 4° C. and resuspended in 100 μL of water. Extracted histones were quantified using the BCA protein assay kit (Pierce). A sample solution was prepared by mixing 2× loading buffer (β-ME Sample Treatment for Tris SDS, Cosmo bio) and water with cell lysate and incubated for 5 minutes at 95° C. Western blot analysis was performed as follows. The sample solutions were separated on 15-25% gradient polyacrylamide gel under reducing conditions and transferred to nitrocellulose membranes (GE Healthcare, Waukesha, Wis.). The blots were blocked for 1 hour at room temperature with the following blocking solution: 1× Block Ace solution for H3K27me3 and H3K27me2, and TBS containing 0.5% Tween 20 and 5% Skim milk for total histone H3. The blots were incubated with the primary antibodies overnight at 4° C. with the following dilution conditions: H3K27me3 antibody (#9733, Cell Signaling Technology) and H3K27me2 antibody (#9728, Cell Signaling Technology) at 1:1000 dilution in TBS containing 0.5% Tween 20 and 0.1× Block Ace solution, and total histone H3 antibody (ab1791, Abcam, Cambridge, Mass.) at 1:2000 dilution in TBS containing 0.5% Tween 20 and 5% Skim milk. After washing with TBS containing 0.5% Tween 20, the blots were further incubated with horseradish peroxidase conjugated anti-rabbit IgG (Cell Signaling Technology) at room temperature for 60 minutes with 1:1000 dilution in TBS containing 0.5% Tween 20 and 0.1× Block Ace solution for H3K27me3 and H3K27me2, or with 1:2000 dilution in TBS containing 0.5% Tween 20 and 5% Skim milk for total histone H3. After extensive washing by TBS containing 0.5% Tween 20, blots were developed with Immobilon Western chemiluminescent HRP substrate (Millipore). Immunoreactive bands were visualized by chemiluminescence with Luminescent Image Analyzer LAS-3000 (Fuji Film, Tokyo, Japan). The representative images of the western blot are shown in FIG. 2A. The signals of protein bands were quantified using Multi Gauge version 3.0 software (Fuji Film). A series of plots showing quantitative H3K27me3/total H3 (FIG. 2B), H3K27me2/total H3 (FIG. 2C) or H3K27me3/H3K27me2 (FIG. 2D) ratio in various cell lines are shown. In contrast to high H3K27me3/H3K27me2 status in WSU-DLCL2 harboring an Y646 EZH2 mutation, HS-SY-II did not show high H3K27me3/H3K27me2 status.

Example 3: Adherent Cell Line Long-Term Proliferation Assay

Protocol:

96-well plating for 7 day assay: For each adherent cell line, plated cells in a volume of 100 µL in 96-well plates, to be treated in triplicate, either in the evening (to treat with compound the following day) or in morning (to treat with compound in the evening), to allow cells to attach to plates before compound treatment.

6-well plates to be split for 7-14 day assay: Plated 2 mL of cells at the correct density in each well of the 6-well plate. Calculated the correct density from the 96-well plate growth curve by multiplying the 96-well density by 30. The factor 30 came from growth area of the 6-well plate divided by the growth area of the 96-well plate (9.5 cm$^2$/0.32 cm$^2$=29.7, rounded up to 30), which corresponds to 30-fold more surface area in a 6-well vs. a 96-well plate.

Day 0: Treated with compound or DMSO by removing media and adding back either 100 µL (for 96-well plate) or 2 mL (for 6-well plate) media with the correct dilutions of compound/DMSO. Table 1 includes an example of 96-well plate map. Plates were incubated for 96 hours.

Read one 96-well plate with CellTiter-Glo® for a Day 0 reading (media change not necessary for this plate).

Day 4: Read one 96-well plate with CellTiter-Glo® for a Day 4 reading (media change not necessary for this plate before reading). Replaced media with fresh media containing compound on Day 4 in 96-well plates and 6-well plates.

Day 7: read final 96-well plate with CellTiter-Glo®.

Counted individual wells of 6-well plates, and replated cells to initial plating density in 96-well plates, as described above.

Repeated steps for Days 0-7 for Days 7-14 of the proliferation assay.

Particularly, approximately 12 hours before compound treatment, HS-SY-II or SW982 cells were plated at the density of 24,000 cells/well and 7,500 cells/well, respectively in 6-well plates. On day 0, cells were treated with either DMSO or compound starting at 10 µmol/L and decreasing in fourfold dilutions. On day 7, the cells in 6-well plates were trypsinized, counted by TC10 automated cell counter (Bio-Rad, Richmond, Calif.) and replated at the density of 800 cells/well and 250 cells/well for HS-SY-II and SW982, respectively in 96-well plates in triplicate. The cells were allowed to adhere to the plate overnight, and treated with either DMSO or compound as on Day 0. On days 0, 7, 11, and 14, cell viability was determined by CellTiter-Glo® Luminescent Cell Viability Assay (Promega) with EnVision 2103 Multilabel Reader (Perkin-Elmer, Wellesley, Mass.). Compound/media was changed with new one on Day 4 and 11. The ratios of the measured values on Days 7, 11, and 14 to that of day 7 were used to plot proliferation from day 7 to day 14, and to calculate the IC$_{50}$ values on Day 14. The representative graphs of experiments using Compound E and Compound A (also referred to herein as E7438 and EPZ-6438) were shown in FIGS. 3A, 3B and 3C, 3D, respectively. HS-SY-II cells showed high sensitivity to Compound E and Compound A in the 14-day long-term proliferation assay, while SW982 cells did not.

Example 4: Compound a Treatments In Vitro and In Vivo

In vitro, HS-SY-II cells are highly sensitive to Compound A and show inhibition of cell proliferation in a dose-dependent manner. On the other hand, SW982 cells are not sensitive to Compound A (FIGS. 5A and 5B).

Figures 6A, 6B:
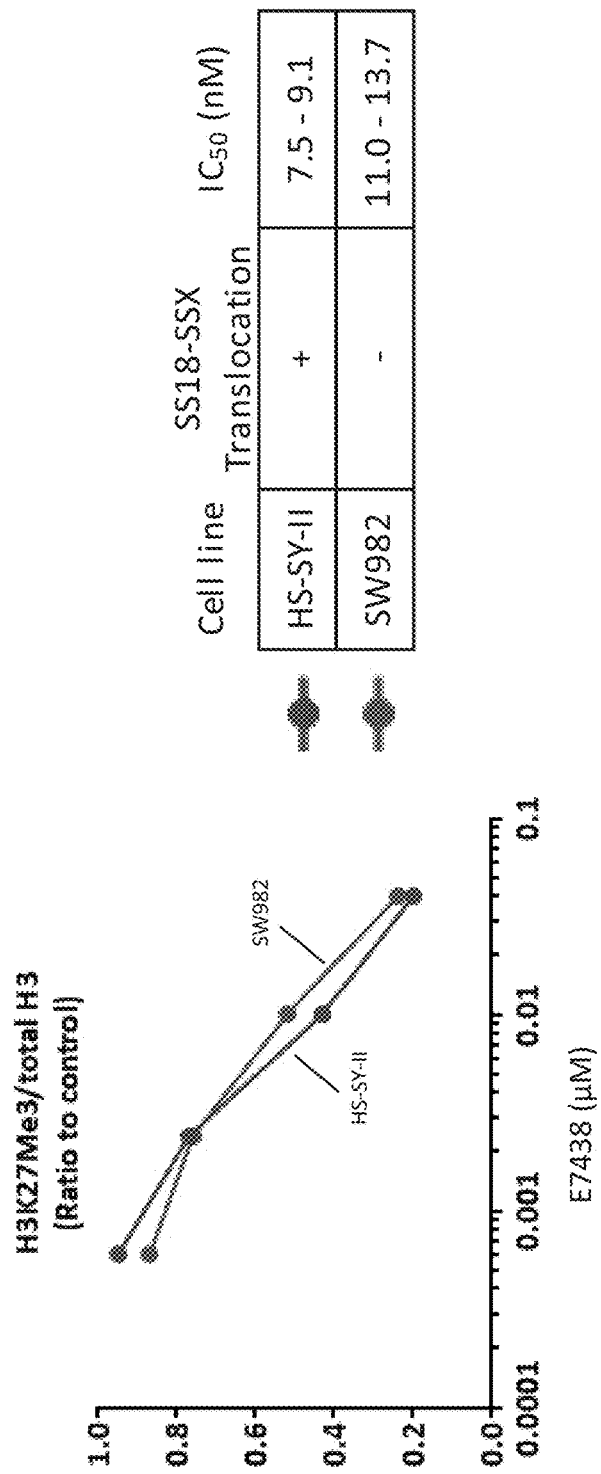
FIG. 6A shows decreased ratios of H3K27me3/total H3 (ratio to control) in HS-SY-II and SW982 cells after treatment with Compound A. Cells were treated with Compound A for 96 hours and histone were extracted. Histone mark alterations were analyzed by Enzyme-Linked Immunosorbent Assay (ELISA). Histone mark alterations were comparable between HS-SY-II and SW982, suggesting the alterations were independent of the presence of SS18-SSX fusion protein.
FIG. 6B shows the concentration ($IC_{50}$) of the compound necessary to inhibit the ratio of H3K27me3/total H3 by 50%.

Reduction in H3K27me3 was observed in both cell lines by the treatment with EZH2 inhibitor (FIG. 6A) and the IC$_{50}$ values were comparable to each other (FIG. 6B). This suggests that the histone mark alterations by the treatment with EZH2 inhibitor were independent of the presence of SS18-SSX fusion protein.

Figures 7A, 7B:
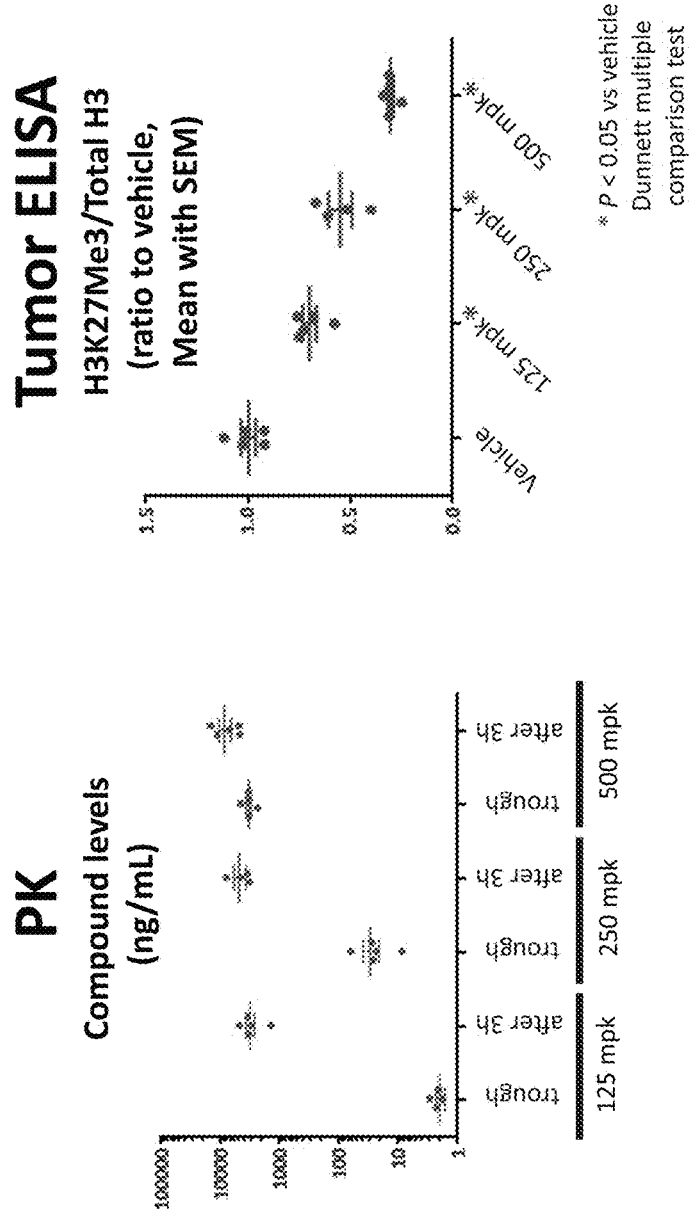
FIGS. 7A and 7B show pharmacokinetic (PK) values and pharmacodynamic (PD) alterations, respectively, in an HS-SY-II xenograft model.

PK values and PD alterations were analyzed in HS-SY-II xenograft mouse model. The plasma concentrations of Compound A at 5 minutes before and 3 hours after the last dose were determined. Dose dependent exposure was observed (FIG. 7A). At the same time, dose dependent decrease of H3K27me3 levels in tumor tissues was also observed (FIG. 7B). Tables 2 and 3 provide statistical analyses related to the data shown in FIG. 7B.

TABLE 1

| A | | | | | | | | | | | | |
|---|---|---|---|---|---|---|---|---|---|---|---|---|
| 1 | 2 | 3 | 4 | 5 | 6 | 7 | 8 | 9 | 10 | 11 | 12 | |
| B | Naïve | 10 | 2.5 | 0.63 | 0.16 | 0.04 | 0.01 | 0.0024 | 0.0006 | DMSO | | |
| C | Naïve | 10 | 2.5 | 0.63 | 0.16 | 0.04 | 0.01 | 0.0024 | 0.0006 | DMSO | | |
| D | Naïve | 10 | 2.5 | 0.63 | 0.16 | 0.04 | 0.01 | 0.0024 | 0.0006 | DMSO | | |
| E | | Compound | Dilutions | — | — | — | — | — | —> | | | |
| F | | | | | | | | | | | | |
| G | | | | | | | | | | | | |
| H | | | | | | | | | | | | |

TABLE 2

| | | | | |
|---|---|---|---|---|
| Number of families | 1 | | | |
| Number of comparisons per family | 3 | | | |
| Alpha | 0.05 | | | |

| Dunnett's multiple comparisons test | Mean Diff. | 95% CI of diff. | Significant | Summary |
|---|---|---|---|---|
| Vehicle vs. E7438 125 mg/kg | 0.3 | 0.1681 to 0.4319 | Yes | **** |
| Vehicle vs. E7438 250 mg/kg | 0.45 | 0.3101 to 0.5899 | Yes | **** |
| Vehicle vs. E7438 500 mg/kg | 0.696 | 0.5641 to 0.8279 | Yes | **** |

| Test details | Mean 1 | Mean 2 | Mean Diff. | SE of diff. | n1 | n2 | q | DF |
|---|---|---|---|---|---|---|---|---|
| Vehicle vs. E7436 125 mg/kg | 1 | 0.7 | 0.3 | 0.05052 | 5 | 5 | 5.938 | 15 |
| Vehicle vs. E7438 250 mg/kg | 1 | 0.55 | 0.45 | 0.05359 | 5 | 4 | 8.398 | 15 |
| Vehicle vs. E7438 500 mg/kg | 1 | 0.304 | 0.696 | 0.05052 | 5 | 5 | 13.78 | 15 |

TABLE 3

| Post test for linear trend | |
|---|---|
| Slope | −0.1119 |
| R squared | 0.9104 |
| P value | <0.0001 |
| P value summary | **** |
| Is linear trend significant (P < 0.05)? | Yes |

Figure 8:
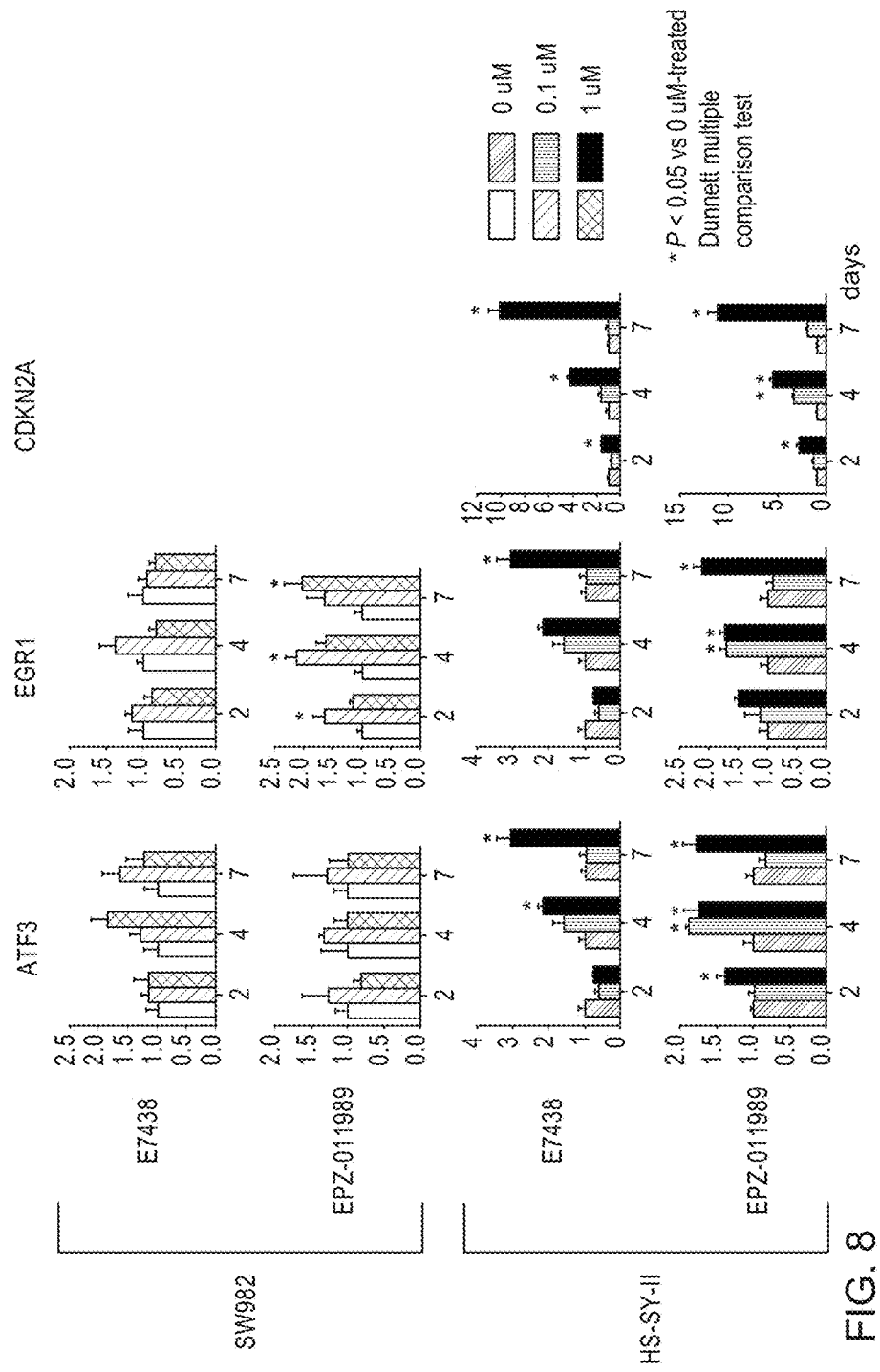
FIG. 8 shows expression changes of putative PD markers after Compound A treatment in HS-SY-II and SW982 in in vitro experiments. Here, each cell type was treated with Compound A or EPZ-011989 (which is also an EZH2 inhibitor and also referred herein as Compound C); the concentration and period (days) are shown. Gene expression alterations were analyzed by RT-PCR. Gene expression levels were normalized to GAPDH levels. The bars are shown as ratio to 0 μM-treated controls. Table 4 below provides a statistical analysis related to the data shown in FIG. 8. Asterisks mean significant changes compared to levels of 0 μM-treated groups.

Gene expression changes by the treatment with Compound A or EPZ-011989 (i.e., Compound C) were analyzed in HS-SY-II and SW982 in in vitro cultures. It has been reported that PRC2 complex is recruited to SS18-SSX fusion protein by TLE1 and represses ATF2 target genes (EGR1, ATF3, MEIS2 and CDKN2A) (*Cancer Cell* 21, 333-347, 2012). Expression levels of EGR1, ATF3, and CDKN2A were here examined. Dose- and time-dependent CDKN2A upregulation was observed in HS-SY-II, while CDKN2A locus is known to be homozygously deleted in SW982 (FIG. 8). ATF3 and EGR1 were upregulated by the treatment with Compound A and EPZ-011989 in HS-SY-II but not in SW982. Thus, Compound A induces changes in the expression of genes implicated in synovial sarcoma pathogenesis.

Table 4 provides a statistical analysis related to the data shown in FIG. 8.

TABLE 4

| | | | | 0 uM vs. | day2 | day4 | day7 |
|---|---|---|---|---|---|---|---|
| SW 982 | E7438 | ATF3 | | 0.1 uM | ns | ns | ns |
| | | | | 1 uM | ns | ns | ns |
| | | EGR1 | | 0.1 uM | ns | ns | ns |
| | | | | 1 uM | ns | ns | ns |
| | EPZ011989 | ATF3 | | 0.1 uM | ns | ns | ns |
| | | | | 1 uM | ns | ns | ns |
| | | EGR1 | | 0.1 uM | * | ** | ns |
| | | | | 1 uM | ns | ns | * |
| HS-SY-II | E7438 | ATF3 | | 0.1 uM | ns | ns | ns |
| | | | | 1 uM | ns | * | ** |
| | | EGR1 | | 0.1 uM | ns | ns | ns |
| | | | | 1 uM | ns | ns | ** |
| | | CDKN2A | | 0.1 uM | ns | ns | ns |
| | | | | 1 uM | ** | **** | **** |
| | EPZ011989 | ATF3 | | 0.1 uM | ns | ** | ns |
| | | | | 1 uM | * | * | ** |
| | | EGR1 | | 0.1 uM | ns | ** | ns |
| | | | | 1 uM | ns | ** | ** |
| | | CDKN2A | | 0.1 uM | ns | **** | ns |
| | | | | 1 uM | *** | **** | **** |

Asterisks mean significant changes compared to levels of 0 μM-treated groups.

Figure 9:
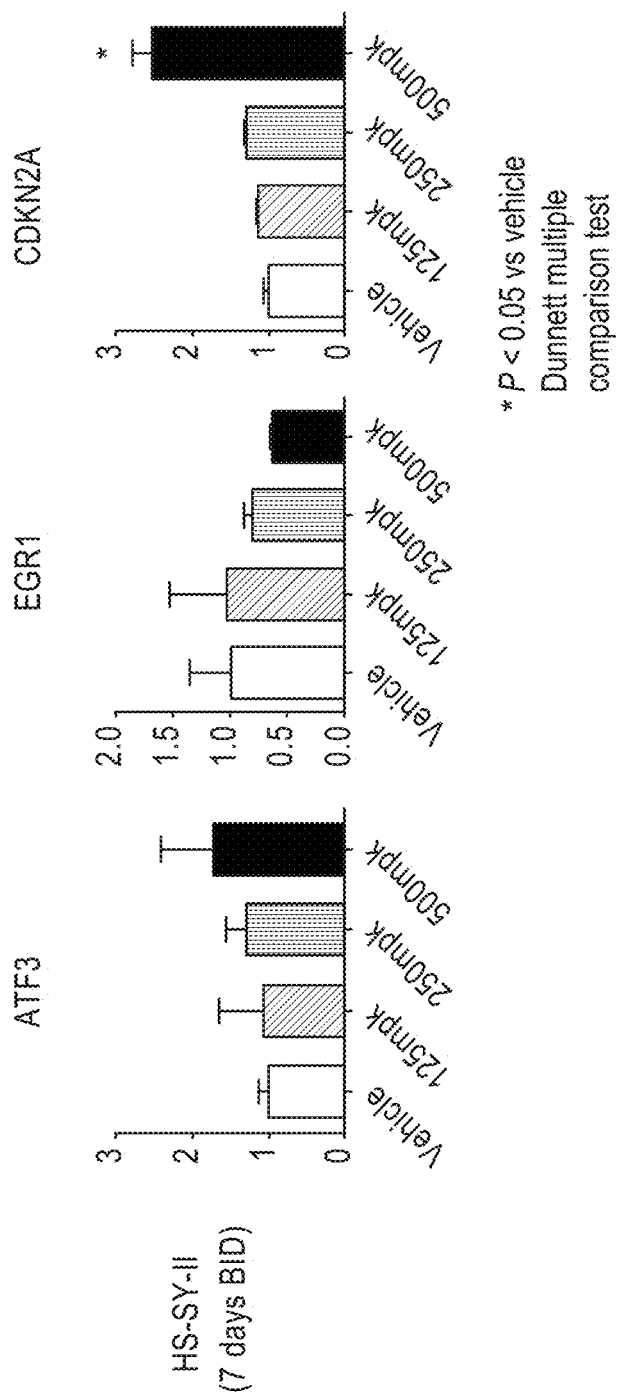
FIG. 9 shows expression changes of putative PD markers after Compound A treatment in HS-SY-II in an in vivo experiment. Here, Compound A was given orally to mice twice daily for 7 days. Tumor samples were collected at approximately 3 hours after the last dose. Gene expression alterations were analyzed by RT-PCR. Gene expression levels were normalized to GAPDH levels. The bars are shown as ratios to data of vehicle group.

Gene expression changes by the treatment with Compound A were analyzed also in HS-SY-II xenograft model. CDKN2A was significantly upregulated in mice dosed with 500 mg/kg Compound A (FIG. 9). Again, Compound A induces changes in the expression of genes implicated in synovial sarcoma pathogenesis.

Figure 10B:
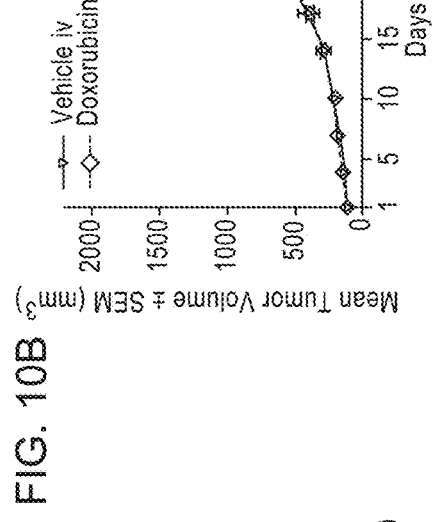
FIGS. 10A to 10C show mean tumor volumes for athymic nude mice bearing HS-SY-II xenografts that were dosed with either vehicle (oral or iv), Compound A (oral), Doxorubicin (iv), or an Compound A/Doxorubicin combination at the indicated doses for 28 days. Tumor volumes were measured twice a week. Two independent studies were performed.
Figure 10A:
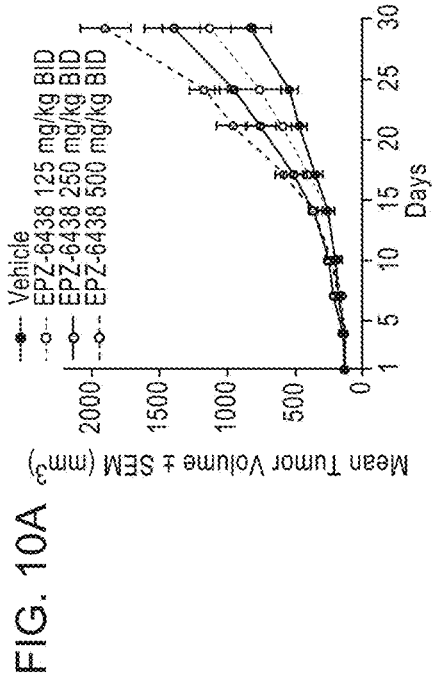
Figure 10C:
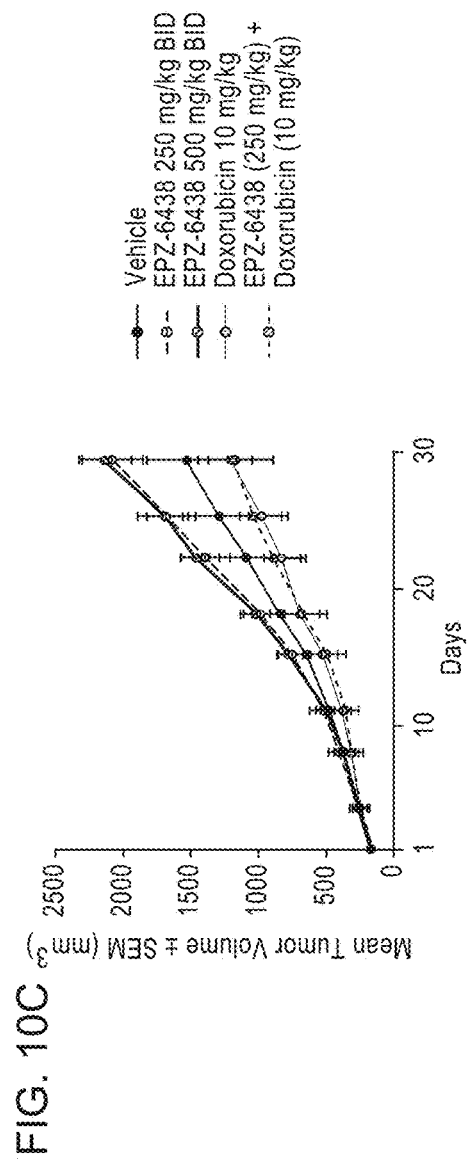

FIGS. 10A to 10C show mean in vivo tumor volumes for athymic nude mice bearing HS-SY-II xenografts. In a first study, mice were dosed with either vehicle (oral for 28 days or iv on Day 1 and Day 22), Compound A (oral: 125 mg/kg, 250 mg/kg, or 500 mg/kg for 28 days), or Doxorubicin (iv: 10 mg/kg, Day 1 and Day 22); tumor volumes were measured twice a week (FIGS. 10A and 10B). In a second study, mice were dosed with either vehicle (oral for 28 days), Compound A (oral: 250 mg/kg or 500 mg/kg for 28 days), Doxorubicin (iv: 10 mg/kg on Day 1 and Day 22), or a combination of Doxorubicin (iv: 10 mg/kg on Day 1 and Day 22) and Compound A (oral: 250 mg/kg for 28 days) (FIG. 10C). Tumors from animals of the second study were harvested on Day 28 (3 h after the last dose) and subjected to H3K27me3 analysis by ELISA (FIG. 10D) or IHC for the proliferation marker Ki67 (FIG. 10E).

Although sensitive to Compound A in 2D cell culture, HS-SY-II cell line xenografts exhibited dose-related tumor volume increase in a mouse xenograft model; the mechanism underlying this observation is being investigated.

Figure 11A:
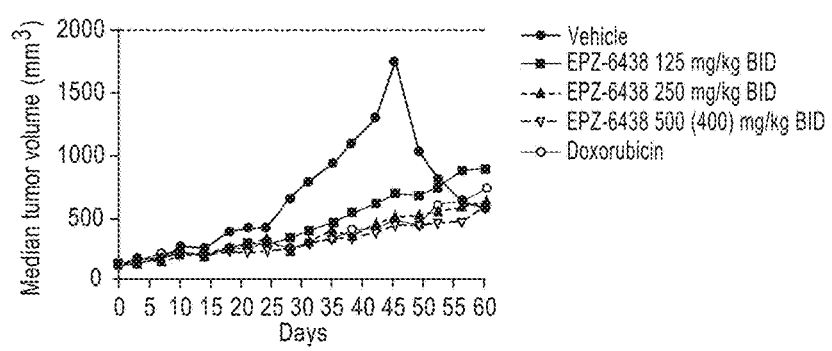
FIGS. 11A to 11D show mean tumor volumes and percent survival for athymic nude mice bearing two different patient-derived xenografts (PDX) of synovial sarcoma tumors and were dosed with either vehicle (oral), Compound A (oral) or Doxorubicin (iv) at the indicated doses for 35 days.
Figure 11B:
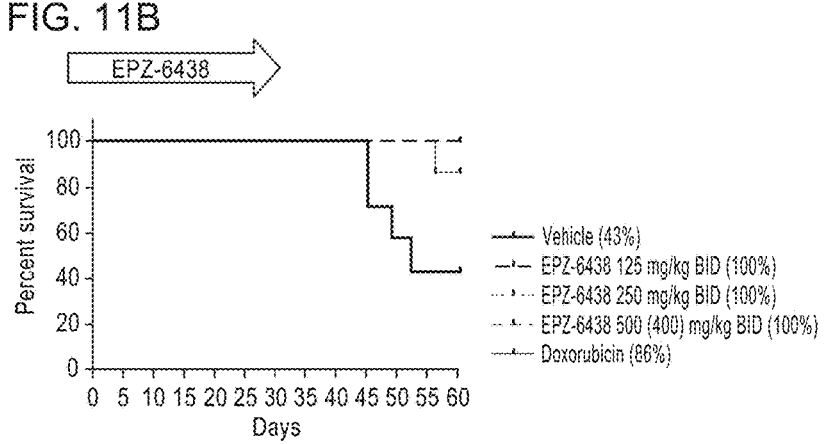
Figure 11C:
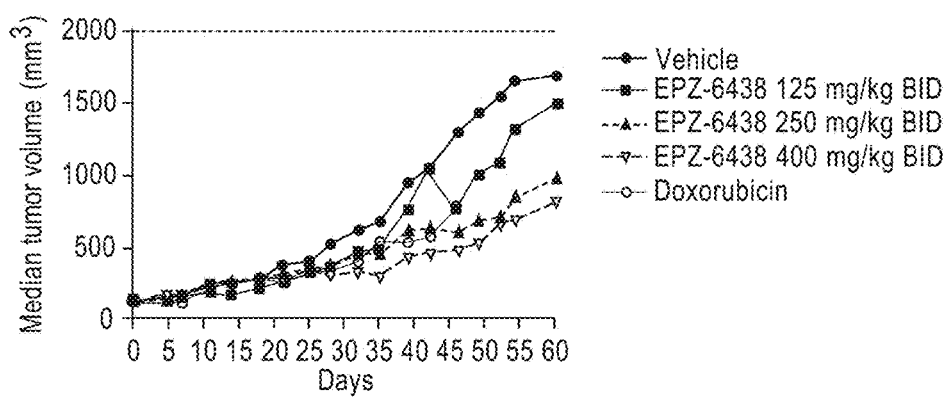
Figure 11D:
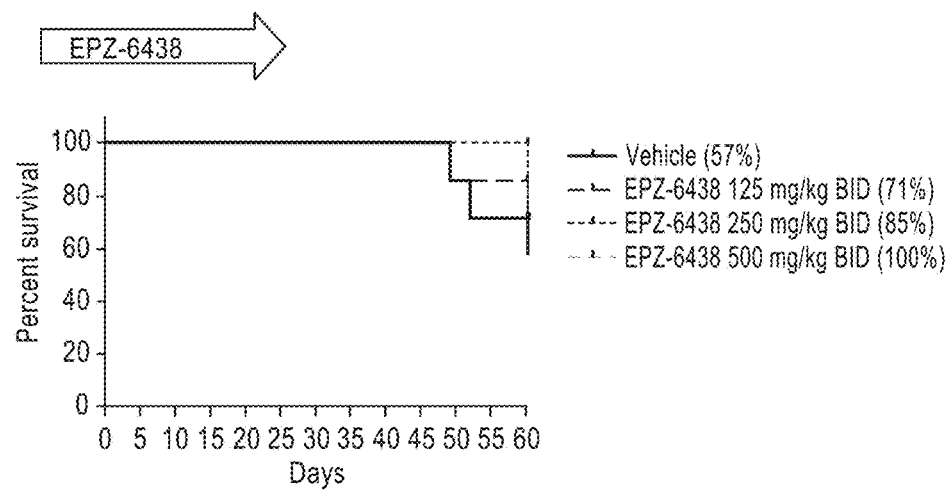

FIGS. 11A and 11C show mean in vivo tumor volumes for athymic nude mice bearing one of two different PDX of synovial sarcoma tumors. FIGS. 11B and 11D show percent survival for mice bearing a PDX. Mice were dosed with either vehicle (oral for 35 days), Compound A (oral: 125 mg/kg, 250 mg/kg, or 500/400 mg/kg for 35 days) or Doxorubicin (iv: 3 mg/kg, once a week for 3 weeks). FIGS. 11A and 11B show data from mice bearing PDX from a 57 year old male with high-grade spindle cell sarcoma. FIGS. 11C and 11D show data from mice bearing PDX from a 16 year old female. In contrast to the HS-SY-II cell line xenografts, the PDX mice exhibited dose-related tumor volume decrease in vivo.

FIGS. 12A and 12B shows array data from synovial sarcoma PDX tumors from subsets of mice that were harvested on day 35 and analyzed by RNA-seq analysis. FIG. 12A is data from mice bearing PDX from the 57 year old male; FIG. 2B is data from mice bearing PDX from the 16 year old female. Expression of HLA genes, Fas, and KLRD1, were increased in mice treated with 400 mg/kg Compound A relative to mice treated with either with vehicle. In the figure, blue is low expression and red is high expression.

Materials and Methods

Cell Culture

HS-SY-II (RCB2231, RIKEN BioResource Center) and SW982 (HTB-93, ATCC) were grown in RPMI1640 with 10% FBS under 37° C., 5% $CO_2$ condition. HS-SY-II cells were characterized to have a fusion of SS18-SSX1, while SW982 cells have a wild-type SS18

H3K27 Methylation Alterations Induced by Compound A.

HS-SY-II and SW982 cells were treated with either DMSO or Compound A starting at 40 nmol/L and decreasing in fourfold dilutions for 96 hours. Cells were washed by ice cold PBS, harvested by cell scraper, and lysed with 100 µl of nuclear extraction buffer (10 mM Tris-HCl, 10 mM $MgCl_2$, 25 mM KCl, 1% Triton X-100, 8.6% Sucrose, plus 1× Halt Protease inhibitor cocktail (1861281, Thermo Scientific). Nuclei were collected by centrifugation at 600 g for 5 minutes at 4° C. and washed once with ice cold PBS. Supernatant was removed and histones extracted for one hour with 100 µL of 0.4 N cold sulfuric acid. Extracts were clarified by centrifugation at 10,000 g for 10 minutes at 4° C. and transferred to a fresh microcentrifuge tube containing 1 mL of ice cold acetone. Histones were precipitated at −20° C. for overnight, pelleted by centrifugation at 10,000 g for 10 minutes and resuspended in 100 µl of water. Histones were quantified using the BCA protein assay (23225, Pierce). The diluted histones were coated on Immulon 4HBX plates (3855, Thermo Scientific) overnight and ELISA was performed. Briefly, after blocking with PBS containing 0.05% Tween 20 and 2% bovine serum albumin (BSA), the plates were incubated with H3K27me3 antibody (#9733, Cell Signaling Technology) or total histone H3 antibody (AB 1791, Abcam). The plates were further incubated with horseradish peroxidase conjugated anti-rabbit IgG (#7074, Cell Signaling Technology), followed by incubated with TMB substrate (TMBS-0100-01, BioFx Laboratories). Subsequently, the developed colors in the wells were measured using a plate spectrophotometer (SpectraMax 250, Molecular Devices) at 450 nm (reference wavelength 650 nm). The H3K27me3 levels were adjusted to total histone H3, and expressed as fold changes to DMSO control.

FIG. 6A shows a representative plot. The range of $IC_{50}$ values (two independent experiments), shown in FIG. 6B, were determined by GraphPad Prism (GraphPad Software). Histone mark alterations were comparable between HS-SY-II and SW982, and the alterations were independent of SS18-SSX fusion protein.

PK Values and PD Alterations in HS-SY-II Xenograft Model

HS-SY-II cells were harvested during mid-log phase growth, and resuspended in Hank balanced salt solution with 50% Matrigel (BD Biosciences). Balb/C-nu mice (Charles River Laboratories Japan) received $1×10^7$ cells (0.1 mL cell suspension) subcutaneously in the right flank. Mice carrying tumors of approximately 200 $mm^3$ (31 days after injection) were sorted into treatment groups with similar mean tumor volumes. Compound A or vehicle (0.5% MC+0.1% Tween-80 in water) was administered at the indicated doses on twice a day for 7 days by oral gavage. Each dose was delivered in a volume of 0.2 mL/20 g mouse (10 mL/kg), and adjusted for the last recorded weight of individual animals. Peripheral blood samples were collected at approximately 5 minutes before and 3 hours after the last dose from Compound A-treated mice. After obtaining plasma samples by centrifugation, the analysis for plasma concentrations of Compound A was conducted by the liquid chromatography-tandem mass spectrometry (LC/MS/MS) method. The UPLC system (Acquity, Waters) equipped with a mass spectrometer (Quattro premier, MICROMASS) was used for quantification of Compound A. The concentrations are plotted (n=5) in FIG. 7A. Each bar represents a mean of plasma concentration in each group.

Tumor samples were collected at approximately 3 hours after the last dose from mice used in analysis for PK values and PD alterations. The tumor samples were stored using RNAlater (AM7020, Life technologies). Total RNA isolation and the reverse transcription were performed by RNeasy Mini Kit (74104, Qiagen) and High capacity cDNA Reverse Transcription kit (4368814, Life technologies) according to the manufacturer's instruction. The cDNA samples were used for real time-PCR as described above. The expression levels were adjusted to GAPDH and expressed as fold changes to vehicle control (FIG. 9).

Figure 10D:
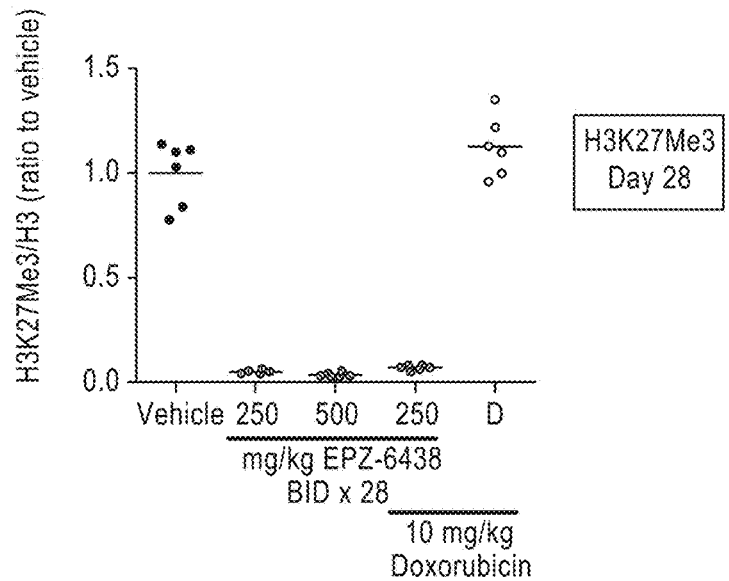
Figure 10E:
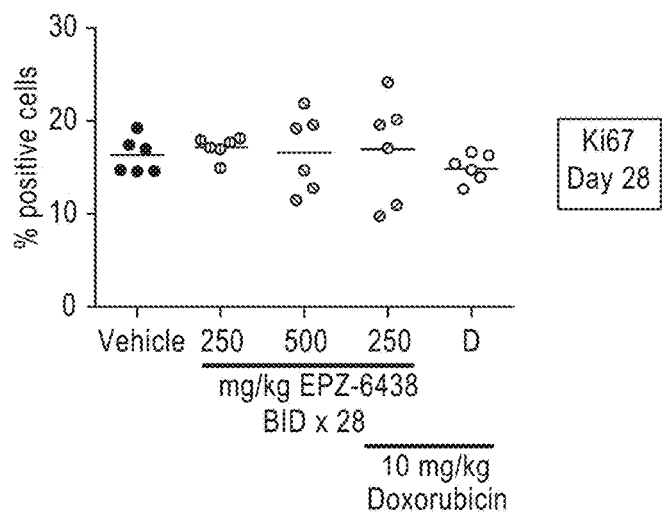

For FIG. 10D, tumors were snap-frozen in liquid nitrogen. Frozen tumor samples were cut into a 20 mg pieces and placed in 500 µL of ice cold nuclear extraction buffer (10 mM Tris-HCl, 10 mM $MgCl_2$, 25 mM KCl, 1% Triton X-100, 8.6% Sucrose, plus 1× Halt Protease inhibitor cocktail (1861281, Thermo Scientific)) and homogenized with a handy micro homogenizer. Nuclei were collected by centrifugation at 600 g for 5 minutes at 4° C. and washed once with ice cold PBS. Supernatant was removed and histones extracted for one hour with 100 µL of 0.4 N cold sulfuric acid. Extracts were clarified by centrifugation at 10,000 g for 10 minutes at 4° C. and transferred to a fresh microcentrifuge tube containing 1 mL of ice cold acetone. Histones were precipitated at −20° C. for overnight, pelleted by centrifugation at 10,000 g for 10 minutes and resuspended in 100 µl of water. Histones were quantified using the BCA protein assay (23225, Pierce). The diluted histones were coated on Immulon 4HBX plates (3855, Thermo Scientific) overnight and ELISA was performed. Briefly, after blocking with PBS containing 0.05% Tween 20 and 2% bovine serum albumin (BSA), the plates were incubated with H3K27me3 antibody (#9733, Cell Signaling Technology) or total histone H3 antibody (AB 1791, Abcam). The plates were further incubated with horseradish peroxidase conjugated anti-rabbit IgG (#7074, Cell Signaling Technology), followed by incubated with TMB substrate (TMBS-0100-01, BioFx Laboratories). Subsequently, the developed colors in the wells were measured using a plate spectrophotometer (SpectraMax 250, Molecular Devices) at 450 nm (reference wavelength 650 nm). The H3K27me3 levels were adjusted to total histone H3, and expressed as fold changes to vehicle control. The values are plotted (n=6) in FIG. 10D. Each bar represents a mean of the values in each group. The significantly reduced H3K27me3 levels were observed in tumors derived from Compound A-administered mice. Histones were extracted and quantified, and the levels of H3K27me3 were analyzed as described above. Trimethylation levels of H3K27 in the tumor are plotted (n=5) in FIG. 7B. Each bar represents a mean±SEM of the trimethylation level in each group.

Gene Expression Changes in In Vitro after the Treatment of Compound A

HS-SY-II and SW982 cells were treated with EZH2 inhibitors (Compound A or EPZ-011989) and collected at the indicated time points. Total RNA isolation and cDNA synthesis were performed using the TaqMan Gene Expression Cells-to-CT kit (4399002, Life technologies) according to the manufacturer's protocol. ATF3, EGR1, CDKN2A and GAPDH expression were analyzed by using the TaqMan Gene Expression Assays (Life technologies, 4331182) and the TaqMan Probes (Hs00231069_m1, Hs00152928_m1, Hs00233365_m1, and Hs99999905_m1, respectively). The expression levels were adjusted to GAPDH and expressed as fold changes to DMSO control (FIG. 8).

Gene Expression Changes in In Vivo after the Treatment of Compound A

Tumor samples were collected at approximately 3 hours after the last dose from mice used in analysis for PK values and PD alterations. The tumor samples were stored using RNAlater (AM7020, Life technologies). Total RNA isolation and the reverse transcription were performed by RNeasy Mini Kit (74104, Qiagen) and High capacity cDNA Reverse Transcription kit (4368814, Life technologies) according to the manufacturer's instruction. The cDNA samples were used for real time-PCR as described above. The expression levels were adjusted to GAPDH and expressed as fold changes to vehicle control (FIG. 9). Additionally or alternatively, total RNAs were isolated from frozen tumor samples. The TruSeq™ RNA Sample Prep Kit (Illumina) was used to build cDNA library for paired-end sequencing on the Illumina HiSeq (details described in Illumina TruSeq RNA Sample Preparation Guide). The Standard Cluster Generation Kit v5 binds cDNA libraries to the flow cell surface. Paired-end reads from ~50M clusters per sample were generated using TruSeq SBS kit on the Illumina HiSeq.

RNAseq Data Processing

Raw sequencing reads in FASTQ format was aligned to human genome hg19 as well as mouse genome mm10. Transcriptomic quantification was carried out with the RSEM v1.1.13 program, using USCS KnownGene transcriptome as reference. The RSEM expression calculation was run with parameters optimized for Illumina 50×50 paired end sequencing.

Analysis of RNAseq Transcriptomic Data for Biological Interpretation

Gene Set Enrichment Analysis (GSEA) was performed on Compound A vs. DMSO treated two sample comparison for both PDX models, each model treatment with 5 replicates, using the GSEA Java-enabled desktop software (Version 2.0.13, at the World Wide Web (www) broadinstitute.org/gsea/index.jsp). RSEM generated gene level counts after normalization were used for GSEA input. Permutation was carried out on gene set, rather than phenotype, to accommodate small sample size. Curated KEGG pathway as well as transcription factor binding motif gene sets from MSigDB version 4.0 at the World Wide Web (www) broadinstitute.org/gsea/msigdb/index.jsp) were used for all GSEA analyses.

For FIG. 10E, collected tumors were subjected to formalin fixation, embedded in paraffin. Paraffin sections were prepared, deparaffinized and processed for IHC following a general process according to a polymer-based method (En-Vision, DAKO, Japan). Deparaffinized sections were processed for antigen retrieval by autoclaving for 20 minutes at 121° C. under 2 atmospheric pressures in a target retrieval solution (DAKO, diluted to the final concentration of 10%), and treated with 3% hydrogen peroxide solution for 5 minutes to block endogenous peroxidase activity. A commercially available primary antibody was allowed to react with Ki-67 for approximately an hour (anti human Ki-67 mouse monoclonal antibody, DAKO, Japan, with a 1:50 dilution) at room temperature. Subsequent steps using the EnVision system followed the manufacturer's instructions, including treatment with the secondary antibody for 30 minutes at room temperature; 3,3'-diaminobenzidine was used as a chromogen and hematoxylin as a counterstain. For FIG. 10E, slides were digitized using the Aperio XT™ Scanner. Digitized slides were analyzed using Aperio Image Scope™ software to quantify the percent of positive cells. Quantification of the IHC staining for Ki67 did not show changes in cell proliferation in treatment groups. Each bar represents a mean of the values in each group. (The significant changes in the percent of Ki67 positive cells were not observed in all dosed groups.)

Synovial Sarcoma RNA-Seq Methods

The patient-derived xenograft (PDX) models CTG-0331 and CTG-0771 are low passage Champions TumorGraft™ models representing human synovial sarcoma. Immunocompromised female mice (Taconic; NCr nude) were implanted unilaterally in the flank region with tumor fragments (5 mm×5 mm×5 mm) harvested from donor animals, each implanted from a specific passage lot (CTG-0331 and CTG-0771 at P4). When tumors reached approximately 100-300 mm$^3$, animals were matched by tumor volume into treatment and control groups and dosing initiated. Vehicle (0.5% NaCMC plus 0.1% Tween 80 in water) or Compound A (500 mg/kg for CTG-0331 and 500 mg/kg decreased to 400 mg/kg on Day 17 for CTG-0771) was administered orally BID at a dose volume of 10 μL/g for 35 days. Tumor size was measured twice weekly. On Day 35, up to 5 mice with the largest tumor burden were euthanized for tumor collection 3 hours after final dose, and flash frozen. Frozen tumor samples (30 mg) from the vehicle and highest Compound A dose groups were shipped to Expression Analysis for RNA processing and RNA-seq analysis.

The entire disclosure of each of the patent documents and scientific articles referred to herein is incorporated by reference for all purposes.

The invention can be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A method of inhibiting the ability of a cancer cell to induce immune dysfunction, comprising a step of contacting the cell with a therapeutically effective amount of an EZH2 inhibitor, wherein the cell (1) comprises aberrant, misregulated, or increased EZH2 activity; or (2) comprises a chromosomal translocation t(x; 18)(p11.2;q11.2) that causes a SS18-SSX fusion gene; or (3) has reduced function and/or expression of INI1.

2. The method of claim 1, wherein the cell comprises aberrant, misregulated, or increased EZH2 activity.

3. The method of claim 1, wherein the cell comprises a chromosomal translocation t(x; 18)(p11.2;q11.2), wherein the translocation causes a SS18-SSX fusion gene.

4. The method of claim 1, wherein the cell has reduced function or expression of INI1.

5. The method of claim 4, wherein the cell has reduced function and expression of INI1.

6. The method of claim 1, wherein the EZH2 inhibitor is Compound A, having the following formula:

(A)
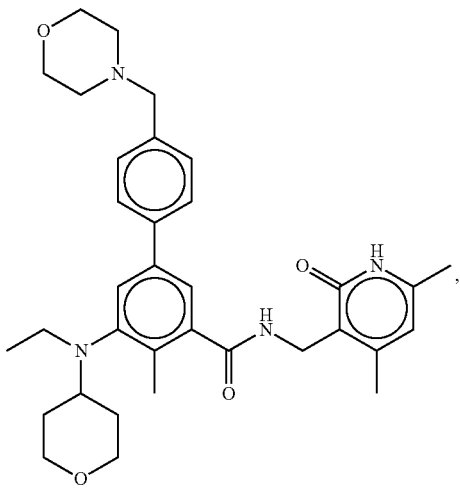

or a pharmaceutically acceptable salt thereof.

7. The method of claim 1, wherein the EZH2 inhibitor is selected from the group consisting of (B)

(C)

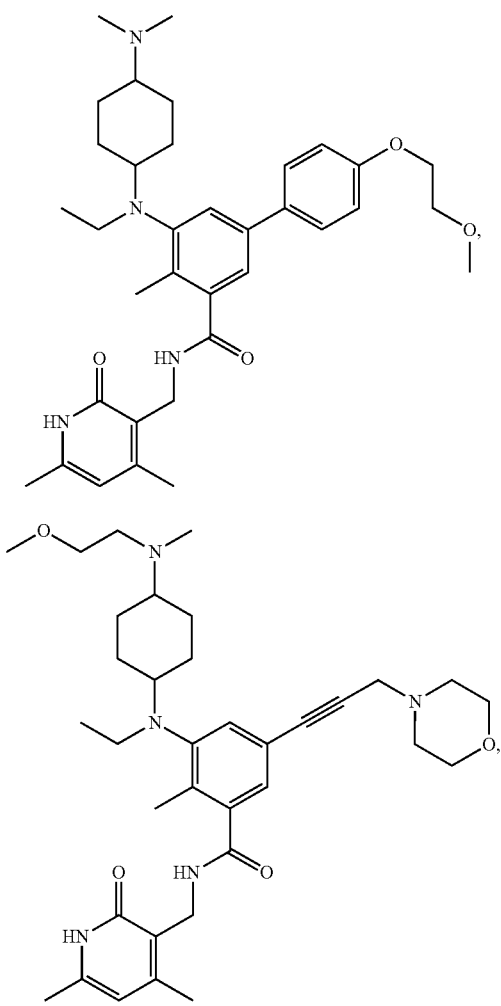

(D)

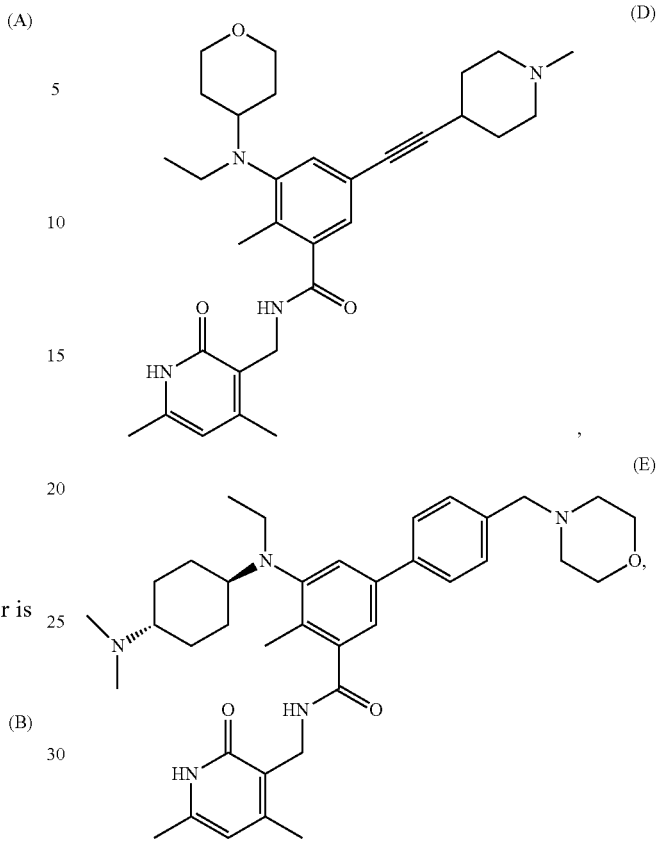

(E)

and pharmaceutically acceptable salts thereof.

8. The method of claim 1, wherein the cancer cell is in a subject.

9. The method of claim 8, wherein the subject is human.

10. The method of claim 1, wherein the ability of the cancer cell to induce immune dysfunction is characterized by reduced expression of one or more of MHC, β2 microglobulin, Tumor Necrosis Factor (TNF) receptor, Low Molecular Mass Polypeptide 2 (LMP2), Low Molecular Mass Polypeptide 7 (LMP7), Transporter Associated with Antigen Processing (TAP), and TAP-associated glycoprotein (tapasin) in the cancer cell when compared to a non-cancerous cell.

11. The method of claim 10, wherein the MHC is human leukocyte antigen (HLA), wherein the HLA is selected from the group consisting of HLA-A, HLA-B, HLA-C, HLDA-DM alpha, HLA-DM beta, HLA-DO alpha, HLA-DO beta 1, HLA-DP alpha 1, HLA-DP beta 1, HLA-DR alpha, HLA-DR beta 1, HLA-DR beta 3, HLA-DR beta 4, HLA-E, HLA-F, HLA-G, HLA-K, and HLA-L.

12. A method of treating or alleviating symptoms of a disorder characterized by cancer-cell induced immune dysfunction in a subject comprising a step of administering to the subject a therapeutically effective amount of an EZH2 inhibitor; wherein the subject (1) comprises a chromosomal translocation t(x; 18) that causes a SS18-SSX fusion gene; or (2) has reduced function and/or expression of INI1.

13. The method of claim 12, wherein the subject comprises aberrant, misregulated, or increased EZH2 activity.

14. The method of claim 12, wherein the subject comprises a chromosomal translocation t(x; 18)(p11.2;q11.2), wherein the translocation causes a SS18-SSX fusion gene.

15. The method of claim 12, wherein the subject has reduced function or expression of INI1.

16. The method of claim 15, wherein the subject has reduced function and expression of INI1.

17. The method of claim 12, wherein the EZH2 inhibitor is Compound A, having the following formula:

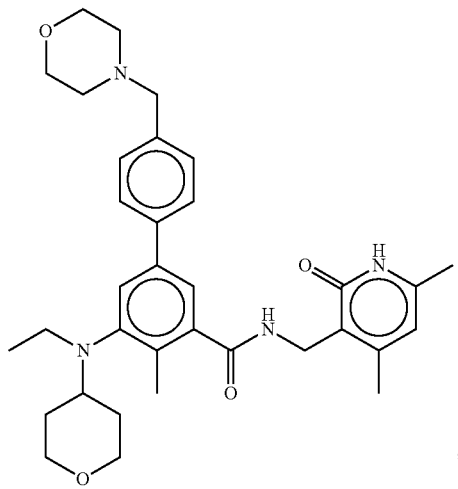

(A)

or a pharmaceutically acceptable salts thereof.

18. The method of claim 12, wherein the EZH2 inhibitor is selected from the group consisting of

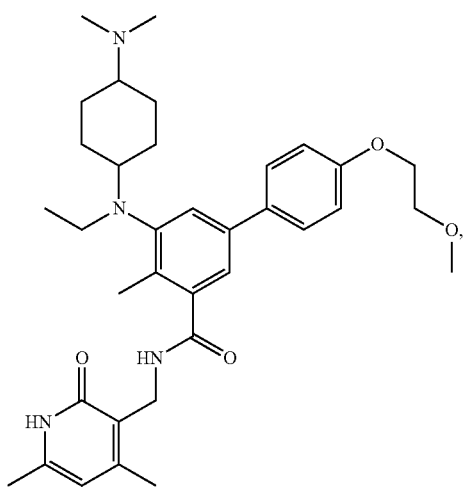

(B)

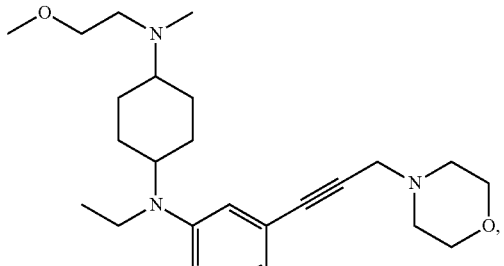

(C)

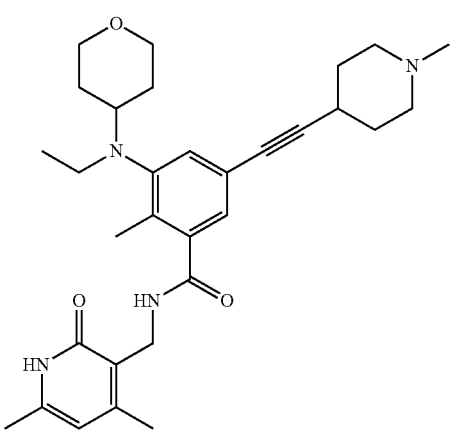

(D)

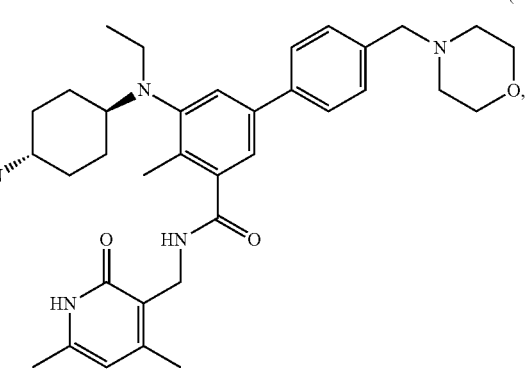

(E)

and pharmaceutically acceptable salts thereof.

19. The method of claim 12, wherein the method further comprises administering a chemotherapeutic compound.

20. The method of claim 19, wherein the chemotherapeutic compound is selected from the group consisting of a PD-1 inhibitor, a PD-L1 inhibitor, and a CTLA-4 inhibitor.

* * * * *

UNITED STATES PATENT AND TRADEMARK OFFICE
CERTIFICATE OF CORRECTION

| | | |
|---|---|---|
| PATENT NO. | : 10,369,155 B2 | Page 1 of 1 |
| APPLICATION NO. | : 15/851978 | |
| DATED | : August 6, 2019 | |
| INVENTOR(S) | : Heike Keilhack | |

It is certified that error appears in the above-identified patent and that said Letters Patent is hereby corrected as shown below:

In the Claims

At Column 66, Claim number 12, Line number 64:
"or (2) has reduced function and/or expression of INTL."
Should read:
--or (2) has reduced function and/or expression of INI1.--

At Column 67, Claim number 17, Line number 35:
"or a pharmaceutically acceptable salts thereof."
Should read:
--or a pharmaceutically acceptable salt thereof.--

Signed and Sealed this
Twenty-first Day of April, 2020

Andrei Iancu
*Director of the United States Patent and Trademark Office*